(12) United States Patent
Sharma et al.

(10) Patent No.: US 8,114,844 B2
(45) Date of Patent: Feb. 14, 2012

(54) LINEAR AND CYCLIC MELANOCORTIN RECEPTOR-SPECIFIC PEPTIDOMIMETICS

(75) Inventors: Shubh D. Sharma, Cranbury, NJ (US); Margarita Bastos, Plainsboro, NJ (US); Wei Yang, Edison, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 742 days.

(21) Appl. No.: 12/244,880

(22) Filed: Oct. 3, 2008

(65) Prior Publication Data

US 2009/0069224 A1    Mar. 12, 2009

Related U.S. Application Data

(63) Continuation-in-part of application No. 11/694,181, filed on Mar. 30, 2007, now Pat. No. 7,964,181.

(60) Provisional application No. 60/977,159, filed on Oct. 3, 2007, provisional application No. 60/743,963, filed on Mar. 30, 2006, provisional application No. 60/743,964, filed on Mar. 30, 2006, provisional application No. 60/743,960, filed on Mar. 30, 2006, provisional application No. 60/743,961, filed on Mar. 30, 2006.

(51) Int. Cl.
    *A61K 38/12*    (2006.01)
    *A61K 38/08*    (2006.01)
    *C07D 403/00*   (2006.01)

(52) U.S. Cl. ................. 514/21.1; 514/21.7; 544/121

(58) Field of Classification Search .................. None
    See application file for complete search history.

(56) References Cited

U.S. PATENT DOCUMENTS

| | | | |
|---|---|---|---|
| 4,251,438 A | 2/1981 | Moon | |
| 4,341,698 A | 7/1982 | Carr et al. | |
| 5,559,232 A | 9/1996 | Ackermann et al. | |
| 5,929,237 A | 7/1999 | Kahn | |
| 6,013,458 A | 1/2000 | Kahn et al. | |
| 6,184,223 B1 | 2/2001 | Kahn et al. | |
| 6,413,963 B2 | 7/2002 | Kahn et al. | |
| 6,943,157 B2 | 9/2005 | Nagula et al. | |
| 7,008,941 B2 | 3/2006 | Urban et al. | |
| 2002/0111348 A1 | 8/2002 | Reichard et al. | |
| 2003/0019049 A9 | 1/2003 | Kravtchenko et al. | |
| 2006/0217532 A1 | 9/2006 | Miao et al. | |
| 2006/0234923 A1 | 10/2006 | Zumbrunn et al. | |

FOREIGN PATENT DOCUMENTS

| | | |
|---|---|---|
| DE | 3022401 | 1/1981 |
| FR | 2717484 | 9/1995 |
| WO | WO 92/21361 | 12/1992 |
| WO | WO-99/48913 | 9/1999 |
| WO | WO-99/55684 | 11/1999 |
| WO | WO 02/085925 | 10/2002 |
| WO | WO 2007/115175 | 10/2007 |
| WO | WO 2007/115182 | 10/2007 |

OTHER PUBLICATIONS

Batt, 1994, Bioorganic & Medicinal Chemistry, 4, 867-872.*
DiMaio, 1979, Peptides: Structure and Biological Function: Proc., 889-892.*
S.M. Hecht, Bioorganic Chemistry: Peptides and Proteins, Oxford University Press, 1998, 395-419.
Rubsam, F., et al., Synthesis of chiral piperazinones as versatile scaffolds for peptidomimetics, Tetrahedron, 2000, 56(43) 8481-8487.
Kolter, T., et al., Synthesis of substituted chiral piperazinones as building blocks for peptidomimetics, Liebigs Annalen, 1995, 4, 625-629.
DiMaio, John et al., Synthesis of Chiral Piperazin-2-ones as Model Peptidomimetics, J. Chem. Soc., 1989, 1687-1689.
Dutta, A.S., Potent Cyclic Monomeric and Dimeric Peptide, etc., Journal of Peptide Science, 2000, vol. 6, 321-341, especially pp. 323-325, Table 1, compounds 47-58.
de Sisser, Solid-phase synthesis of polymyxin B1 and analogues via., etc., P.C.J. Peptide Res. 2003, vol. 61, 298-306, especially p. 303, Table 1, compounds 27-28.
Masuzawa, et al., The Reaction of C-Substituted Ethylenediamine with the Ester of Alpha-Halo Acid, Apr. 1965, vol. 38, No. 12, 2078-2081.
Shreder, K., et al, "Synthesis of a Constrained Enkephalin Analog to Illustrate a Novel Route to the Piperazinone Ring Structure", Tetrahedron Letters, Elsevier, Amsterdam vol. 39, No. 3-4, Jan. 15, 1998, pp. 221-224, ISSN: 0040-4039.
Communication from European Patent Office in European Patent Application 07759821.7, dated Oct. 2, 2009, and including Supplementary European Search Report and European Search Opinion.

* cited by examiner

*Primary Examiner* — Cecilia J Tsang
*Assistant Examiner* — Satyanarayana R Gudibande
(74) *Attorney, Agent, or Firm* — Stephen A. Slusher

(57) ABSTRACT

Linear and cyclic peptidomimetics which bind to one or more melanocortin receptors are provided, which peptidomimetics include at least one ring-constrained amino acid surrogate of formula I:

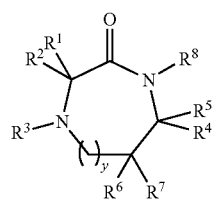

where $R^1$, $R^2$, $R^3$, $R^4$, $R^5$, $R^6$, $R^7$, $R^8$, and y are as defined in the specification, together with methods for synthesizing ring-constrained amino acid surrogates of formula I and peptidomimetics incorporating the same, and methods of use of peptidomimetics in the treatment of various diseases, syndromes and conditions.

7 Claims, No Drawings

LINEAR AND CYCLIC MELANOCORTIN RECEPTOR-SPECIFIC PEPTIDOMIMETICS

CROSS-REFERENCE TO RELATED APPLICATIONS

This application is a continuation-in-part of U.S. patent application Ser. No. 11/694,181 entitled "Amino Acid Surrogates for Peptidic Constructs", filed on Mar. 30, 2007, which claims priority to and the benefit of the filing of the following: U.S. Provisional Patent Application Ser. No. 60/743,963 entitled "Linear Natriuretic Peptide Constructs", filed on Mar. 30, 2006; U.S. Provisional Patent Application Ser. No. 60/743,964 entitled "Linear Natriuretic Peptide Constructs with Prosthetic Groups", filed on Mar. 30, 2006; U.S. Provisional Patent Application Ser. No. 60/743,960 entitled "Cyclic Natriuretic Peptide Constructs", filed on Mar. 30, 2006; and U.S. Provisional Patent Application Ser. No. 60/743,961 entitled "Cyclic Natriuretic Peptide Constructs with Prosthetic Groups", filed on Mar. 30, 2006. The specification and claims of each of the foregoing are incorporated herein by reference.

This application claims priority to and the benefit of the filing of U.S. Provisional Patent Application Ser. No. 60/977,159 entitled "Linear and Cyclic Melanocortin Receptor-Specific Peptidomimetics", filed on Oct. 3, 2007, and the specification and claims thereof are incorporated herein by reference.

BACKGROUND OF THE INVENTION

1. Field of the Invention (Technical Field)

The present invention provides linear and cyclic peptidomimetics that are specific for one or more melanocortin receptors, and which may be used in the treatment of a wide variety of diseases, syndromes and conditions.

2. Background Art

Melanocortin Receptors. A family of melanocortin receptor types and subtypes have been identified, including melanocortin-1 receptors (MC1-R) expressed on normal human melanocytes and melanoma cells, melanocortin-2 receptors (MC2-R) for ACTH (adrenocorticotropin) expressed in cells of the adrenal gland, melanocortin-3 and melanocortin-4 receptors (MC3-R and MC4-R) expressed primarily in cells in the hypothalamus, mid-brain and brainstem, and melanocortin-5 receptors (MC5-R), expressed in a wide distribution of central nervous system and peripheral tissues.

A wide variety of diseases, conditions and syndromes have been identified for which compounds specific for one or more melanocortin receptors may have utility. For example, compounds that are specific for MC1-R, particularly agonists, may be useful as tanning agents by increasing melanin production. Compounds specific for MCR-1 and MCR-3 may be useful in regulation of inflammatory processes. Compounds specific for MC3-R or MC4-R are believed to be useful in regulation of energy homeostasis, including use as agents for attenuating food intake and body weight gain, for use in treatment of anorexia, as a weight gain aid, for treatment of obesity, and treatment of other food intake and metabolism-related purposes. Compounds specific for MC3-R and MC4-R can further be used as agents for treatment of sexual dysfunction, including male erectile dysfunction and female sexual dysfunction. Compounds specific for MC4-R can further be used as agents for treatment of alcohol abuse, anxiety and related conditions.

Both peptide and small molecule melanocortin receptor-specific compounds have been developed and explored for treatment of certain of the foregoing and other conditions. However, to date no melanocortin receptor-specific compound has been approved for any clinical indication, and very few have been tested in human clinical trials.

In general, melanocortin receptor-specific peptides have limitations associated with peptide-based drugs. These include enzymatic degradation, short circulation half life, limited bioavailability, inadequate efficacy, short duration of effect, limitations on routes of administration and the like. Thus there remains a significant need for compounds with the favorable characteristics of peptides, such as high specificity for discrete melanocortin receptors, partial or full agonists, partial or full antagonists, mixed agonist-antagonists, inverse agonists, or antagonists of inverse agonists, but with improved resistance to enzymatic degradation, or improved circulation half life, or improve bioavailability, or improved efficacy, or other advantageous characteristics. It is against this background that the present invention was made.

SUMMARY OF THE INVENTION

Disclosure of the Invention

In one aspect, the invention provides a peptidomimetic of the formula

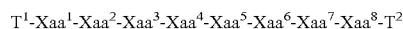

$T^1$-Xaa$^1$-Xaa$^2$-Xaa$^3$-Xaa$^4$-Xaa$^5$-Xaa$^6$-Xaa$^7$-Xaa$^8$-$T^2$ or a pharmaceutically acceptable salt thereof, wherein:
$T^1$ is H or an N-terminal group;
Xaa$^1$ is optionally present, and if present, is an amino acid with a side chain including at least one primary amine, guanidine, urea, alkyl or cycloalkyl, or Xaa$^1$ is an amino acid surrogate of the structure:

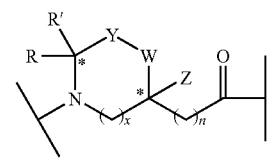

wherein the solid lines indicate a bond; R and R' are independently H, a linear or branched $C_1$ to $C_6$ aliphatic chain, —$(CH_2)_y$—S—$CH_3$, —$(CH_2)_y$—S(=O)—$CH_3$, —$(CH_2)_y$—S($O_2$)—$CH_3$, —$(CH_2)_y$—$NH_2$, —$(CH_2)_y$—NH—C(=NH)—$NH_2$, —$(CH_2)_y$—NH—$(CH_2)_y$—$NH_2$, —$(CH_2)_y$—NH—C(=O)—$NH_2$, —$(CH_2)_y$—C(=O)—$NH_2$, a bond and a cyclopropane, cyclobutane, cyclopentane, or cyclohexane ring, or a $C_1$ to $C_3$ aliphatic chain and a cyclopropane, cyclobutane, cyclopentane, or cyclohexane ring; x is 1 or 2; Y is $CH_2$ or C=O; W is $CH_2$, NH or NR'''; Z is H or $CH_3$; R''' is an acyl, a $C_1$ to $C_{17}$ linear or branched alkyl chain, a $C_2$ to $C_{19}$ linear or branched alkyl acyl chain, a $C_1$ to $C_{17}$ linear or branched omega amino aliphatic, or a $C_1$ to $C_{17}$ linear or branched omega amino aliphatic acyl; n is 0, 1 or 2; m is 0 to 17; y is 1 to 5; $v_3$ and $v_4$ are each independently H, a $C_1$ to $C_{17}$ linear or branched alkyl chain or a $C_2$ to $C_{19}$ linear or branched alkyl acyl chain, on the proviso that if one of $v_3$ or $v_4$ is an alkyl acyl chain, then the other of $v_3$ or $v_4$ is H; and the carbon atoms marked with an asterisk can have any stereochemical configuration;

Xaa$^2$ and Xaa$^7$ are the same or different, and are each L- or D-isomer amino acid residues forming a cyclic bridge through the side chains of each of Xaa$^2$ and Xaa$^7$ wherein the linking group of the cyclic bridge comprises —S—S—, —S—$CH_2$—S—, —S—$CH_2$—, —$CH_2$—S—, —C(=O)—

NH—, —NH—C(=O)—, —CH₂—NH—, —NH—CH₂—, —CH₂—S(O)ₙ— where n is 1 or 2, —S(O)ₙ—CH₂— where n is 1 or 2, —CH₂—CH₂—, —CH=CH— (E or Z), —C≡C—, —C(=O)—O—, —O—C(=O)—, —C(=O)—CH₂—, —CH₂—C(=O)—, —NH—C(=O)—(CH₂)ₘ—C(=O)—NH— where m is from 1 to about 8, —C(=O)—(CH₂)ₘ—C(=O)— where m is from 1 to about 8, —O—C(=O)—NH—, —NH—C(=O)—O—, or —NH—C(=O)—NH—;

Xaa³ is an amino acid with a side chain including at least one primary amine, secondary amine, amide, alkyl, cycloalkyl, cycloheteroalkyl, aryl, heteroaryl, ether, sulfide, or carboxyl, or Xaa³ is Pro, optionally substituted with hydroxyl, halogen, sulfonamide, alkyl, alkoxy, aryl, alkylaryl, alkylaryloxy, alkyl-alkoxy-aryl, or aryloxy;

Xaa⁴ is an amino acid with a side chain including phenyl or naphthyl, optionally substituted with one or more ring substituents, and when one or more substituents are present, are the same or different and independently alkyl, haloalkyl, cycloalkyl, alkoxy, alkylthio, halo, nitro, acyl, cyano, aryl, alkylaryl, aryloxy, amino, monosubstituted amino, disubstituted amino, sulfonamide, hydroxy, carboxy, or alkoxy-carbonyl;

Xaa⁵ is Pro, an amino acid with a side chain including at least one primary amine, secondary amine, guanidine, urea, alkyl, cycloalkyl, cycloheteroalkyl, aryl, heteroaryl, or ether, or Xaa⁵ is an amino acid surrogate of the structure:

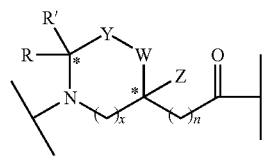

wherein the solid lines indicate a bond; at least one of R and R' is (CH₂)ᵧ—R" and if one, the remaining of R and R' is H, where R" is:
—NH₂,
—NH—C(=NH)—NH₂,
—NH—(CH₂)ᵧ—NH₂,
—NH—C(=O)—NH₂,
—C(=O)—NH₂,
—C(=O)—NH—CH₃,
—C(=O)—NH—(CH₂)ᵧ—NH₂,
—NH—C(=NH)—NH-Me,
—NH—C(=NH)—NH-Et,
—NH—C(=NH)—NH—Pr,
—NH—C(=NH)—NH—Pr-i,
—NH—C(=O)—CH₃,
—NH—C(=O)—CH₂—CH₃,
—NH—C(=O)—CH—(CH₃)₂,
—NH—C(=O)—O—CH₃,
—NH—C(=O)—O—CH₂—CH₃,
—NH—C(=O)—O—C—(CH₃)₃,
—NH—C(=O)—NH—CH₃,
—NH—C(=N—C(=O)—O—C—(CH₃)₃)—NH—C(=O)—O—C—(CH₃)₃,
—N(C(=O)—O—C—(CH₃)₃)—C(=NH)—NH—C(=O)—O—C—(CH₃)₃,

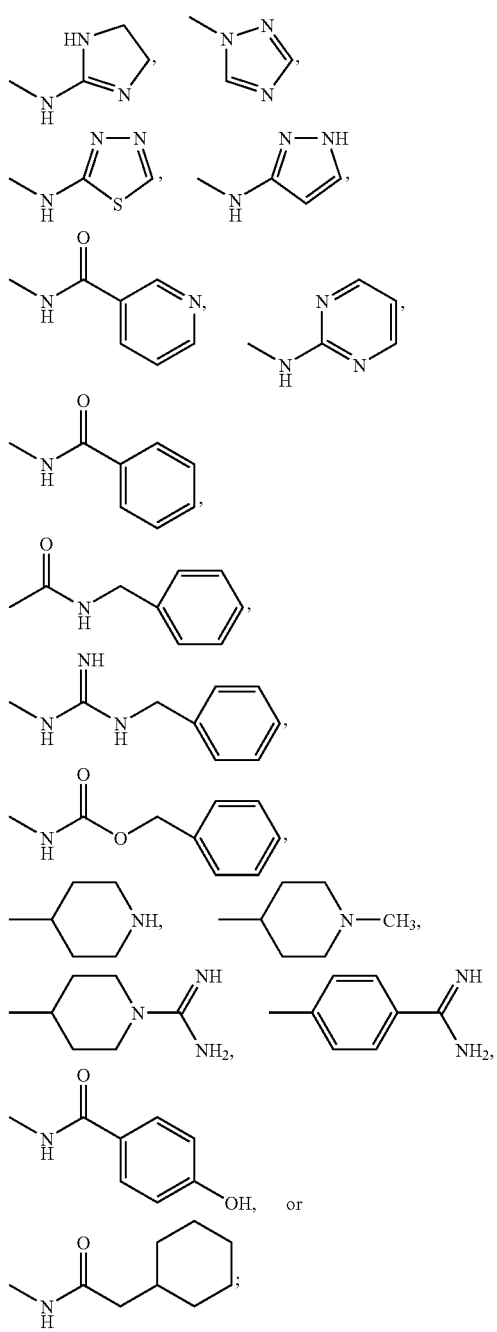

x is 1 or 2; Y is CH₂ or C=O; W is CH₂, NH or NR'''; Z is H or CH₃; R''' is an acyl, a C₁ to C₁₇ linear or branched alkyl chain, a C₂ to C₁₉ linear or branched alkyl acyl chain, a C₁ to C₁₇ linear or branched omega amino aliphatic, or a C₁ to C₁₇ linear or branched omega amino aliphatic acyl; v₁ and v₂ are each independently H or a C₁ to C₁₇ linear or branched alkyl chain; n is 0, 1 or 2; m is 0 to 17; y is 1 to 5; and the carbon atoms marked with an asterisk can have any stereochemical configuration;

Xaa⁶ is an amino acid with a side chain including at least one aryl or heteroaryl, optionally substituted with one or more ring substituents, and when one or more substituents are present, are the same or different and independently alkyl, haloalkyl, cycloalkyl, alkoxy, alkylthio, halo, nitro, acyl, cyano, aryl, alkylaryl, aryloxy, amino, monosubstituted amino, disubstituted amino, sulfonamide, hydroxy, carboxy, or alkoxy-carbonyl;

Xaa⁸ is optionally present, and if present, is an amino acid with a side chain including at least one group capable of hydrogen bond donation or hydrogen bond acceptance; and T² is a C-terminal group;

on the proviso that at least one of Xaa¹ and Xaa⁵ is an amino acid surrogate.

In the peptidomimetic of the foregoing formula, Xaa¹ can be an L- or D-isomer of Dap, Dab, Orn, Lys, Cit or Arg and Xaa⁵ can be an amino acid surrogate.

In the peptidomimetic of the foregoing formula, Xaa⁴ can be D-Phe, optionally wherein the phenyl ring is substituted with one or more ring substituents, and when one or more substituents are present, are the same or different and independently alkyl, haloalkyl, cycloalkyl, alkoxy, alkylthio, halo, nitro, acyl, cyano, aryl, alkylaryl, aryloxy, amino, monosubstituted amino, disubstituted amino, sulfonamide, hydroxy, carboxy, or alkoxy-carbonyl.

In the peptidomimetic of the foregoing formula, the cyclic bridge formed by the side chains of Xaa² and Xaa⁷ can include —C(=O)—NH— or —NH—C(=O)—.

In the peptidomimetic of the foregoing formula, the N-terminal group can be a $C_1$ to $C_7$ acyl group, a linear or branched $C_1$ to $C_{17}$ alkyl, aryl, heteroaryl, alkene, alkenyl, or aralkyl chain or an N-acylated linear or branched $C_1$ to $C_{17}$ alkyl, aryl, heteroaryl, alkene, alkenyl, or aralkyl chain and the C-terminal group can be a carboxyl, an amide, an amide substituted with one or two linear or branched $C_1$ to $C_{17}$ alkyl, cycloalkyl, aryl, heteroaryl, alkylaryl, alkene, alkenyl, or aralkyl chains, or a linear or branched $C_1$ to $C_{17}$ alkyl, cycloalkyl, aryl, heteroaryl, alkene, alkenyl, or aralkyl chain.

In another aspect, the invention provides a linear or cyclic peptidomimetic with an N-terminus and a C-terminus which binds to a melanocortin receptor and comprises a plurality of amino acid residues and at least one amino acid surrogate of formula I:

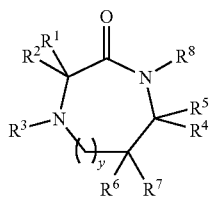

I or an enantiomer, stereoisomer or diastereoisomer thereof, wherein:

$R^1$ is H, alkyl, aryl, alkylaryl, alkyl-N($R^9$)$_2$, alkyl-OR⁹, alkyl-C(=O)OR⁹, C(=O)OR⁹, alkyl-S—R⁹, alkyl-C(=O)N($R^9$)$_2$, or a group of a formula:

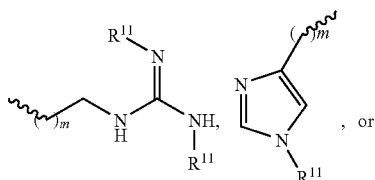

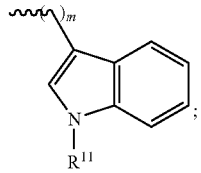

$R^2$ is H or alkyl;

$R^3$ is H or a first nitrogen protecting group;

$R^4$ is H, alkyl, (CH$_2$)$_m$C(=O)OH, (CH$_2$)$_m$C(=O)NR¹⁰, (CH$_2$)$_m$C(=O)OR¹⁰, (CH$_2$)$_q$OH, (CH$_2$)$_q$OBn, (CH$_2$)$_q$Oallyl, (CH$_2$)$_m$C(=O)N($R^9$)$_2$, or (CH$_2$)$_m$C(=O)N($R^9$)(CH$_2$)$_p$N($R^9$)$_2$;

$R^5$ is H or alkyl;

$R^6$ is H, alkyl, (CH$_2$)$_m$C(=O)OH, (CH$_2$)$_m$C(=O)NR¹⁰, (CH$_2$)$_m$C(=O)OR¹⁰, (CH$_2$)$_q$OH, (CH$_2$)$_q$OBn, (CH$_2$)$_q$Oallyl, (CH$_2$)$_m$C(=O)N($R^9$)$_2$, or (CH$_2$)$_m$C(=O)N($R^9$)(CH$_2$)$_p$N($R^9$)$_2$;

$R^7$ is H or alkyl;

provided that both of $R^4$ and $R^6$ are not (CH$_2$)$_m$C(=O)OH, (CH$_2$)$_m$C(=O)NR¹⁰, (CH$_2$)$_m$C(=O)OR¹⁰, (CH$_2$)$_q$OH, (CH$_2$)$_q$OBn, (CH$_2$)$_q$Oallyl, (CH$_2$)$_m$C(=O)N($R^9$)$_2$, or (CH$_2$)$_m$C(=O)N($R^9$)(CH$_2$)$_p$N($R^9$)$_2$;

$R^8$ is H, C(=O)alkyl, C(=O)(CH$_2$)$_m$(NR⁹)$_2$, alkyl, aralkyl, or aryl;

each occurrence of $R^9$ is independently H, aryl, or alkyl;

$R^{10}$ is a peptide solid support or one or more amino acid residues;

$R^{11}$ is H or a second nitrogen protecting group;

each occurrence of m is an independent integer having a value between 0 and 6;

each occurrence of q is an independent integer having a value between 1 and 6;

p is an integer having a value between 1 and 10; and y is 0 or 1.

The invention further comprises a method for stimulating sexual response in a mammal, comprising administering a pharmaceutically sufficient amount of a composition comprising a peptidomimetic or pharmaceutically acceptable salt thereof. In this method, the mammal may be a male or a female. The composition may further comprise a pharmaceutically acceptable carrier. In the method, administering may include administering by any method of administration, such as administration by injection, administration through mucous membranes, buccal administration, oral administration, dermal administration, inhalation administration, nasal administration, parenteral administration, pulmonary administration, ocular administration, sublingual administration and vaginal administration. In the event of nasal administration, it may be nasal administration of a metered amount of a formulation comprising an aqueous buffer.

The invention further comprises a method for inhibiting food uptake in a mammal, comprising administering a pharmaceutically sufficient amount of a composition comprising a peptidomimetic or pharmaceutically acceptable salt thereof, and particularly an MC3/4-R selective agonist or partial agonist. The composition may further comprise a pharmaceutically acceptable carrier. In the method, administering may include administering by any method of administration, such as administration by injection, administration through mucous membranes, buccal administration, oral administration, dermal administration, inhalation administration, nasal administration, parenteral administration, pulmonary administration, ocular administration and sublingual administration. In the event of nasal administration, it may be nasal administration of a metered amount of a formulation comprising an aqueous buffer.

The invention further comprises a method for increasing weight gain in a mammal, comprising administering a pharmaceutically sufficient amount of a composition comprising a peptidomimetic or pharmaceutically acceptable salt thereof, and particularly an MC3/4-R selective antagonist. The composition may further comprise a pharmaceutically acceptable carrier. In the method, administering may include administering by any method of administration, such as administration by injection, administration through mucous membranes, buccal administration, oral administration, dermal administration, inhalation administration, nasal administration, parenteral administration, pulmonary administration, ocular administration and sublingual administration. In the event of nasal administration, it may be nasal administration of a metered amount of a formulation comprising an aqueous buffer.

An object of the present invention is a melanocortin receptor-specific pharmaceutical for use in treatment of sexual dysfunction.

Another object is to provide a melanocortin receptor-specific pharmaceutical for use in treatment of male sexual dysfunction, including erectile dysfunction.

Another object is to provide a melanocortin receptor-specific pharmaceutical for use in treatment of female sexual dysfunction.

Another object is to provide a melanocortin receptor-specific pharmaceutical for use in treatment of eating disorders.

Another object is to provide a melanocortin receptor-specific pharmaceutical for use in treatment of which is effective by nasal administration.

Another object of this invention is to provide compounds which are specific for melanocortin receptors MC1-R and/or MC3-R and/or MC4-R and/or MC5-R and which are agonists or antagonists.

Other objects, advantages and novel features, and the further scope of applicability of the present invention, will be set forth in part in the detailed description to follow, and in part will become apparent to those skilled in the art upon examination of the following, or may be learned by practice of this invention. The objects and advantages of this invention may be realized and attained by means of the instrumentalities and combinations particularly pointed out in the appended claims.

DESCRIPTION OF THE PREFERRED EMBODIMENTS

Best Modes for Carrying Out the Invention

1. Definitions

"Alkyl Group"

As used herein, the term "alkyl group" means a saturated, monovalent, unbranched or branched hydrocarbon chain. Examples of alkyl groups include, but are not limited to, ($C_1$-$C_6$) alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl, and octyl. An alkyl group can be unsubstituted or optionally substituted with one or two suitable substituents.

"Aliphatic"

As used herein, the term "aliphatic" means compounds with hydrocarbon chains, such as for example alkanes, alkenes, alkynes, and derivatives thereof.

An "omega amino aliphatic" means an aliphatic moiety with a terminal amino group. Examples of omega amino aliphatics include 7'-amino-heptanoyl and the amino acid side chain moieties of ornithine and lysine.

"Alkenyl Group"

As used herein, the term "alkenyl group" means a monovalent, unbranched or branched hydrocarbon chain having one or more double bonds therein. The double bond of an alkenyl group can be unconjugated or conjugated to another unsaturated group. Suitable alkenyl groups include, but are not limited to ($C_2$-$C_6$) alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or optionally substituted with one or two suitable substituents.

"Alkynyl Group"

As used herein, the term "alkynyl group" means monovalent, unbranched or branched hydrocarbon chain having one or more triple bonds therein. The triple bond of an alkynyl group can be unconjugated or conjugated to another unsaturated group. Suitable alkynyl groups include, but are not limited to, ($C_2$-$C_6$) alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl group can be unsubstituted or optionally substituted with one or two suitable substituents.

"Aralkyl"

The term "aralkyl" means a radical —$R^a R^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like.

"Aryl Group"

As used herein, the term "aryl group" means a monocyclic or polycyclic-aromatic radical comprising carbon and hydrogen atoms. Examples of suitable aryl groups include, but are not limited to, phenyl, tolyl, anthacenyl, fluorenyl, indenyl, azulenyl, naphthyl, 1-naphthyl, 2-naphthyl, and biphenyl as well as benzo-fused carbocyclic moieties such as 5,6,7,8-tetrahydronaphthyl. An aryl group can be unsubstituted or optionally substituted with one or two suitable substituents as defined below. An aryl group optionally may be fused to a cycloalkyl group, fused to another aryl group, fused to a heteroaryl group, or fused to a heterocycloalkyl group. Preferred aryl groups include, but are not limited to, monocyclic or bicyclic aromatic hydrocarbon radicals of 6 to 12 ring atoms, and optionally substituted independently with one or more substituents selected from alkyl, haloalkyl, cycloalkyl, alkoxy, alkylthio, halo, nitro, acyl, cyano, aryl, alkylaryl, aryloxy, amino, monosubstituted amino, disubstituted amino, sulfonamide, hydroxy, carboxy, or alkoxy-carbonyl.

In one embodiment, phenyl is a preferred aryl group, which when "substituted" independently comprises hydroxyl, halogen, alkyl, or aryl groups attached directly or through an ether linkage. Where the phenyl ring is so substituted, the amino acid residue may be referred to as substituted, as in substituted Phe, substituted HPhe or substituted Pgl.

"Heteroaryl Group"

As used herein, the term "heteroaryl group" means a monocyclic- or polycyclic aromatic ring comprising carbon atoms, hydrogen atoms, and one or more heteroatoms, preferably 1 to 4 heteroatoms, independently selected from nitrogen, oxygen, and sulfur. Illustrative examples of heteroaryl groups include, but are not limited to, pyridyl, pyridazinyl, pyrazyl, indolyl, triazinyl, pyrrolyl, pyrazolyl, imidazolyl, (1,2,3,)-triazolyl, (1,2,4)-triazolyl, pyrazinyl, pyrimidinyl, tetrazolyl, furyl, thienyl, isoxazolyl, thiazolyl, thiadiazolyl, furyl, phenyl, isoxazolyl, oxazolyl, pyrazolyl, tetrazolyl, triazolyl, oxadiazolyl, thiadiazolyl, isoxazolyl, triazinyl, and pyrazinyl. Bicyclic heteroaromatic rings include, but are not limited to, benzothiadiazolyl, indolyl, benzothiophenyl, benzofuryl, benzimidazolyl, benzisoxazolyl, benzothiazolyl, quinolinyl, benzotriazolyl, benzoxazolyl, isoquinolinyl, purinyl, furopyridinyl and thienopyridinyl. A heteroaryl can be unsubstituted or optionally substituted with one or two suitable substituents as defined below. A heteroaryl group optionally may be fused to another heteroaryl group, fused to an aryl group, fused to a cycloalkyl group, or fused to a heterocycloalkyl group.

"Cycloalkyl Group"

As used herein, the term "cycloalkyl group" means a monocyclic or polycyclic saturated ring comprising carbon and hydrogen atoms and having no carbon-carbon multiple bonds. Examples of cycloalkyl groups include, but are not limited to, ($C_3$-$C_7$) cycloalkyl groups, such as cyclopropyl, cyclobutyl, cyclopentyl, cyclohexyl, and cycloheptyl, and saturated cyclic and bicyclic terpenes. A cycloalkyl group can be unsubstituted or optionally substituted with one or two suitable substituents as defined below. A cycloalkyl group optionally may be fused to another cycloalkyl group, fused to an aryl group, fused to a heteroaryl group, or fused to a heterocycloalkyl group.

"Heterocycloalkyl Group"

As used herein, the term "heterocycloalkyl group" means a monocyclic or polycyclic ring comprising carbon and hydrogen atoms and at least one heteroatom, preferably, 1 to 3 heteroatoms selected from nitrogen, oxygen, and sulfur. A heterocycloalkyl group may be fused to an aryl or heteroaryl group. Examples of heterocycloalkyl groups include, but are not limited to, pyrrolidinyl, pyrrolidino, piperidinyl, piperidino, piperazinyl, piperazino, morpholinyl, morpholino, thiomorpholinyl, thiomorpholino, and pyranyl. A heterocycloalkyl group can be unsubstituted or optionally substituted with one or two suitable substituents as defined below. A heterocycloalkyl group optionally may be fused to a cycloalkyl group, fused to an aryl group, fused to a heteroaryl group, or fused to another heterocycloalkyl group.

For example, a heterocycloalkyl group can be fused to or substituted with an aryl group or heteroaryl group, for example, but not limited to, 1,2,3,4-tetrahydroisoquinolinyl and 1,2,3,4-tetrahydroquinolinyl, tetrahydronaphthyridinyl, phenylpiperidinyl, and piperidinylpyridinyl.

In a preferred embodiment, a heterocycloalkyl group is a monocyclic or bicyclic ring, more preferably, a monocyclic ring, wherein the ring comprises from 3 to 6 carbon atoms and form 1 to 3 heteroatoms, referred to herein as ($C_3$-$C_6$) heterocycloalkyl. In another preferred embodiment, a heterocycloalkyl group is fused to or substituted with an aryl group or a heteroaryl group.

"Heterocyclic Radical" or "Heterocyclic Ring"

As used herein, the terms "heterocyclic radical" or "heterocyclic ring" mean a heterocycloalkyl group or a heteroaryl group.

"Cyclic Radical"

As used herein, the term "cyclic radical" means an aryl group, a cycloalkyl group, a heterocycloalkyl group or a heteroaryl group.

"Alkoxy"

As used herein, the term "alkoxy" means an —O-alkyl group, wherein alkyl is as defined above. An alkoxy group can be unsubstituted or optionally substituted with one or two suitable substituents. Preferably, the alkyl chain of an alkyloxy group is from 1 to 6 carbon atoms in length, referred to herein as "($C_1$-$C_6$) alkoxy".

"Aryloxy"

As used herein, the term "aryloxy" means an —O-aryl group, wherein aryl is as defined above. An aryloxy group can be unsubstituted or optionally substituted with one or two suitable substituents. Preferably, the aryl ring of an aryloxy group is a monocyclic ring, wherein the ring comprises 6 carbon atoms, referred to herein as "($C_6$)aryloxy".

"Alkoxycarbonyl"

As used herein, the term "alkoxycarbonyl" group means a monovalent group of the formula —C(=O)-alkoxy. Preferably, the hydrocarbon chain of an alkoxycarbonyl group is from 1 to 8 carbon atoms in length, referred to herein as a "lower alkoxycarbonyl" group.

"Carbamoyl"

As used herein, the term "carbamoyl" group means the radical —C(=O)N(R')$_2$, wherein R' is chosen from the group consisting of hydrogen, alkyl, and aryl.

"Carbonyl"

As used herein, a "carbonyl" group is a divalent group of the formula C(=O).

"Oxo"

As used herein, an "oxo" group is a group of the formula (=O).

"Acyl"

The term "acyl" includes a group R—C(=O)—, where R is an organic group. An example is the acetyl group $CH_3$—C(=O)—, referred to herein as "Ac". A peptide or aliphatic moiety is "acylated" when an aryl, alkyl or substituted alkyl group as defined above is bonded through one or more carbonyl {—(C=O)—} groups. A peptide is most usually acylated at the N-terminus.

"Amide"

An "amide" includes compounds that have a trivalent nitrogen attached to a carbonyl group (—C(=O)—NH$_2$), such as for example methylamide, ethylamide, propylamide, and the like.

"Imide"

An "imide" includes compounds containing an imido group (—C(=O)—NH—C(=O)—).

"Amine"

An "amine" includes compounds that contain an amino group (—NH$_2$).

"Nitrile"

A "nitrile" includes compounds that are carboxylic acid derivatives and contain a (—CN) group bound to an organic group.

"Halogen"

As used herein, the term "halogen" means fluorine, chlorine, bromine, or iodine. Correspondingly, the meaning of the terms "halo" and "Hal" encompass fluoro, chloro, bromo, and iodo.

"Sulfonamide"

As used herein, the term "sulfonamide" means compounds of the formula —R—S(=O)$_2$—NH$_2$ where R any organic group, including but not limited to alkyl.

"Peptide Solid Support"

As used herein, the term "peptide solid support" means a synthetic polymer for use in peptide synthesis that bears reactive groups (free hydroxyl or amino groups), generally through a linker, that can react with the carboxyl group of an N-protected amino acid functionality or a surrogate of formula I, thereby covalently binding the amino acid or surrogate of formula I to the polymer. At the end of the peptide synthesis, the bond between the C-terminal amino acid or surrogate and the polymer support can be chemically cleaved. The peptide or compound including one or surrogates of formula I then goes into solution and can be isolated from the solution. Examples of peptide solid supports include, but are not limited to, polyamide resins and polystyrene resins with a suitable linker for solid phase synthesis. Examples of resins include Merrifield resins, BHA resins, MBHA resins, Wang resins, oxime resins and the like. Linkers that may be employed include Fmoc-Rink, Sieber linker, Weinreb linker, and the like.

"Nitrogen Protecting Group"

As used herein, the term "nitrogen protecting group" means a group that replaces an amino hydrogen for the purpose of protecting against side reactions and degradation during a reaction sequence, for example, during peptide synthesis. Solid phase peptide synthesis involves a series of reaction cycles comprising coupling the carboxy group of an N-protected amino acid or surrogate with the amino group of the peptide substrate, followed by chemically cleaving the nitrogen protecting group so that the next amino-protected synthon may be coupled. Nitrogen protecting groups useful in the invention include nitrogen protecting groups well known in solid phase peptide synthesis, including, but not limited to, tert-butyloxycarbonyl (Boc), 9-flourenylmethyloxycarbonyl (Fmoc), 2-chlorobenzyloxycarbonyl, allyloxycarbonyl (alloc), benzyloxycarbonyl (Z), 2-(4-biphenylyl)propyl-2-oxycarbonyl (Bpoc), 1-adamantyloxycarbonyl, triphenylmethyl (trityl), and toluene sulphonyl.

"Suitable Substituent"

As used herein, the term "suitable substituent" means a group that does not nullify the synthetic, therapeutic or pharmaceutical utility of the compounds of the invention or the intermediates useful for preparing them. Examples of suitable substituents include, but are not limited to: alkyl; haloalkyl; cycloalkyl; alkoxy; alkylthio; halo; nitro; acyl; cyano; aryl; alkylaryl; aryloxy; amino; monosubstituted amino; disubstituted amino; sulfonamide; hydroxyl; carboxy; alkoxy-carbonyl; alkenyl; alkynyl; heteroaryl; heterocycloalkyl; O-alkenyl; O-alkynyl; oxo; $CF_3$; $NO_2$; $NH_2$; NH(alkyl); N(alkyl)$_2$; NH(aryl); N(aryl)$_2$; C(=O)NH$_2$; C(=O)NH(alkyl); C(=O)N(alkyl)$_2$; C(=O)NH(aryl); C(=O)N(aryl)$_2$; OC(=O)NH$_2$; C(=O)NH(heteroaryl); C(=O)N(heteroaryl)$_2$; C(=O)NH(aralkyl); C(=O)N(aralkyl)$_2$; OC(=O)NH(alkyl); OC(=O)N(alkyl)$_2$; OC(=O)NH(aryl); OC(=O)N(aryl)$_2$; OC(=O)NH(aralkyl); OC(=O)N(aralkyl)$_2$; C(=O)(alkyl); C(=O)(aryl); C(=O)(aralkyl); C(=O)O(alkyl); C(=O)O(aryl); C(=O)O(aralkyl); OC(=O)(alkyl); OC(=O)(aryl); OC(=O)(aralkyl); OC(=O)O(alkyl); OC(=O)O(aryl); OC(=O)O(aralkyl); S-alkyl; S-alkenyl; S-alkynyl; S(=O)$_2$-aryl, S(=O)$_2$-alkyl; S(=O)$_2$-alkenyl; S(=O)$_2$-alkynyl; S(=O)$_2$aralkyl; and S(=O)$_2$-aryl. One of skill in art can readily choose a suitable substituent based on the synthesis, stability and pharmacological activity of the compound of the invention.

The "〜〜〜〜"

As used herein in the chemical structure drawings, the above "wavy line" indicates a bond at the point that a chemical group is attached to another chemical group. Thus, according to this definition, the chemical formula "A" below:

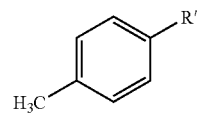

A wherein R' is a group of the formula "B",

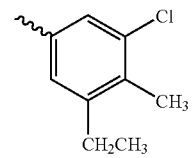

B represents the compound below

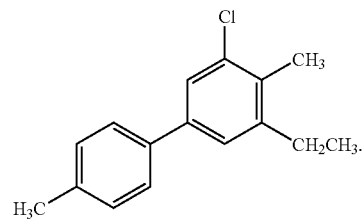

The "———"

As used herein in the chemical structure drawings, the above "solid line" when drawn across a bond line indicates an active chemical bond, such as a bond attaching one chemical group to another chemical group, without specify the other chemical group. Thus, according to this definition,

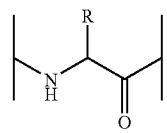

represents an isolated amino acid residue with an R amino acid side chain moiety wherein the isolated residue forms a bond to an unspecified chemical group at each of the N terminal and C terminal.

"Composition"

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a peptidomimetic of the present invention and a pharmaceutically acceptable carrier.

"$EC_{50}$"

The term "$EC_{50}$" is intended to include the molar concentration of an agonist which produced 50% of the maximum possible response for that agonist. By way of example, a compound which, at a concentration of 72 nM, produces 50% of the maximum possible response for that compound as determined in a cAMP assay, has an $EC_{50}$ of 72 nM. Unless otherwise specified, the molar concentration associated with an $EC_{50}$ determination is in nanomoles (nM).

"Ki (nM)"

The term "Ki (nM)" is intended to include the equilibrium receptor binding affinity representing the molar concentration of a competing compound that binds to half the binding sites of a receptor at equilibrium in the absence of a competitor. In general, the Ki is inversely correlated to the affinity of the compound for the receptor, such that if the Ki is low, the affinity is high. Ki may be determined using the equation of Cheng and Prusoff (Cheng Y., Prusoff W. H., *Biochem. Pharmacol.* 22: 3099-3108, 1973):

$$Ki = \frac{IC_{50}}{1 + \frac{[\text{ligand}]}{K_d}}$$

where "ligand" is the concentration of ligand, which may be a radioligand, and $K_d$ is an inverse measure of receptor affinity which produces 50% receptor occupancy. Unless otherwise specified, the molar concentration associated with a Ki determination is nM. $IC_{50}$ is the concentration of ligand at which 50% of receptor-bound radioligand or other ligand is displaced from the receptor sites in a competitive receptor binding displacement assay.

"Peptide"

The term "peptide" as used throughout the specification and claims is intended to include any structure comprised of two or more amino acids, including chemical modifications and derivatives of amino acids. The amino acids forming all or a part of a peptide may be naturally occurring amino acids, stereoisomers and modifications of such amino acids, non-protein amino acids, post-translationally modified amino acids, enzymatically modified amino acids, and the like. The term "peptide" also includes dimers or multimers of peptides. A "manufactured" peptide includes a peptide produced by chemical synthesis, recombinant DNA technology, biochemical or enzymatic fragmentation of larger molecules, combinations of the foregoing or, in general, made by any other method.

"Peptidomimetic"

The term "peptidomimetic" as used throughout the specification and claims is intended to include any structure comprised of two or more amino acids, including chemical modifications and derivatives of amino acids and at least one "surrogate" as hereafter defined. The amino acids forming all or a part of a peptidomimetic may be naturally occurring amino acids, stereoisomers and modifications of such amino acids, non-protein amino acids, post-translationally modified amino acids, enzymatically modified amino acids, and the like. The term "peptidomimetic" also includes dimers or multimers of peptidomimetic. A "manufactured" peptidomimetic includes a peptidomimetic produced by chemical synthesis, recombinant DNA technology, biochemical or enzymatic fragmentation of larger molecules, combinations of the foregoing or, in general, made by any other method.

"Amino Acid Side Chain Moiety"

The term "amino acid side chain moiety" used in this invention, including as used in the specification and claims, includes any side chain of any amino acid, as the term "amino acid" is defined herein. This thus includes the side chain moiety present in naturally occurring amino acids. It further includes side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like. For example, the side chain moiety of any amino acid disclosed herein is included within the definition. A "derivative of an amino acid side chain moiety" as hereafter defined is included within the definition of an amino acid side chain moiety.

"Derivative of an Amino Acid Side Chain Moiety"

A "derivative of an amino acid side chain moiety" is a modification to or variation in any amino acid side chain moiety, including a modification to or variation in either a naturally occurring or unnatural amino acid side chain moiety, wherein the modification or variation includes: (a) adding one or more saturated or unsaturated carbon atoms to an existing alkyl, aryl, or aralkyl chain; (b) substituting a carbon in the side chain with another atom, preferably oxygen or nitrogen; (c) adding a terminal group to a carbon atom of the side chain, including methyl (—$CH_3$), methoxy (—$OCH_3$), nitro (—$NO_2$), hydroxyl (—OH), or cyano (—C≡N); (d) for side chain moieties including a hydroxy, thio or amino groups, adding a suitable hydroxy, thio or amino protecting group; or (e) for side chain moieties including a ring structure, adding one or more ring substituents, including hydroxyl, halogen, alkyl, or aryl groups attached directly or through an ether linkage. For amino groups, suitable amino protecting groups include, but are not limited to, Z, Fmoc, Boc, Pbf, Pmc and the like.

"Amino Acids"

The "amino acids" used in embodiments of the present invention, and the term as used in the specification and claims, include the known naturally occurring protein amino acids, which are referred to by both their common three letter abbreviation and single letter abbreviation. See generally *Synthetic Peptides: A User's Guide*, G. A. Grant, editor, W.H. Freeman & Co., New York (1992), the teachings of which are incorporated herein by reference, including the text and table set forth at pages 11 through 24. An "amino acid" includes conventional α-amino acids and further includes both β-amino acids and α,α-disubstituted amino acids wherein at least one side chain is an amino acid side chain moiety as defined herein. An "amino acid" further includes N-alkyl α-amino acids, wherein the N-terminus amino group has a $C_1$ to $C_6$ linear or branched alkyl substituent. It may thus be seen that the term "amino acid" includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V. J., Al-obeidi F., Kazmierski W., *Biochem. J.* 268: 249-262 (1990); and Toniolo C., *Int. J. Peptide Protein Res.* 35:287-300 (1990); the teachings of all of which are incorporated herein by reference. In addition, the following abbreviations, including amino acids and protecting and modifying groups thereof, have the meanings given:

| | |
|---|---|
| Abu | gamma-amino butyric acid |
| 12-Ado | 12-amino dodecanoic acid |
| Aib | alpha-aminoisobutyric acid |
| 6-Ahx | 6-amino hexanoic acid |
| Amc | 4-(aminomethyl)-cyclohexane carboxylic acid |
| 8-Aoc | 8-amino octanoic acid |
| Bip | biphenylalanine |
| Bzl | benzyl |
| Bz | benzoyl |
| Dab | diaminobutyric acid |
| Dap | diaminopropionic acid |
| Dip | 3,3-diphenylalanine |
| Disc | 1,3-dihydro-2H-isoindolecarboxylic acid |
| Et | ethyl |
| Hept | heptanoyl ($CH_3$—$(CH_2)_5$—C(=O)—) |
| Hex | hexanoyl ($CH_3$—$(CH_2)_4$—C(=O)—) |
| HArg | homoarginine |
| HCys | homocysteine |
| HLys | homolysine |
| HPhe | homophenylalanine |
| HSer | homoserine |
| Me | methyl |
| Met(O) | methionine sulfoxide |
| Met($O_2$) | methionine sulfone |
| Nva | norvaline |
| Pgl | phenylglycine |
| Pr | propyl |
| Pr-i | isopropyl |
| Sar | sarcosine |
| Tle | tert-butylalanine |

In the listing of compounds according to the present invention, conventional amino acid residues have their conventional meaning as given in Chapter 2400 of the *Manual of Patent Examining Procedure*, 8th Ed. Thus, "Nle" is norleucine; "Asp" is aspartic acid; "His" is histidine; "Arg" is arginine; "Trp" is tryptophan; "Lys" is lysine; "Gly" is glycine; "Pro" is proline; "Tyr" is tyrosine, "Ser" is serine and so on. All residues are in the L-isomer configuration unless the D-isomer is specified, as in "D-Ala" for D-alanine.

A single amino acid, including stereoisomers and modifications of naturally occurring protein amino acids, non-protein amino acids, post-translationally modified amino acids, enzymatically synthesized amino acids, derivatized amino acids, an α,α-disubstituted amino acid derived from any of the foregoing (i.e., an α,α-disubstituted amino acid wherein at least one side chain is the same as that of the residue from which it is derived), a β-amino acid derived from any of the foregoing (i.e., a β-amino acid which other than for the presence of a β-carbon is otherwise the same as the residue from which it is derived) and the like, including all of the foregoing, is sometimes referred to herein as a "residue."

"α,α-Disubstituted Amino Acid"

An "α,α-disubstituted amino acid" means any α-amino acid having a further substituent in the α-position, which substituent may be the same as or different from the side chain moiety of the α-amino acid. Suitable substituents, in addition to the side chain moiety of the α-amino acid, include $C_1$ to $C_6$ linear or branched alkyl. Aib is an example of an α,α-disubstituted amino acid. While α,α-disubstituted amino acids can be referred to using conventional L- and D-isomeric references, it is to be understood that such references are for convenience, and that where the substituents at the α-position are different, such amino acid can interchangeably be referred to as an α,α-disubstituted amino acid derived from the L- or D-isomer, as appropriate, of a residue with the designated amino acid side chain moiety. Thus (S)-2-Amino-2-methyl-hexanoic acid can be referred to as either an α,α-disubstituted amino acid derived from L-Nle or as an α,α-disubstituted amino acid derived from D-Ala. Similarly, Aib can be referred to as an α,α-disubstituted amino acid derived from Ala. Whenever an α,α-disubstituted amino acid is provided, it is to be understood as including all (R) and (S) configurations thereof.

"N-Substituted Amino Acid"

An "N-substituted amino acid" means any amino acid wherein an amino acid side chain moiety, including without limitation an alkyl, aryl or aralkyl group, is covalently bonded to the backbone amino group, including optionally where there are no substituents other than H in the α-carbon position. Sarcosine is an example of an N-substituted amino acid. By way of example, sarcosine can be referred to as an N-substituted amino acid derivative of Ala, in that the amino acid side chain moiety of sarcosine and Ala is the same, methyl. Similarly, MePhe is N-methyl phenylalanine.

"C-Terminus Group"

The term "C-terminus group" means any terminal group attached through the terminal ring carbon atom of a surrogate or terminal carbon atom of a residue or surrogate of the C-terminus of a peptidomimetic. The terminal ring carbon atom or terminal carbon atom may form a part of a residue or may form a part of a surrogate. In one aspect, the C-terminus group forms a part of an amino acid surrogate which is at the C-terminus position of the peptidomimetic. In another aspect, the C-terminus group forms a part of an amino acid residue which is at the C-terminus position of the peptidomimetic. The C-terminus group includes, but is not limited to,

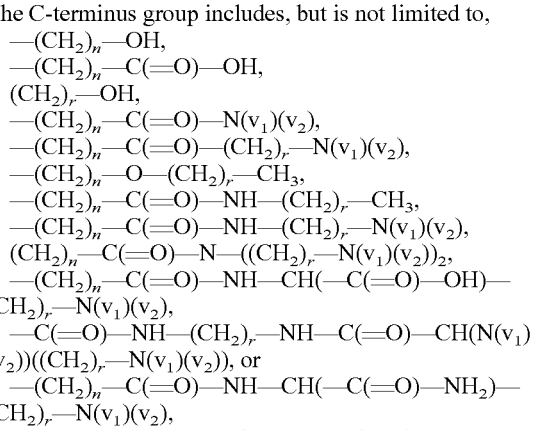

including all (R) or (S) configurations of the foregoing, where $v_1$ and $v_2$ are each independently H, a $C_1$ to $C_{17}$ linear or branched alkyl chain, r is 0 to 17 and n is 0 to 2; or any omega amino aliphatic, terminal aryl or aralkyl, including groups such as methyl, dimethyl, ethyl, propyl, isopropyl, butyl, isobutyl, pentyl, hexyl, allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7'-amino heptanoyl, 6-Ahx, Amc or 8-Aoc, or any single natural or unnatural α-amino acid, β-amino acid or α,α-disubstituted amino acid, including all (R) or (S) configurations of the foregoing, optionally in combination with any of the foregoing non-amino acid groups.

"N-Terminus Group"

The term "N-terminus group" means any terminal group attached through the terminal amine of the N-terminus of a peptidomimetic. The terminal amine may form a part of a residue or may form a part of an amino acid surrogate ring. In one aspect, the N-terminus group forms a part of an amino acid surrogate which is at the N-terminus position of the peptidomimetic. In another aspect, the N-terminus group forms a part of an amino acid residue which is at the N-terminus position of the peptidomimetic. The N-terminus group includes, but is not limited to, —(CH$_2$)$_r$—NH(v$_3$),
—(CH$_2$)$_r$—CH$_3$,
—C(=O)—(CH$_2$)$_r$—CH$_3$,
—C(=O)—(CH$_2$)$_r$—NH(v$_3$),
—C(=O)—(CH$_2$)$_r$—C(=O)—OH,
—C(=O)—(CH$_2$)$_r$—C(=O)—(v$_4$),
—(CH$_2$)$_r$—C(=O)—OH,
—(CH$_2$)$_r$—C(=O)—(v$_4$),
—C(=O)—(CH$_2$)$_r$—O(v$_3$),
—(CH$_2$)$_r$—O(v$_3$),
—C(=O)—(CH$_2$)$_r$—S(v$_3$), or
—(CH$_2$)$_r$—S(v$_3$), including all (R) or (S) configurations of the foregoing, where v$_3$ is H or a C$_1$ to C$_{17}$ linear or branched alkyl chain, v$_4$ is a C$_1$ to C$_{17}$ linear or branched alkyl chain and r is 0 to 17; or any omega amino aliphatic, acyl group or terminal aryl or aralkyl including groups such as methyl, dimethyl, ethyl, propyl, isopropyl, butyl, isobutyl, pentyl, hexyl, allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7'-amino heptanoyl, 6-Ahx, Amc or 8-Aoc, including all (R) or (S) configurations of the foregoing.

The chemical naming protocol and structure diagrams used herein employ and rely on the chemical naming features as utilized by the ChemDraw program (available from Cambridgesoft Corp.) or ISIS Draw (available from MDL Information Systems Inc.). In particular, certain compound names were derived from the structures using the Autonom program as utilized by Chemdraw Ultra or ISIS Draw. In general, structure diagrams do not depict hydrogen atoms other than in terminal groups and other special circumstances.

Certain peptidomimetics are depicted herein with the surrogates identified by structure diagrams and the amino acid residues identified by a three letter abbreviation. Unless otherwise specified, it is understood that the bond between the surrogate and residue, or between the residue and surrogate, or between a surrogate and residues on both the N-terminus and C-terminus side thereof, is a conventional peptide bond, —C(=O)—NH— or, in the case where the peptide bond is to the ring nitrogen on the N-terminus of the surrogate, —C(=O)—N—. In general, in the depiction of such bonds the atoms of the amino acid surrogate are depicted (e.g., —C(=O)— or —N), but atoms of the amino acid residue are not depicted.

2. Surrogates Employed in Peptidomimetics of the Invention

The invention employs ring-constrained amino acid surrogates of the formula I and linear or cyclic peptidomimetics comprising ring-constrained amino acid surrogates of formula I:

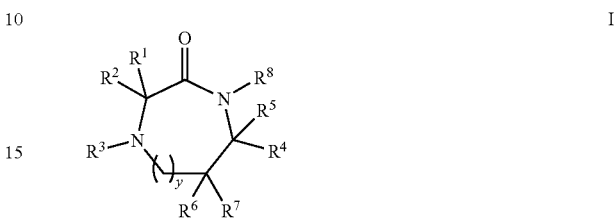

or an enantiomer, stereoisomer or diastereoisomer thereof, or a synthetically acceptable salt thereof, wherein:

R$^1$ is H, alkyl, aryl, alkylaryl, alkyl-N(R$^9$)$_2$, alkyl-OR$^9$, alkyl-C(=O)OR$^9$, C(=O)OR$^9$, alkyl-S—R$^9$, alkyl-C(=O)N(R$^9$)$_2$, or a group of a formula:

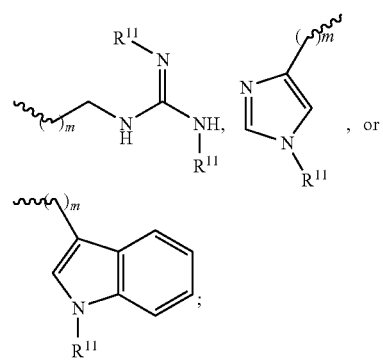

R$^2$ is H or alkyl;

R$^3$ is H or a first nitrogen protecting group;

R$^4$ is H, alkyl, (CH$_2$)$_m$C(=O)OH, (CH$_2$)$_m$C(=O)NR$^{10}$, (CH$_2$)$_m$C(=O)OR$^{10}$, (CH$_2$)$_q$OH, (CH$_2$)$_q$OBn, (CH$_2$)$_q$Oallyl, (CH$_2$)$_m$C(=O)N(R$^9$)$_2$, or (CH$_2$)$_m$C(=O)N(R$^9$)(CH$_2$)$_p$N(R$^9$)$_2$;

R$^5$ is H or alkyl;

R$^6$ is H, alkyl, (CH$_2$)$_m$C(=O)OH, (CH$_2$)$_m$C(=O)NR$^{10}$, (CH$_2$)$_m$C(=O)OR$^{10}$, (CH$_2$)$_q$OH, (CH$_2$)$_q$OBn, (CH$_2$)$_q$Oallyl, (CH$_2$)$_m$C(=O)N(R$^9$)$_2$, or (CH$_2$)$_m$C(=O)N(R$^9$)(CH$_2$)$_p$N(R$^9$)$_2$;

R$^7$ is H or alkyl;

provided that both of R$^4$ and R$^6$ are not (CH$_2$)$_m$C(=O)OH, (CH$_2$)$_m$C(=O)NR$^{10}$, (CH$_2$)$_m$C(=O)OR$^{10}$, (CH$_2$)$_q$OH, (CH$_2$)$_q$OBn, (CH$_2$)$_q$Oallyl, (CH$_2$)$_m$C(=O)N(R$^9$)$_2$, or (CH$_2$)$_m$C(=O)N(R$^9$)(CH$_2$)$_p$N(R$^9$)$_2$;

R$^8$ is H, C(=O)alkyl, C(=O)(CH$_2$)$_m$(NR$^9$)$_2$, alkyl, aralkyl, or aryl;

each occurrence of R$^9$ is independently H, aryl, or alkyl;

R$^{10}$ is a peptide solid support or one or more amino acid residues;

R$^{11}$ is H or a second nitrogen protecting group;

each occurrence of m is an independent integer having a value between 0 and 6;

each occurrence of q is an independent integer having a value between 1 and 6;

p is an integer having a value between 1 and 10; and y is 0 or 1.

Ring-constrained amino acid surrogates of the formula I may be employed for substitution of one or more amino acid residues of peptidomimetics of the invention made of a plurality of amino acid residues.

The ring-constrained amino acid surrogate of formula I is preferably such that it may be made with a conventional amino protected N-terminus, using a protecting group such as Fmoc, and a reactive carboxyl C-terminus, and may thus be employed in conventional peptide synthesis methodologies. It is understood that if the amino acid surrogate of formula I is to be coupled at the C-terminus position of the peptidomimetic, other than a carboxyl terminus may be employed on such surrogate.

Thus in a preferred embodiment the invention provides ring-constrained amino acid surrogates for incorporation, by way of peptide synthesis methodologies, modified as appropriate, into peptidomimetics of the invention, which peptidomimetics comprise a plurality of amino acid residues.

Except where both $R^1$ and $R^2$ are H, it is to be appreciated that each surrogate employed in the invention can be in one of four different enantiomeric forms. Thus, by way of example, where the $R^1$ group is an amino acid side chain moiety of Arg, the compound may be generically shown as:

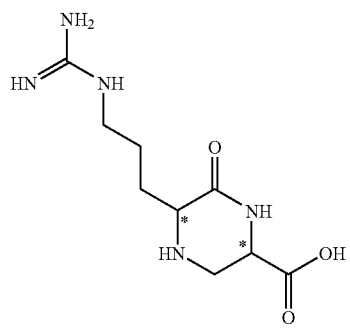

where each asterisk represents a chiral center which may be in any stereochemical configuration. Thus, it is to be understood that each of the following is possible, contemplated and intended:

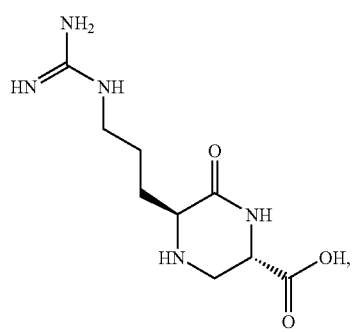

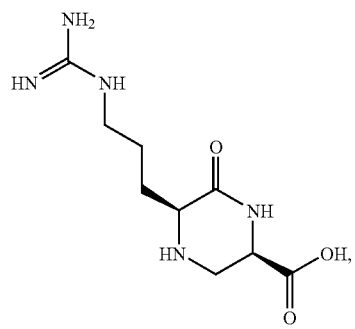

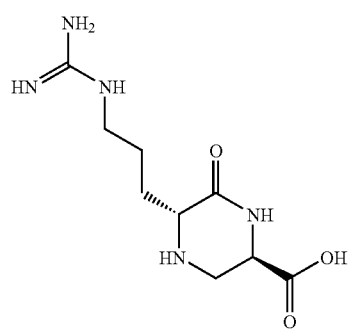

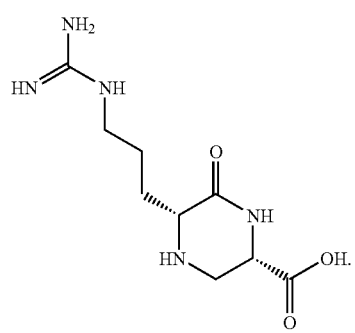

Similarly, with respect to each surrogate, for use in the synthesis of peptidomimetics using conventional peptide synthetic methodologies, it is understood that if a surrogate is other than at the N-terminal position that the $R^3$ position will include a nitrogen protecting group rather than H, and thus will be of the following general structure:

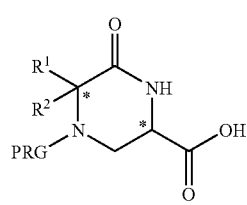

where PRG is a nitrogen protecting group, such as, by way of example and not limitation, a group of the formula:

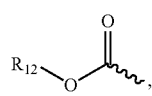

where $R^{12}$ is tert-butyl, allyl, or a group of a formula:

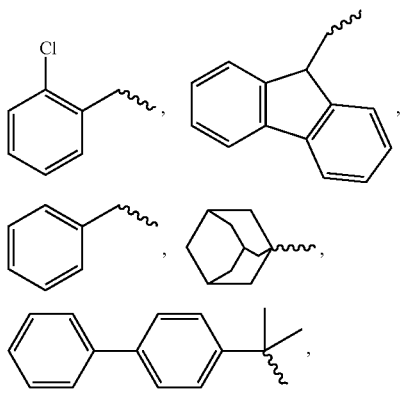

Thus it may be seen, in the example where the $R^1$ or $R^2$ group is an amino acid side chain moiety of Arg and $R^3$ is the nitrogen protecting group Fmoc, that each of the following is possible, contemplated and intended:

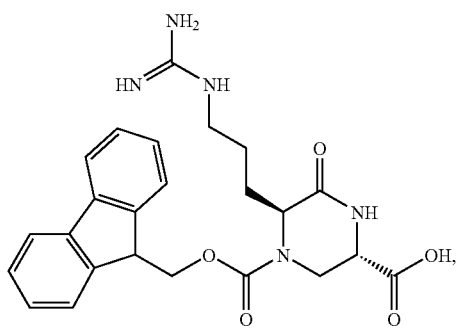

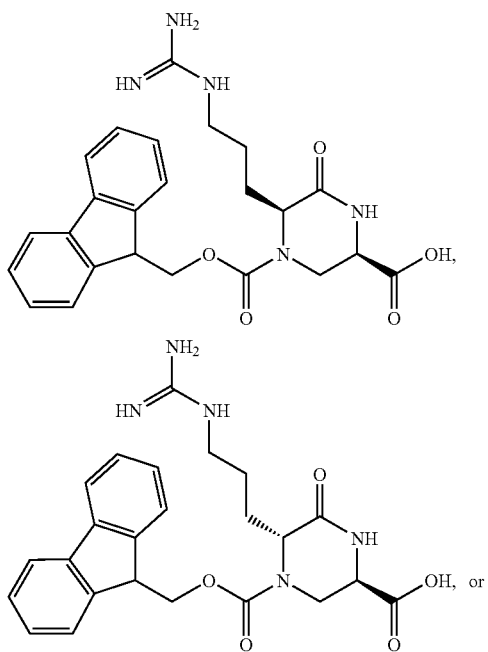

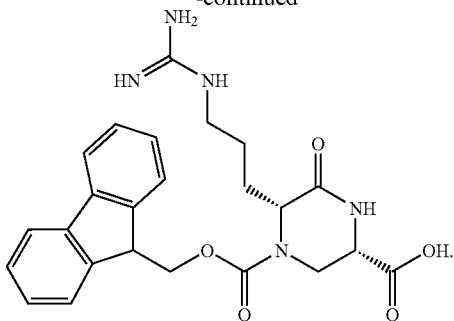

In the specific example above, it is also possible and contemplated that a nitrogen protecting group, such as for example Pbf, would be employed in the guanidino group. It may also be seen that analogous surrogates are possible and contemplated employing another group as the nitrogen protecting group or another amino acid side chain moiety or derivative of an amino acid side chain moiety as the $R^1$ or $R^2$ group, or alternatively, where at least one thereof is alkyl, aryl, alkylaryl, alkyl-N($R^9$)$_2$, alkyl-O$R^9$, alkyl-C(=O)O$R^9$, C(=O)O$R^9$, alkyl-S—$R^9$, alkyl-C(=O)N($R^9$)$_2$, or a group of a formula:

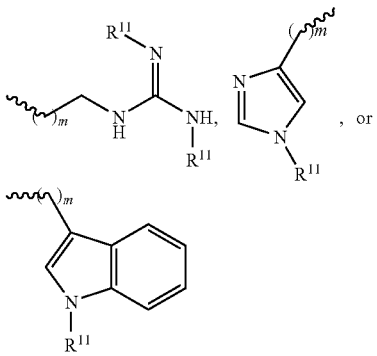

where $R^9$ is H, aryl, or alkyl and $R^{11}$ is H or a second nitrogen protecting group.

If a surrogate is employed in the synthesis of peptidomimetics using conventional peptide synthetic methodologies and is at the C-terminal position, then the surrogate may be a compound that is bonded to a peptide solid support, such as a resin. In this instance the surrogate may be of the following general structure:

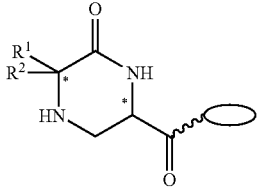

where the oval depicts resin and a linker or another peptide solid support. Here too the $R^1$ or $R^2$ group may be any amino acid side chain moiety or derivative of an amino acid side chain moiety, or alternatively, at least one thereof may be alkyl, aryl, alkylaryl, alkyl-N($R^9$)$_2$, alkyl-O$R^9$, alkyl-C(=O)O$R^9$, C(=O)O$R^9$, alkyl-S—$R^9$, alkyl-C(=O)N($R^9$)$_2$, or a group of a formula:

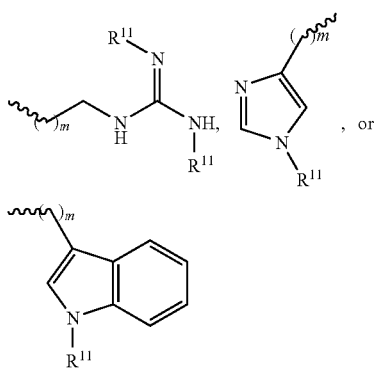

where $R^9$ is H, aryl, or alkyl and $R^{11}$ is H or a second nitrogen protecting group.

In one aspect, the invention thus employs surrogates of the following general structure:

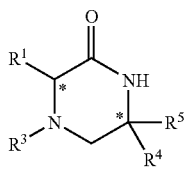

where $R^1$ is one of the following:

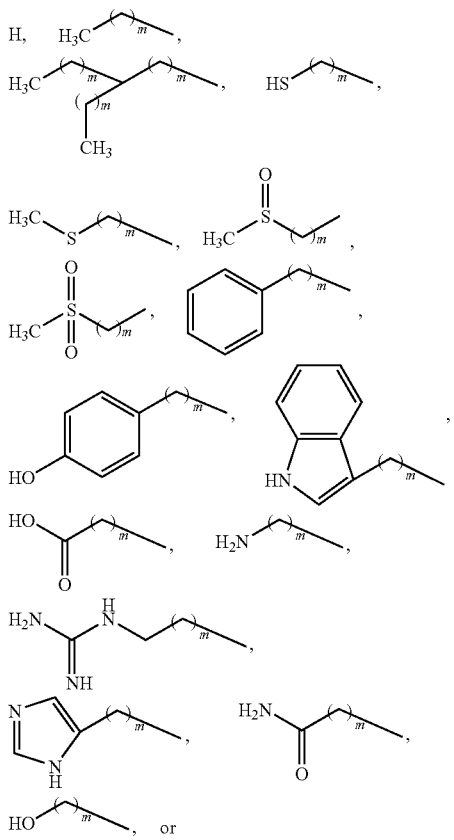

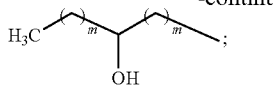

$R^3$ is H or a first nitrogen protecting group;

$R^4$ is H, alkyl, $(CH_2)_mC(\!\!=\!\!O)OH$, $(CH_2)_mC(\!\!=\!\!O)NR^{10}$, $(CH_2)_mC(\!\!=\!\!O)OR^{10}$, $(CH_2)_qOH$, $(CH_2)_qOBn$, $(CH_2)_qOal\text{-}lyl$, $(CH_2)_mC(\!\!=\!\!O)N(R^9)_2$, or $(CH_2)_mC(\!\!=\!\!O)N(R^9)(CH_2)_pN(R^9)_2$;

$R^5$ is H or alkyl;

$R^9$ is H, aryl, or alkyl;

$R^{10}$ is a peptide solid support;

each occurrence of m is an independent integer having a value between 0 and 6;

each occurrence of q is an independent integer having a value between 1 and 6;

p is an integer having a value between 1 and 10; and any aryl group may be substituted independently with one or more substituents selected from alkyl, haloalkyl, cycloalkyl, alkoxy, alkylthio, halo, nitro, acyl, cyano, amino, monosubstituted amino, disubstituted amino, hydroxy, carboxy, or alkoxy-carbonyl.

Thus in one aspect there are provided surrogates with an $R^1$ group which is an amino acid side chain moiety of one of the nineteen naturally-coded amino acid residues (omitting Pro), including the following where $R^1$ is as shown, $R^3$ is H, $R^4$ is —C(=O)OH, and $R^5$ is H:

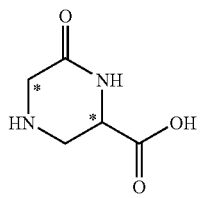
6-Oxo-piperazine-2-carboxylic acid

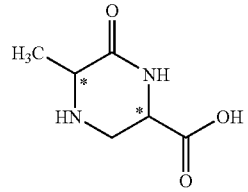
5-Methyl-6-oxo-piperazine-2-carboxylic acid

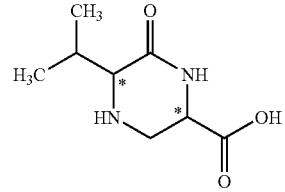
5-Isopropyl-6-oxo-piperazine-2-carboxylic acid

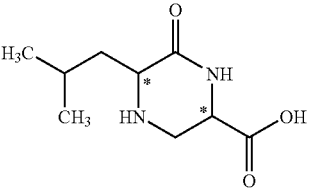
5-Isobutyl-6-oxo-piperazine-2-carboxylic acid

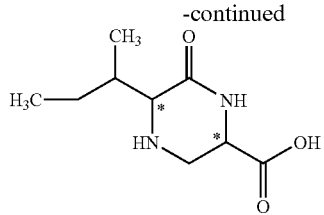

5-sec-Butyl-6-oxo-piperazine-2-carboxylic acid

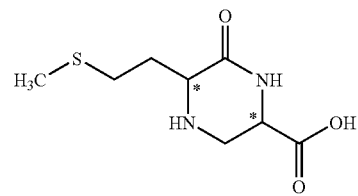

5-(2-Methylsulfanyl-ethyl)-6-oxo-piperazine-2-carboxylic acid

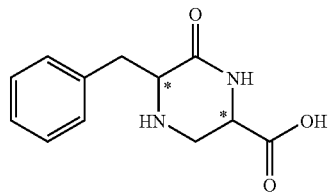

5-Benzyl-6-oxo-piperazine-2-carboxylic acid

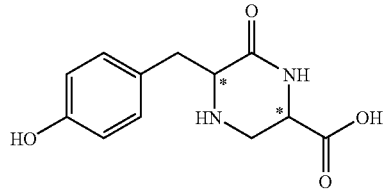

5-(4-Hydroxy-benzyl)-6-oxo-piperazine-2-carboxylic acid

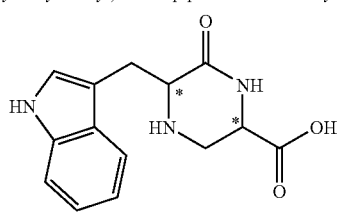

5-(1H-Indol-3-ylmethyl)-6-oxo-piperazine-2-carboxylic acid

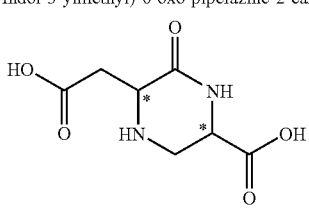

5-Carboxymethyl-6-oxo-piperazine-2-carboxylic acid

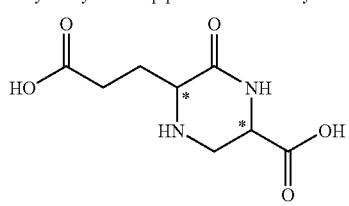

5-(2-Carboxy-ethyl)-6-oxo-piperazine-2-carboxylic acid

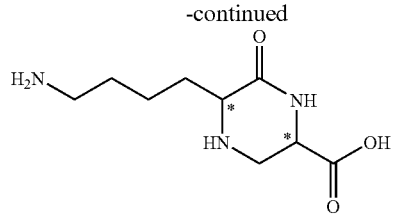

5-(4-Amino-butyl)-6-oxo-piperazine-2-carboxylic acid

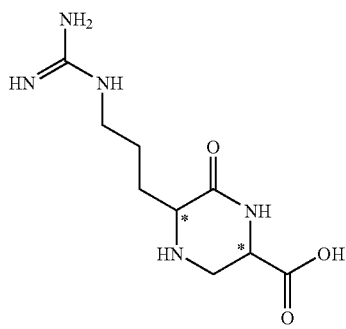

5-(3-Guanidino-propyl)-6-oxo-piperazine-2-carboxylic acid

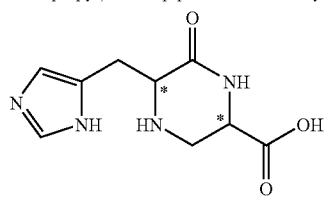

5-(3H-Imidazol-4-ylmethyl)-6-oxo-piperazine-2-carboxylic acid

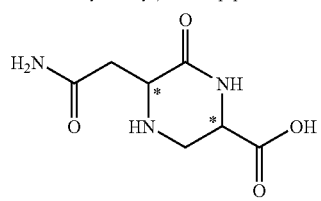

5-Carbamoylmethyl-6-oxo-piperazine-2-carboxylic acid

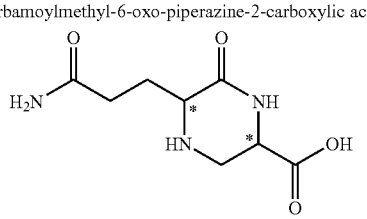

5-(2-Carbamoyl-ethyl)-6-oxo-piperazine-2-carboxylic acid

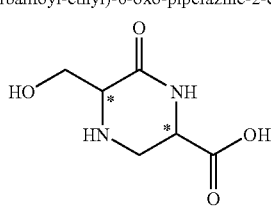

5-Hydroxymethyl-6-oxo-piperazine-2-carboxylic acid

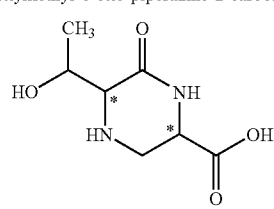

5-(1-Hydroxy-ethyl)-6-oxo-piperazine-2-carboxylic acid

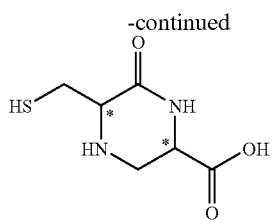

5-Mercaptomethyl-6-oxo-piperazine-2-carboxylic acid

It is also possible and contemplated to employ an $R^1$ group which is an amino acid side chain moiety of an amino acid residue other than a naturally-coded amino acid residue. By way of example, and not limitation, specifically included are amino acid side chain moieties of amino acid residues including Orn, HPhe, Abu, Apr, HArg, HSer and the like. In one aspect modifications may include varying the length of an $R^1$ aliphatic linear or branched chain. Thus in one example the $R^1$ group is an amino acid side chain moiety of norleucine:

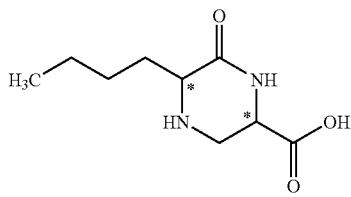

5-Butyl-6-oxo-piperazine-2-carboxylic acid

However, as set forth above the $R^1$ group may similarly be —$CH_3$, —$CH_2$—$CH_3$, —$(CH_2)_2$—$CH_3$, —$(CH_2)_3$—$CH_3$, —$(CH_2)_4$—$CH_3$, —$(CH_2)_5$—$CH_3$, or —$(CH_2)_6$—$CH_3$.

Similarly, any $R^1$ group may include one or more substituents. Thus in one example the $R^1$ group is an amino acid side chain moiety of phenylalanine where the phenyl ring is substituted with one or more substituents, including hydroxyl, halogen, alkyl, or aryl groups attached directly or through an ether linkage.

In each of the foregoing, rather than H in the $R^3$ position there may be any nitrogen protecting group; rather than —C(=O)OH the $R^4$ position may be alkyl, $(CH_2)_mC(=O)OH$, $(CH_2)_mC(=O)NR^{10}$, $(CH_2)_mC(=O)OR^{10}$, $(CH_2)_qOH$, $(CH_2)_qOBn$, $(CH_2)_qOallyl$, $(CH_2)_mC(=O)N(R^9)_2$, or $(CH_2)_m C(=O)N(R^9)(CH_2)_pN(R^9)_2$ where $R^9$ is H, aryl, or alkyl, $R^{10}$ is a peptide solid support, m is an independent integer having a value between 0 and 6, q is an independent integer having a value between 1 and 6 and p is an integer having a value between 1 and 10; and rather than H the $R^5$ position may be alkyl. Similarly, rather than one of the foregoing amino acid side chain moieties, $R^1$ may be alkyl, aryl, alkylaryl, alkyl-$N(R^9)_2$, alkyl-$OR^9$, alkyl-$C(=O)OR^9$, $C(=O)OR^9$, alkyl-$S$—$R^9$, alkyl-$C(=O)N(R^9)_2$, or a group of a formula:

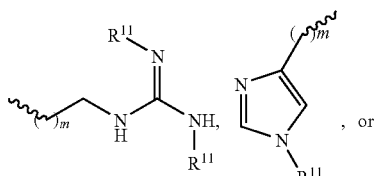

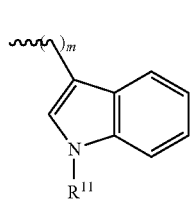

where $R^9$ is H, aryl, or alkyl and $R^{11}$ is H or a second nitrogen protecting group.

3. Isomeric Purity and Isolation

The surrogates employed in peptidomimetics of the invention can contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the peptidomimetics of the invention, encompass the racemic form of surrogates as well as all enantiomers and stereoisomers, that is, both the stereomerically pure form (e.g., geometrically pure, enantiomerically pure, or diastereomerically pure) and enantiomeric and stereoisomeric mixtures.

A surrogate is considered optically active or enantiomerically pure (i.e., substantially the R-form or substantially the S-form) with respect to a chiral center when the compound is about 90% ee (enantiomeric excess) or greater, preferably, equal to or greater than 95% ee with respect to a particular chiral center. A peptidomimetic of the invention is considered to be in enantiomerically enriched form when the peptidomimetic has an enantiomeric excess of greater than about 80% ee, preferably greater than about 85% ee. As used herein, a racemic mixture means about 50% of one enantiomer and about 50% of its corresponding enantiomer relative to all chiral centers in the molecule. Thus, the invention encompasses all enantiomerically pure, enantiomerically enriched, and racemic mixtures of peptidomimetics of the invention.

Thus in one aspect, the surrogate has the general structure:

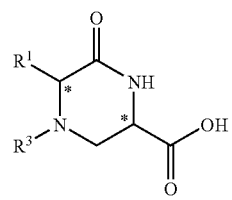

where the asterisk indicates any possible stereochemical conformation. This thus includes the following enantiomeric forms:

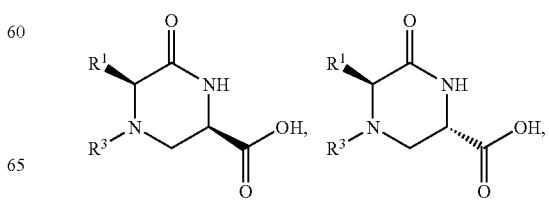

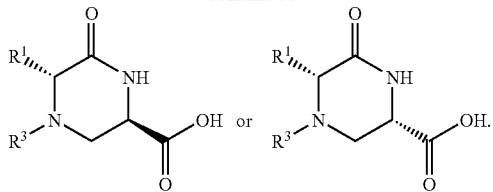

Enantiomeric and stereoisomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically- or enantiomerically-pure intermediates, reagents, and catalysts by well known asymmetric synthetic methods.

4. Peptidomimetics of the Invention

In accordance with one aspect of the present invention there are provided peptidomimetics which are specific for one or more melanocortin receptors, and are partial or full agonists, partial or full antagonists, mixed agonist-antagonists, inverse agonists, or antagonists of inverse agonists of specific melanocortin receptors, including MC1-R, MC3-R, MC4-R or MC5-R and subtypes thereof. The peptidomimetics comprise amino acid sequences selected from peptides that are specific for one or more melanocortin receptors, but which have one or amino acid residues substituted with a surrogate. If the peptidomimetic comprises more than one surrogate, the surrogates comprising the peptidomimetic are non-adjacent, such that one or more amino acid residues are interposed between surrogates. The peptidomimetics may be linear or cyclic. If cyclic, the surrogate(s) may be within the cyclic ring, may be employed to cyclize the ring, or may be outside the cyclic ring, such as comprising all or a portion of an N-terminus or C-terminus sequence outside the cyclic ring.

In one aspect of the present invention, the peptidomimetic comprises His-Phe-Arg-Trp (SEQ ID NO:1) or His-D-Phe-Arg-Trp, and one or more surrogates at either the N-terminus or C-terminus side of the sequence, or both, and optionally one or more amino acid residues at either the N-terminus or C-terminus side of the sequence, or both. This includes, by way of example and not limitation, peptidomimetics such as:

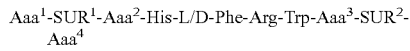

where $Aaa^1$ is H, an N-terminus group, or from 1 to about 3 L- or D-amino acids or combinations thereof, optionally with an N-terminus group; $SUR^1$ is absent or a surrogate of formula I; $Aaa^2$ and $Aaa^3$ are independently absent or from 1 to about 3 L- or D-amino acids or combinations thereof; L/D-Phe is Phe or D-Phe; $SUR^2$ is absent or a surrogate of formula I, on the proviso that at least one of $SUR^1$ and $SUR^2$ is not absent; and $Aaa^4$ is absent, a C-terminus group, or from 1 to about 3 L- or D-amino acids or combinations thereof, optionally with a C-terminus group. The peptidomimetic may be linear or cyclic, and if cyclic, is cyclized between a reactive chemical group of $Aaa^1$-$SUR^1$-$Aaa^2$ and a reactive chemical group of $Aaa^3$-$SUR^2$-$Aaa^4$. The cyclic bond may include an N-terminus group, a C-terminus group, an R group of $SUR^1$ or $SUR^2$, if provided, or one or two amino acid side chain moieties. The cyclic bond may include a covalent bond such as an amide, disulfide, thioether, Schiff base, reduced Schiff base, imide, secondary amine, carbonyl, urea, hydrazone or oxime bond.

In another aspect of the present invention, the peptidomimetic comprises a sequence wherein a surrogate of formula I substitutes for at least one of His, D/L-Phe, Arg or Trp in the sequence His-Phe-Arg-Trp (SEQ ID NO: 1) or His-D-Phe-Arg-Trp, and optionally one or more surrogates or amino acid residues, or both, at either the N-terminus or C-terminus side of the sequence, or both, and optionally one or more amino acid residues at either the N-terminus or C-terminus side of the sequence, or both. This includes, by way of example and not limitation, peptidomimetics such as:

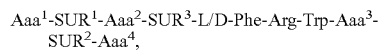

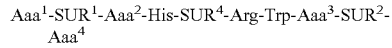

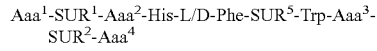

or

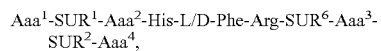

where $Aaa^1$ is H, an N-terminus group, or from 1 to about 3 L- or D-amino acids or combinations thereof, optionally with an N-terminus group; $SUR^1$ is absent or a surrogate of formula I; $Aaa^2$ and $Aaa^3$ are independently absent or from 1 to about 3 L- or D-amino acids or combinations thereof; L/D-Phe is Phe or D-Phe; $SUR^2$ is absent or a surrogate of formula I; $Aaa^4$ is absent, a C-terminus group, or from 1 to about 3 L- or D-amino acids or combinations thereof, optionally with a C-terminus group; $SUR^3$ is a surrogate of formula I wherein one of $R^1$ or $R^2$ is an amino acid side chain moiety of His or a derivative of an amino acid side chain moiety of His; $SUR^4$ is a surrogate of formula I wherein one of $R^1$ or $R^2$ is an amino acid side chain moiety of L- or D-Phe or a derivative of an amino acid side chain moiety of L- or D-Phe; $SUR^5$ is a surrogate of formula I wherein one of $R^1$ or $R^2$ is an amino acid side chain moiety of Arg a derivative of an amino acid side chain moiety of Arg, or alkylamine; and $SUR^6$ is a surrogate of formula I wherein one of $R^1$ or $R^2$ is an amino acid side chain moiety of Trp or a derivative of an amino acid side chain moiety of Trp. The peptidomimetic may be linear or cyclic, and if cyclic, is cyclized between a reactive chemical group of $Aaa^1$-$SUR^1$-$Aaa^2$ and a reactive chemical group of $Aaa^3$-$SUR^2$-$Aaa^4$. The cyclic bond may include an N-terminus group, a C-terminus group, an $R^1$ group of $SUR^1$ or $SUR^2$, if provided, or one or two amino acid side chain moieties. The cyclic bond may include a covalent bond such as an amide, disulfide, thioether, Schiff base, reduced Schiff base, imide, secondary amine, carbonyl, urea, hydrazone or oxime bond.

In yet another aspect of the invention, the peptidomimetic comprises a sequence which binds to one or more melanocortin receptors, including MC1-R, MC3-R, MC4-R or MC5-R and subtypes thereof, wherein the peptidomimetic comprises at least one surrogate of formula I. This peptidomimetic may be of the formula

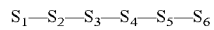

where $S_1$ is $Aaa^1$-$SUR^1$-$Aaa^2$ and $S_6$ is $Aaa^3$-$SUR^2$-$Aaa^4$ as defined above, on the proviso that $SUR^1$ and $SUR^2$ may optionally both be absent if at least one of $S_2$, $S_3$, $S_4$ or $S_5$ is a surrogate of formula I; and $S_2$ is an amino acid residue with an amino acid side chain moiety comprising an alkyl group, aryl group or a heteroaryl group, optionally fused to an aryl group, heteroaryl group, cycloalkyl group or heterocycloalkyl group, and optionally with one or two ring substituents, and when one or both ring substitutents are present, the substituents are the same or different and independently hydroxyl, halogen, halo-alkyl, halo-aryl, alkyl, or aryl groups attached directly or through an ether linkage, or is an amino acid residue of the formulas

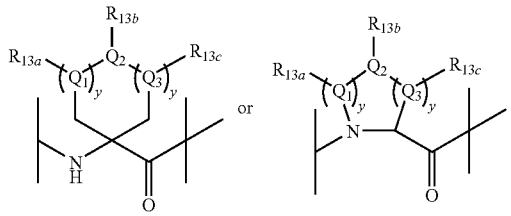

wherein:

$Q_1$, $Q_2$ and $Q_3$ are each independently $CH_2$, CH, C=O, NH, N, S or O;

$R_{13a}$ is not present if the y of $(Q_1)_y$ is 0 or if $Q_1$ is $CH_2$, C=O, NH, N with a double bond, S, or O, and otherwise $R_{13a}$ is a hydroxyl group, halogen group, or linear or branched $C_1$ to $C_7$ alkyl, aryl, heteroaryl, alkene, alkenyl, or aralkyl chain, in each instance attached directly or through an ether linkage to $Q_1$, on the proviso that $R_{13a}$ may form an aryl or heteroaryl with $R_{13b}$;

$R_{13b}$ is not present if $Q_2$ is $CH_2$, C=O, NH, N with a double bond, S, or O, and otherwise $R_{13b}$ is a hydroxyl group, halogen group, or linear or branched $C_1$ to $C_7$ alkyl, aryl, heteroaryl, alkene, alkenyl, or aralkyl chain, in each instance attached directly or through an ether linkage to $Q_2$, on the proviso that $R_{13b}$ may form an aryl or heteroaryl with either $R_{13a}$ or $R_{13c}$;

$R_{13c}$ is not present if the y of $(Q_3)_y$ is 0 or if $Q_3$ is $CH_2$, C=O, NH, N with a double bond, S, or O, and otherwise $R_{13c}$ is a hydroxyl group, halogen group, or linear or branched $C_1$ to $C_7$ alkyl, aryl, heteroaryl, alkene, alkenyl, or aralkyl chain, in each instance attached directly or through an ether linkage to $Q_3$, on the proviso that $R_{13c}$ may form an aryl or heteroaryl with $R_{13b}$; and y is in each instance independently 0 or 1;

or $S_2$ is a surrogate of formula I wherein $R^1$ is H or comprises alkyl, an aryl group or a heteroaryl group, optionally fused to an aryl group, heteroaryl group, cycloalkyl group or heterocycloalkyl group, and optionally with one or two ring substituents, and when one or both ring substituents are present, the substituents are the same or different and independently hydroxyl, halogen, halo-alkyl, halo-aryl, alkyl, or aryl groups attached directly or through an ether linkage;

$S_3$ is an amino acid residue with an amino acid side chain moiety comprising phenyl, 1-naphthyl, or 2-naphthyl, optionally with one or two ring substituents, and when one or both ring substituents are present, the substituents are the same or different and independently hydroxyl, halogen, halo-alkyl, halo-aryl, alkyl, or aryl groups attached directly or through an ether linkage, or is a surrogate of formula I wherein $R^1$ comprises phenyl, 1-naphthyl, or 2-naphthyl, optionally with one or two ring substituents, and when one or both ring substitutents are present, the substituents are the same or different and independently hydroxyl, halogen, halo-alkyl, halo-aryl, alkyl, or aryl groups attached directly or through an ether linkage;

$S_4$ is an amino acid residue with an amino acid side chain moiety comprising a heteroatom unit with at least one cationic center, hydrogen bond donor or hydrogen bond acceptor wherein at least one heteroatom is nitrogen or oxygen, or is a surrogate of formula I wherein $R^1$ comprises a heteroatom unit with at least one cationic center, hydrogen bond donor or hydrogen bond acceptor wherein at least one heteroatom is nitrogen or oxygen, or $S_4$ is an amino acid residue with an amino acid side chain moiety comprising an alkyl group or is a surrogate of formula I wherein $R^1$ comprises an alkyl group; and $S_5$ is an amino acid residue with an amino acid side chain moiety comprising an aryl group, a cycloalkyl group, two fused aryl groups, two aryl groups joined by a bond or —O—, or a heteroaryl group fused with a heteroaryl, aryl, cycloalkyl or heterocycloalkyl group, optionally with one or two ring substituents, and when one or both ring substituents are present, the substituents are the same or different and independently hydroxyl, halogen, halo-alkyl, halo-aryl, alkyl, or aryl groups attached directly or through an ether linkage, or is a surrogate of formula I wherein $R^1$ an aryl group, a cycloalkyl group, two fused aryl groups, two aryl groups joined by a bond or —O—, or a heteroaryl group fused with a heteroaryl, aryl, cycloalkyl or heterocycloalkyl group, optionally with one or two ring substituents, and when one or both ring substituents are present, the substituents are the same or different and independently hydroxyl, halogen, halo-alkyl, halo-aryl, alkyl, or aryl groups attached directly or through an ether linkage;

on the proviso that if at least one of $SUR^1$ or $SUR^2$ is not present, then at least one of $S_2$, $S_3$, $S_4$, or $S_5$ is a surrogate of formula I.

The peptidomimetic of the formula $S_1$—$S_2$—$S_3$—$S_4$—$S_5$—$S_6$ may be linear or cyclic, and if cyclic, is cyclized between a reactive chemical group of $Aaa^1$-$SUR^1$-Aaa and a reactive chemical group of $Aaa^3$-$SUR^2$-$Aaa^4$. The cyclic bond may include an N-terminus group, a C-terminus group, an $R^1$ group of $SUR^1$ or $SUR^2$, if provided, or one or two amino acid side chain moieties. The cyclic bond may include a covalent bond such as an amide, disulfide, thioether, Schiff base, reduced Schiff base, imide, secondary amine, carbonyl, urea, hydrazone or oxime bond.

5. Formulation and Use of Peptidomimetics of the Invention

Peptidomimetics made using one or more surrogates of formula I can be used for both medical applications and animal husbandry or veterinary applications. Typically, the peptidomimetic, or a pharmaceutical composition including the peptidomimetic, is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

The peptidomimetics disclosed herein, or made by methods disclosed herein, may be used for the treatment of any condition, syndrome or disease, and in particular for any condition, syndrome or disease for which a melanocortin receptor-specific peptide has some efficacy. The peptidomimetics disclosed herein, or made by methods disclosed herein, can have one or more advantages relative to melanocortin receptor-specific peptides, including but not limited to advantages such as increased resistance to enzymatic degradation, increased circulation half life, increased bioavailability, increased efficacy, increased specificity, prolonged duration of effect and combinations of the foregoing. Such advantages are due, in whole or part, to use of the surrogates of formula I.

Salt Form of Peptidomimetics. The peptidomimetics of this invention may be in the form of any pharmaceutically acceptable salt. The term "pharmaceutically acceptable salts" refers to salts prepared from pharmaceutically acceptable non-toxic bases or acids including inorganic or organic bases and inorganic or organic acids. Salts derived from inorganic bases include salts of aluminum, ammonium, calcium, copper, ferric, ferrous, lithium, magnesium, manganic, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the peptidomimetic of the present invention is basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of the peptidomimetics of this invention are prepared in a suitable solvent from the peptidomimetic and an excess of an acid, such as hydrochloric, hydrobromic, sulfuric, phosphoric, acetic, trifluoroacetic, citric, tartaric, maleic, succinic or methanesulfonic acid. The acetate salt form is especially useful. Where the peptidomimetics of embodiments of this invention include an acidic moiety, suitable pharmaceutically acceptable salts may include alkali metal salts, such as sodium or potassium salts, or alkaline earth metal salts, such as calcium or magnesium salts.

Pharmaceutical Compositions. Another embodiment of the present invention provides a pharmaceutical composition that includes a peptidomimetic of this invention and a pharmaceutically acceptable carrier. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

The peptidomimetics of the several embodiments of the present invention may be formulated or compounded into pharmaceutical compositions that include at least one peptidomimetic of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, manniton, sodium chloride and sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, amino acids, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a peptidomimetic of this invention over a period of time.

In general, the actual quantity of peptidomimetics administered to a patient will vary between fairly wide ranges depending on the mode of administration, the formulation used, and the response desired.

In practical use, the peptidomimetics can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, dermal, transdermal, pulmonary, deep lung, inhalation, buccal, sublingual, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

Because of their ease of administration, tablets and capsules represent an advantageous oral dosage unit form. If desired, a composition including a peptidomimetic of this invention may be coated by standard aqueous or nonaqueous techniques. The amount of active peptidomimetic in such therapeutically useful compositions is such that an effective dosage will be obtained. In another advantageous dosage unit form, sublingual pharmaceutical compositions may be employed, such as sheets, wafers, tablets or the like. The active peptidomimetic can also be administered intranasally as, for example, by liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch or alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be utilized as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Peptidomimetics may also be administered parenterally. Solutions or suspensions of active peptidomimetics can be prepared in water suitably mixed with a surfactant such as hydroxy-propylcellulose. Dispersions can also be prepared in glycerol, liquid polyethylene glycols and mixtures thereof in oils. These preparations may optionally contain a preservative to prevent the growth of microorganisms. Lyophilized single unit formulations may also be employed, such as are reconstituted with saline prior to administration, and thus do not require a preservative.

The pharmaceutical forms suitable for injectable use include sterile aqueous solutions or dispersions and sterile powders, such as lyophilized formulations, for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

Peptidomimetics as disclosed herein may be therapeutically applied by means of nasal administration. By "nasal administration" is meant any form of intranasal administration of any of the peptidomimetics of this invention. The peptidomimetics may be in an aqueous solution, such as a solution including saline, citrate or other common excipients or preservatives. The peptidomimetics may also be in a dry or powder formulation.

In an alternative embodiment, peptidomimetics may be administered directly into the lung. Intrapulmonary administration may be performed by means of a metered dose inhaler, a device allowing self-administration of a metered bolus of a peptidomimetic of this invention when actuated by a patient during inspiration. Both dry powder inhalation and nebulized aerosols may be employed.

According to another embodiment of the present invention, peptidomimetics of this invention may be formulated with any of a variety of agents that increase effective nasal absorption of drugs, including peptide drugs. These agents should increase nasal absorption without unacceptable damage to the mucosal membrane. U.S. Pat. Nos. 5,693,608, 5,977,070 and 5,908,825, among others, teach a number of pharmaceutical compositions that may be employed, including absorption enhancers, and the teachings of each of the foregoing, and all references and patents cited therein, are incorporated by reference.

If in an aqueous solution, certain peptidomimetics of the present invention may be appropriately buffered by means of saline, acetate, phosphate, citrate, acetate or other buffering agents, which may be at any physiologically acceptable pH, generally from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, acetate and the like, a 50 mM solution may be employed. In addition to buffering agents, a suitable preservative may be employed, to prevent or limit bacteria and other microbial growth. One such preservative that may be employed is 0.05% benzalkonium chloride.

It is also possible and contemplated that the peptidomimetic may be in a dried and particulate form. In a preferred embodiment, the particles are between about 0.5 and 6.0 µm, such that the particles have sufficient mass to settle on the lung surface, and not be exhaled, but are small enough that they are not deposited on surfaces of the air passages prior to reaching the lung. Any of a variety of different techniques may be used to make dry powder microparticles, including but not limited to micro-milling, spray drying and a quick freeze aerosol followed by lyophilization. With micro-particles, the peptidomimetics may be deposited to the deep lung, thereby providing quick and efficient absorption into the bloodstream. Further, with such approach penetration enhancers are not required, as is sometimes the case in transdermal, nasal or oral mucosal delivery routes. Any of a variety of inhalers can be employed, including propellant-based aerosols, nebulizers, single dose dry powder inhalers and multidose dry powder inhalers. Common devices in current use include metered dose inhalers, which are used to deliver medications for the treatment of asthma, chronic obstructive pulmonary disease and the like. Preferred devices include dry powder inhalers, designed to form a cloud or aerosol of fine powder with a particle size that is always less than about 6.0 µm.

Microparticle size, including mean size distribution, may be controlled by means of the method of making. For micromilling, the size of the milling head, speed of the rotor, time of processing and the like control the microparticle size. For spray drying, the nozzle size, flow rate, dryer heat and the like control the microparticle size. For making by means of quick freeze aerosol followed by lyophilization, the nozzle size, flow rate, concentration of aerosoled solution and the like control the microparticle size. These parameters and others may be employed to control the microparticle size.

The peptidomimetics of this invention may be therapeutically administered by means of an injection, typically a deep intramuscular injection, such as in the gluteal or deltoid muscle, of a time release injectable formulation. In one embodiment, a peptidomimetic of this invention is formulated with a PEG, such as poly(ethylene glycol) 3350, and optionally one or more additional excipients and preservatives, including but not limited to excipients such as salts, polysorbate 80, sodium hydroxide or hydrochloric acid to adjust pH, and the like. In another embodiment a peptidomimetic of this invention is formulated with a poly(ortho ester), which may be an auto-catalyzed poly(ortho ester) with any of a variable percentage of lactic acid in the polymeric backbone, and optionally one or more additional excipients. In one embodiment poly (D,L-lactide-co-glycolide) polymer (PLGA polymer) is employed, preferably a PLGA polymer with a hydrophilic end group, such as PLGA RG502H from Boehringer Ingelheim, Inc. (Ingelheim, Germany). Such formulations may be made, for example, by combining a peptidomimetic of this invention in a suitable solvent, such as methanol, with a solution of PLGA in methylene chloride, and adding thereto a continuous phase solution of polyvinyl alcohol under suitable mixing conditions in a reactor. In general, any of a number of injectable and biodegradable polymers, which are preferably also adhesive polymers, may be employed in a time release injectable formulation. The teachings of U.S. Pat. Nos. 4,938,763, 6,432,438, and 6,673,767, and the biodegradable polymers and methods of formulation disclosed therein, are incorporated here by reference. The formulation may be such that an injection is required on a weekly, monthly or other periodic basis, depending on the concentration and amount of peptidomimetic, the biodegradation rate of the polymer, and other factors known to those of skill in the art.

Routes of Administration. If it is administered by injection, the injection may be intravenous, subcutaneous, intramuscular, intraperitoneal or other means known in the art. The peptidomimetics of this invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the peptidomimetics of this invention are introduced across an epidermal layer of cells may be employed. Administration means may thus include administration through mucous membranes, buccal administration, oral administration, dermal administration, inhalation administration, pulmonary administration, nasal administration, urethral administration, vaginal administration, and the like.

In one aspect, a peptidomimetic of this invention is administered by means of a time release injectable formulation, such as a peptidomimetic of this invention in a formulation with a PEG, poly(ortho ester) or PLGA polymer. In another aspect, a peptidomimetic of this invention is administered by means of an automated delivery device providing subcutaneous delivery, either continuous or intermittent. A peptidomimetic of this invention may also be administered by transdermal administration.

Therapeutically Effective Amount. In general, the actual quantity of peptidomimetic of this invention administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect. Thus a therapeutically effective amount includes an amount of a peptidomimetic or pharmaceutical composition of this invention that is sufficient to induce a desired effect.

In general, the compounds of this invention are highly active. For example, the compound can be administered at about 0.01, 0.05, 0.1, 0.5, 1, 5, 10, 50, or 100 µg/kg body weight, depending on the specific peptidomimetics selected, the desired therapeutic response, the route of administration, the formulation and other factors known to those of skill in the art.

Therapeutic Application. In one embodiment, peptidomimetics of this invention that are MC1-R specific can be used as chemoprevention agents against sun-induced, such as by UV radiation, neoplastic activity in human skin. MC1-R agonist peptidomimetics of this invention may be employed to stimulate epidermal melanocytes to produce melanin as well as to convert pheomelanin to eumelanin. Eumelanin, which is dark brown or black pigmentation, is considered more photoprotective than pheomelanin, which is yellow or red pigmentation. The process of melanogenesis is believed to involve stimulation of MC1-R in epidermal melanocytes, thereby mediating the stimulation of tyrosinase enzymes within these pigment cells, inducing the conversion of tyrosine to dopa and then through dopaquinone to eumelanin. Sun tanning due to direct sun exposure is proposed to result from the same pathway by local production of melanotropic peptide from a POMC gene in the epidermis. Thus, stimulation of eumelanin production and conversion of pheomelanin to eumelanin may be a desirable chemoprevention modality in blocking sun- or UV-induced neoplastic activity in skin. A potent, high-affinity and highly selective MC1-R agonist peptidomimetic of this invention can accordingly be used as a therapeutic chemoprevention agent for combating harmful sun or UV exposure that induces neoplastic activity in skin melanocytes.

In another embodiment, peptidomimetics of this invention, including but not limited to peptidomimetics that are MC4-R agonists, partial agonists or functionally inactive may be used as a therapeutic agent to modify energy metabolism and feeding behavior, including treatment of pathologic obesity and related conditions. In addition to use in treatment of patients clinically diagnosed as obese, peptidomimetics of this invention may be employed with persons who are above optimal body weight, as an aid in weight loss.

In another embodiment, peptidomimetics of this invention, including but not limited to MC4-R antagonists, may be used as a therapeutic agent in eating disorders, such as treatment of anorexia and cachexia, which is malnutrition and wasting due to illness. In addition to use in treatment of patients diagnosed with anorexia or cachexia, peptidomimetics of this invention may be employed with persons who have below optimal body weight, and in particular with patients desiring to gain additional muscle mass.

In yet another embodiment, peptidomimetics of this invention can be used as therapeutic agents for treatment of sexual dysfunction, including treatment of both male erectile dysfunction and female sexual dysfunction.

In yet another embodiment, peptidomimetics of this invention may be used as therapeutic agents for treatment of inflammation, including specifically MC1-R, MC3-R and MC5-R agonists.

In yet another embodiment of the invention, peptidomimetics of this invention that are MC5-R specific can be used as agents to decrease sebum production, and thus may be efficacious in the treatment of acne and related diseases. The peptidomimetics for this application may be conveniently formulated for local administration, as through a gel, lotion, cream or other topical formulation.

In yet another embodiment, peptidomimetics of this invention may be employed in the treatment of drug or alcohol dependence, depression, anxiety and related conditions and indications.

6. Synthetic Methods for Surrogates Incorporated into Peptidomimetics

The surrogates of formula I can be obtained via standard, synthetic methodology. Some convenient methods are illustrated in the Schemes below. Starting materials useful for preparing the compounds of the invention and intermediates therefor, are commercially available or can be prepared from commercially available materials using known synthetic methods and reagents.

Protecting groups utilized herein denote groups which generally are not found in the final peptidomimetic but which are intentionally introduced at some stage of the synthesis in order to protect groups which otherwise might be altered in the course of chemical manipulations. Such protecting groups are removed or converted to the desired group at a later stage of the synthesis and compounds bearing such protecting groups thus are of importance primarily as chemical intermediates (although some derivatives also exhibit biological activity). Accordingly, the precise structure of the protecting group is not critical.

Numerous reactions for the formation and removal of such protecting groups are described in a number of standard works including, for example, *Protective Groups in Organic Chemistry*, Plenum Press, London and New York, 1973; Greene, Th. W. *Protective Groups in Organic Synthesis*, Wiley, New York, 1981; *The Peptides*, Vol. I, Schroder and Lubke, Academic Press, London and New York, 1965; and *Methoden der organischen Chemie*, Houben-Weyl, 4th Edition, Vol. 15/1, Georg Thieme Verlag, Stuttgart 1974, the disclosures of which are incorporated herein by reference.

The following examples of methods of synthesis of amino acid surrogates of formula I are intended to be exemplary, and it is to be understood that variations thereon may be undertaken by one of skill in the art, and such variations are intended to be included herein.

Synthesis of Ketopiperazine Scaffolds Mimicking Amino Acids without Functionalized R Side Chain (Methods A and B)

The surrogates were prepared by a variety of methods as described in Methods A and B.

Method A: The dipeptides (3) were formed by the mixed anhydride method, using Boc-serine (OBn)-OH (1), and an α-amino ester (2). The dipeptides were obtained in high yields, and usually no purification was required. Reduction of both the methyl ester and the amide group was done using diborane-tetrahydrofuran, with the secondary amines protected to give the di-Boc protected amino alcohol intermediates (4). Oxidation of the alcohols with pyridinium dichromate (PDC) with concomitant cyclization gave the piperazine-2-ones (5) in one step. Benzyl ether removal by hydrogenation, followed by protecting group exchange gave the Fmoc protected piperazine-2-ones (6). Finally, the primary alcohol was oxidized to the acid by any of a number of different methods (PDC, Jones oxidation, ruthenium chloride-sodium periodate, 2,2,6,6-tetramethyl-1-piperidinyloxy, free radical (TEMPO) oxidation) to give the final products (7).

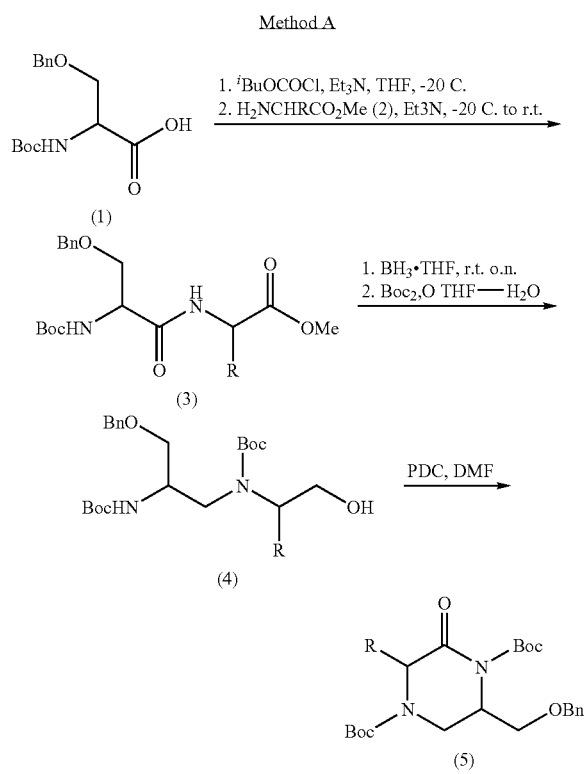

Synthesis of 2-(3-benzyloxy-2-tert-butoxycarbonylamino-propionylamino)-2-substituted acetic acid methyl ester (3): To a solution of 10 mmol of Boc serine benzyl ether (1) in 30 mL of dry tetrahydrofuran, kept at −20° C. under nitrogen, was added 22 mmol of triethylamine, followed by the slow addition of 11.4 mmol of isobutylchloroformate. A white solid precipitated out. The slurry was stirred for 15 minutes, and then 11.1 mmol of α-amino ester (2) was added in one portion. The slurry was stirred at −20° C. for 30 minutes, and then allowed to warm up to room temperature, stirred for 2 hours, and then concentrated to dryness. The mixture was then partitioned between 50 mL of ethyl acetate/30 mL of 1N hydrochloric acid solution. The layers were separated, and the organic layer washed with 1×20 mL of 1N hydrochloric acid, and 1×20 mL of saturated sodium bicarbonate solution, dried over magnesium sulfate and concentrated. Compounds (3) were usually obtained in yields above 90%, and no purification was required.

| R | Analytical Data for Compounds (3) |
|---|---|
| Ph | $^1$H NMR δ (CDCl$_3$): 1.43 (s, 9H, $^t$Bu), 3.0-3.18 (two sets of dd, 2H, CH$_2$-Ph), 3.50-3.57 (t, 1H, CH$_2$O), 3.68 (s, 3H, CH$_3$O), 3.87-3.96 (br. d, 1H, CH$_2$O), 4.23-4.33 (br. m, 1H, CHN), 4.45-4.57 (dd, 2H, CH$_2$O), 4.80-4.88 (m, 1H, CHN), 5.30-5.37 (m, 1H, NH), 7.0-7.38 (a series of m, 10H, Ph), yield =96%, $t_R$ = 6.88 min, (M$^+$ + 1) = 456.99 |
|   | $^1$H NMR δ (CDCl$_3$): 0.81-0.96 (a series of m, 6H, CH$_3$), 1.00-1.16 (m, 1H, CH$_2$), 1.30-1.45 (m, 1H, CH$_2$), 1.45 (s, 9H, $^t$Bu), 1.80-1.96 (m, 1H, CH), 3.54-3.64 (dd, 1H, CH$_2$O), 3.70 (s, 3H, CH$_3$O), 3.82-3.96 (dd, 1H, CH$_2$O), 4.28-4.40 (m, 1H, CHN), 4.51-4.61 (m, and s, 3H, CH$_2$O, and CHN), 5.51-5.61 (br. d, 1H, NH), 7.12-7.37 (br. m, 5H, Ph), yield = quant., $t_R$ = 6.93 min, (M$^+$ + 1) = 423.25 |
| H | $^1$H NMR δ (CDCl$_3$): 1.45 (s, 9H, $^t$Bu), 3.73 (s, 3H, CH$_3$O), 3.84-3.90 (m, 2H, CH$_2$N), 4.01-4.17 (m, 2H, CH$_2$O), 4.32-4.38 (br. m, 1H, CHN), 4.54-4.58 (d, 2H, CH$_2$O), 5.46-5.57 (d, 1H, NH), 7.05-7.12 (br. m, 1H, Ph), 7.24-7.40 (m, 4H, Ph), yield = quant., $t_R$ = 5.51 min, (M$^+$ + 1) = 367.07 |

Synthesis of Di-Boc-2-substituted-(2-amino-3-benzyloxy-propyl-amino)-ethanol (4): To a solution of 35 mmol of (3) in 50 mL of dry tetrahydrofuran, kept at room temperature under nitrogen, was added 200 mL of 1N diborane solution in tetrahydrofuran. The solution was stirred at room temperature overnight, and then slowly poured over an ice-cold solution of 200 mL of 1N hydrochloric acid solution. The biphasic solution was then neutralized with solid sodium hydroxide. 140 mL of a saturated solution of sodium bicarbonate was added, followed by 70 mmol of di-tert-butyl-dicarbonate, and the mixture stirred for 2 days at room temperature, diluted with 200 mL of ethyl acetate and the layers separated. The organic layer was dried over magnesium sulfate, and concentrated. The products (4) were purified by silica gel column chromatography.

| R | Analytical Data for Compounds (4) |
|---|---|
| Ph | $^1$NMR δ (CDCl$_3$): 1.42 (s, 9H, $^t$Bu), 1.48 (s, 9H, $^t$Bu), 2.48-3.02 (a series of m, 2H, CH$_2$-Ph), 3.1-3.48 (br. m, 1H, CH$_2$O), 3.25-3.48 (br. m, 2H, CH$_2$N),3.50-3.75 (m, 2H, CH$_2$O), 3.80-3.97 (m, 2H, CH$_2$O, and CHN), 4.25 (br. m, 1H, CHN), 4.45 (s 2H, CH$_2$O), 4.9 (br. s, 1H, OH), 5.3 (br. s, 1H, NH), 7.1-7.4 (m, 10H, Ph), yield = 76%, $t_R$ = 8.04 min, (M$^+$ + 1) = 515.25 |
|   | $^1$H NMR δ (CDCl$_3$): 0.84-0.96 (m, CH, CH$_2$, CH$_3$), 1.42 (s, 9H, $^t$Bu), 1.45 (s, 9H, $^t$Bu), 1.42-1.44 (m, 1H, CH), 2.88-3.11 (br. m, 2H, CH$_2$N), 3.42-3.57 (m, 2H, CH$_2$O), 3.62-4.10 (two m, 4H, CH$_2$O, and CHN), 4.51 (s, 2H, CH$_2$O), 7.27-7.38 (m, 5H, Ph), yield = 80%, $t_R$ = 8.19 min, (M$^+$ +1) = 481.26 |

| R | Analytical Data for Compounds (4) |
|---|---|
| H | $^1$H NMR δ (CDCl$_3$): 1.35-1.43 (m, 18H, $^t$Bu), 3.20-3.32 (m, 1H, CH$_2$N), 3.55-3.84 (a series of m, 8H, CH$_2$N, CH$_2$O), 3.90-4.05 (m, 1H, CHN), 4.45 (s, 2H, CH$_2$O), 4.9-5.02 (m, 1H, NH), 7.2-7.35 (m, 5H, Ph), yield = 56%, $t_R$ = 6.40 min, (M$^+$ +1) = 425.21 |

Synthesis of 1,4-di-Boc-6-benzyloxymethyl-3-substituted-piperazin-2-one (5): A solution of 70 mmol of (4), and 400 mmol of pyridinium dichromate in 300 mL of dry dimethylformamide was stirred at 48° C. under nitrogen for 6 hours, cooled to room temperature, poured into 1500 mL of water, and extracted with 4×500 mL of ethyl ether. The ethereal layers were combined, dried over magnesium sulfate, and concentrated. The products (5) were purified by silica gel column chromatography.

| R | Analytical Data for Compounds (5) |
|---|---|
| Ph | $^1$H NMR δ (CDCl$_3$): 1.4 (s, 9H, $^t$Bu), 1.5 (s, 9H, $^t$Bu), 3.05-3.58 (a series of m, CH$_2$-Ph, and CH$_2$N), 4.1-4.32 (a series of m, 2H, CH$_2$N), 4.47 (s, 2H, CH$_2$O), 4.78-4.86 (br. m, 1H, CHN), 7.12-7.42 (m, 10H, Ph), yield = 42%, $t_R$ = 8.65 min, (M$^+$ + 1) = 511.05. |
|  | $^1$H NMR δ (CDCl$_3$): 0.82-1.56 (four s, and four m, 27H, $^t$Bu, CH, CH$_2$, and CH$_3$), 3.20-3.52 (a series of m, 2H, CH$_2$N), 3.60-3.88 (a series of m, 2H, CH$_2$O), 4.20-4.60 (a series of m, one s, 4H, CH$_2$O, CHN), 7.21-7.37 (m, 5H, Ph), yield = 24%, $t_R$ = 9.23 min, (M$^+$ +1) = 477.32. |

Synthesis of 4-Fmoc-6-hydroxymethyl-3-substituted-piperazin-2-one (6): A suspension of 19 mmol of (5) and 2 g of 10% palladium on carbon in 200 mL of ethanol was hydrogenated at room temperature and atmospheric pressure overnight. The suspension was filtered through celite, and concentrated. The residue was redissolved in 40 mL of 50% trifluoroacetic acid in dichloromethane. The solution was stirred at room temperature for 2 hours, and then concentrated. The residue was redissolved in 60 mL of tetrahydrofuran/40 mL of water, and neutralized with solid sodium bicarbonate, followed by the addition of 40 mmol of solid sodium bicarbonate, and 20 mmol of Fmoc chloride. The mixture was then stirred at room temperature for 2 hours, diluted with 300 mL of ethyl acetate, and the layers separated. The organic layer was dried over magnesium sulfate, concentrated, and purified by silica gel column chromatography.

| R | Analytical Data for Compound (6) |
|---|---|
| Ph | $^1$H NMR δ (CDCl$_3$): 2.15-2.32 (br. m, 1H, CH$_2$-Ph), 2.70-2.81 (br. m, 1H, CH$_2$-Ph), 3.0-3.32 (br. m, 3H, CHN, and CH$_2$N), 3.47-3.65 (br. m, 3H, CH$_2$O, and CHN), 3.95-4.22 (two m, 2H, CH, and CHN), 4.32-4.48 (br. m, 2H, CH$_2$O), 4.84-4.92 (br. m, 1H, NH), 6.73-6.83 (br. m, 1H, Ph), 6.92-7.01 (br. m, 1H, Ph), 7.08-7.82 (a series of m, 11H, Ph, and fulvene), yield = 65%, $t_R$ = 5.78 min, (M$^+$ + 1) = 443.07. |

| R | Analytical Data for Compound (6) |
|---|---|
|  | $^1$H NMR δ (CDCl$_3$): 0.6-1.15 (br. peaks, 7H, CH$_2$, and CH$_3$), 1.20-1.42 (br. m, 1H, CH$_2$), 1.72-2.02 (two br. peaks, 1H, CH), 2.74-2.86 (t, 1/2H, CHN), 2.74-3.74 (a series of br. peaks, 5H, CH$_2$O, CH$_2$N, and CHN), 4.16-4.22 (br. m, 1H, CH), 4.52-4.74 (br. m, 2H, CH$_2$O), 7.24-7.82 (a series of m, 8H, fulvene), yield = 34%, $t_R$ = 5.72 min, (M$^+$ + 1) = 408.95 |
|  | $^1$H NMR δ (CDCl$_3$): 0.73-1.00 (m, 7H, CH$_3$), 2.2-2.3 (br. m, 0.5H, CH), 2.74-4.62 (a series of br. peaks, 12H, CH$_2$N, CH$_2$O and CHN), 3.68 (s, 3H, CH$_3$O), 7.26-7.77 (m, 9H, fulvene), yield = 45% (3 steps), $t_R$ = 5.34 min, (M$^+$ + 1) = 394.93 |

Synthesis of 4-Fmoc-5-substituted-6-oxo-piperazine-2-carboxylic acid (7): Compounds (7) were prepared by several methods.

(a) To a biphasic solution of 10 mmol of (6) in 180 mL of acetonitrile, 180 mL of carbon tetrachloride, and 240 mL of water, cooled to 0° C., was added 112 mmol of solid sodium periodate, followed by 340 mg of ruthenium chloride. The reaction was allowed to warm up to room temperature, stirred for 2 hours, and then filtered through celite. The layers were separated, and the aqueous layer re-extracted with 2×75 mL of ethyl acetate. The organic layers were combined, dried over magnesium sulfate, and concentrated.

(b) A solution of 12 mmol of (6), and 59 mmol of PDC in 60 mL of dry dimethylformamide was stirred at 48° C. under nitrogen for ~5 hours, cooled to room temperature, and poured over 600 mL of water, and extracted with 3×200 mL of dichloromethane. The organic layers were combined, dried over magnesium sulfate, and concentrated.

(c) To a solution of 17 mmol of (6) in 350 mL of acetone kept at room temperature was added 25 mL of Jones reagent (prepared from 8.0 g of chromic acid, 17.4 mL of water, and 6.9 mL of concentrated sulfuric acid). The mixture was stirred for 1 hour, 150 mL of isopropanol was added, and the mixture filtered through celite. The celite was washed with ethyl acetate. The organic layers were combined and concentrated. The residue was dissolved in 250 mL of ethyl acetate and washed with 2×50 mL of water, dried over magnesium sulfate, and concentrated.

(d) To a solution of 81 mmol alcohol (6) in 810 mL of acetonitrile kept at room temperature, was added phosphate buffer solution (prepared with 7.2 g of sodium phosphate monobasic, and 14.3 g of sodium phosphate dibasic in 295 mL of water), followed by the addition of 3.3 g (20.7 mmol) of TEMPO, and 18.6 g (164.4 mmol) of sodium chlorite, and the biphasic solution placed in an oil bath kept at 43° C., and then a solution of 43.3 mL (25.9 mmol) of sodium hypochlorite solution (prepared by mixing 19.3 mL of 10-13% sodium hypochlorite solution, and 24 mL of water) was added slowly. The reaction was stirred at 43° C. for 4 hours. The solution was cooled to room temperature, and a solution of 200 mL of 10% sodium hydrogen sulfite solution was added, stirred for 10 minutes, diluted with 500 mL of ethyl acetate, and the layers separated. The organic layer was washed with 1×100 mL of brine, 1×160 mL of 1N hydrochloric acid solution, dried over sodium sulfate, and concentrated.

The products (7) were purified by silica gel column chromatography.

| R | Analytical Data for Compounds (7) |
|---|---|
| ~~~~Ph (benzyl) | $^1$H NMR δ (CDCl$_3$): 2.36-2.45 (dd, 1H, CH$_2$-Ph), 2.62-2.76 (m, ½H, CH$_2$-Ph), 2.82-2.98 (m, ½H, CH$_2$-Ph), 3.13-3.25 (m, 1H, CH$_2$N), 3.98-4.64 (a series of m, 6H, CHN, CH$_2$O, CH$_2$, and CH), 4.87 (br. m, ½H, NH), 6.85 (br. s, 1H, Ph), 7.0-7.40 (a series of m, 12H, Ph and fulvene), 9.18-9.40 (br. d, 1H, CO$_2$H), $t_R$ = 5.91 min, (M$^+$ + 1) = 457.37. |
| ~~~~(sec-butyl) | $^1$H NMR δ (CDCl$_3$): 0.64-1.02 (overlapping t, 6H, CH$_3$), 1.02-1.68 (three br. m, 2H, CH$_2$), 1.96-2.16 (br. m, 1H, CH), 2.88-3.18 (m, 1H, CH$_2$N), 3.85-4.12 (three m, 2H, CH$_2$N, and CHN), 4.18-4.35 (m, 1H, CH), 4.55-4.72 (m, 2H, CH$_2$), 4.75-4.86 (br. m, 1H, NH), 7.28-7.82 (a series of m, 8H, fulvene), 9.1-9.26 (two br. s, 1H, CO$_2$H), $t_R$ = 5.86 min, (M$^+$ + 1) = 423.20. |
| ~~~~(isobutyl) | $^1$H NMR δ (CDCl$_3$): 0.62-1.03 (m, 7H, CH$_3$), 1.90-2.05 (br. m, 1H, CH), 2.87-4.60 (a series of br. peaks, 8H, CH$_2$N, CH$_2$O and CHN and CH), 7.29-7.80 (m, 9H, fulvene), yield = 61%, $t_R$ = 5.52 min, (M$^+$ + 1) = 409.11 |

Method B: Intermediates Di-Boc-2-substituted-(2-amino-3-benzyloxy-propyl-amino)-ethanols (4), prepared as described in method A, were oxidized to the acid using TEMPO/isocyanuric acid reagent, and then esterified with iodomethane to give fully protected reduced dipeptide analogs (8). Deprotection of the Boc groups, and the benzyl ether, gave 3-substituted 5-hydroxymethyl-piperazin-2-ones, which were protected as the Fmoc derivatives to give (6), which were oxidized to the final product as described in method A.

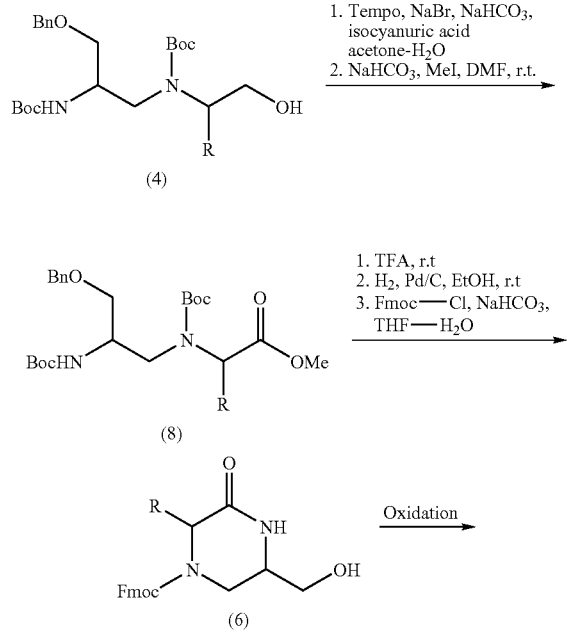

Method B

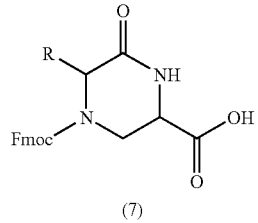

Synthesis of Di-Boc-(2-amino-3-benzyloxy-propylamino)-2-substituted acetic acid methyl ester (8): To a suspension of 76 mmol of (4) in 680 mL of acetone, and 210 mL of a saturated sodium bicarbonate solution, kept at 0° C., was added 21 mmol of solid sodium bromide, and 2.9 mmol of TEMPO, followed by the slow addition of 156 mmol of trichloroisocyanuric acid. The reaction was stirred for 30 minutes at 0° C., and then at room temperature overnight, acidified with a solution of 1N hydrochloric acid, and extracted with 2×300 mL of ethyl acetate. The organic layer was washed with 3×50 mL of 1N hydrochloric acid, dried over magnesium sulfate, and concentrated. The residue was redissolved in 40 mL of dry dimethylformamide and 95 mmol of solid sodium bicarbonate, and 112 mmol of iodomethane was added, and the mixture stirred at room temperature under nitrogen until HPLC showed the reaction was complete; the solution was then diluted with 200 mL of ethyl ether, and washed with 2×100 mL of water, dried over magnesium sulfate, and concentrated. The products (8) were purified by silica gel column chromatography.

| R | Analytical Data for Compounds (8) |
|---|---|
| ~~~~Ph | $^1$H NMR δ (CDCl$_3$): 1.41 (s, 9H, $^t$Bu), 1.46 (s, 9H, $^t$Bu), 2.44-2.58 (d, ½H, CH$_2$-Ph), 2.66-2.88 (d, ½H, CH$_2$-Ph), 3.16-3.46 (three sets of m, 5H, CH$_2$-Ph, CH$_2$N, and CH$_2$O), 3.72 (s, 3H, CH$_3$O), 3.75-4.05 (two m, 1H, CHN), 4.42 (s, 2H, CH$_2$O), 4.95-5.10 (d, ½H, NH), 5.30-5.38 (d, ½H, NH), 7.10-7.38 (m, 10H, Ph), yield = 62%, $t_R$ = 7.75 min, (M$^+$ + 1) = 529.03. |
| ~~~~H | $^1$H NMR δ (CDCl$_3$): 1.41 (s, 9H, $^t$Bu), 1.42 (s, 9H, $^t$Bu), 3.30-3.60 (br. m, 4H, CH$_2$N, CH$_2$O), 3.70 (s, 3H, CH$_3$O), 3.75-3.95 (m, 2H, CH$_2$N), 4.51 (s, 2H, CH$_2$O), 5.0-5.08 (br. s, 1H, NH), 7.25-7.37 (m, 5H, Ph), yield = 47% $t_R$ = 7.28 min, (M$^+$ + 1) = 453.17. |

Synthesis of 4-Fmoc-6-hydroxymethyl-3-substituted-piperazin-2-one (6): A solution of 36 mmol of (8) in 40 mL of 50% trifluoroacetic acid in dichloromethane was stirred at room temperature for 2 hours, and then poured in 200 mL of saturated sodium bicarbonate solution. The layers were separated, and the organic layer concentrated. The residue was redissolved in 100 mL of ethyl acetate, and washed with 2×50 mL of water, dried over magnesium sulfate, and concentrated. The residue was dissolved in 100 mL of ethanol, and 5 g of 10% palladium on carbon and 35 mL of a 1N hydrochloric acid solution was added, and the mixture hydrogenated at room temperature and atmospheric pressure until HPLC showed the reaction was complete; the solution was then filtered through celite and concentrated. The residue was redissolved in 80 mL of ethyl acetate, 70 mmol of sodium bicarbonate in 30 mL of water was added, and the mixture stirred at room temperature overnight. The ethyl acetate was removed and 100 mL of tetrahydrofuran was added, followed by 178 mmol of solid sodium bicarbonate and 43 mmol of Fmoc chloride, and the mixture was stirred until HPLC showed it was complete, diluted with 300 mL of ethyl acetate, and the layers separated. The organic layer was washed with 2×50 mL of water, dried over magnesium sulfate, and concentrated. The products (6) were purified by silica gel column chromatography.

Synthesis of 4-Fmoc-5-substituted-6-oxo-piperazine-2-carboxylic acid (7): Compounds (7) were prepared as described in method A.

General Common Synthetic Scheme for the Preparation of Ketopiperazine Scaffolds Applicable to Compounds with or without Functionalized R sidechains (Methods C, E, F)

Method C: (2-Fmoc-amino-3-R'—O-propylamino)-2-substituted acetic acid methyl esters (10) were prepared by reductive amination of Fmoc O-protected serinal (9) with α-amino esters (2), using either sodium cyanoborohydride or sodium triacetoxyborohydride as the reducing agent. The Fmoc O-protected serinal (9) required for the reductive amination was prepared according to method D, either by reduction of the ester (12) by di-isobutylaluminum hydride, by oxidation of Fmoc O-protected serinol (13) with Dess-Martin periodinane, or by reduction of the Fmoc O-protected serine Weinreb amide (14) with lithium aluminum hydride. The preferred method for the preparation of Fmoc O-protected serinals (9) was the reduction of the Weinreb amide analog. (2-Fmoc-amino-3-R'—O-propylamino)-2-substituted acetic acid methyl esters (10) were then N and O deprotected, cyclized, and Fmoc protected to give 3-substituted 6-hydroxymethyl-piperazin-2-ones (6), which were then oxidized to the final product (7) as described in method A.

The protecting group (R') on the hydroxyl group of Fmoc-O-protected serinal (9) used in the synthesis depends on the nature of the side chain R of the amino ester. When R contained no functional groups, the side chain of Fmoc serine was protected as the ′Bu ether. When R contained functional groups, the side chain of Fmoc serine was protected as the trityl ether.

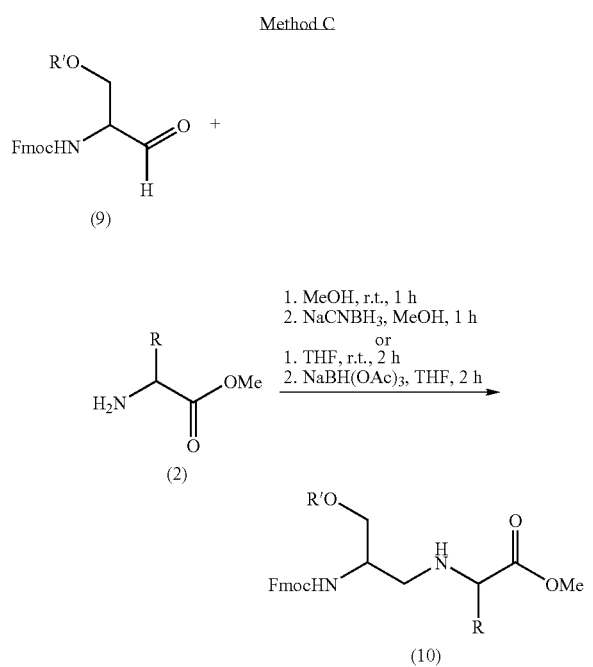

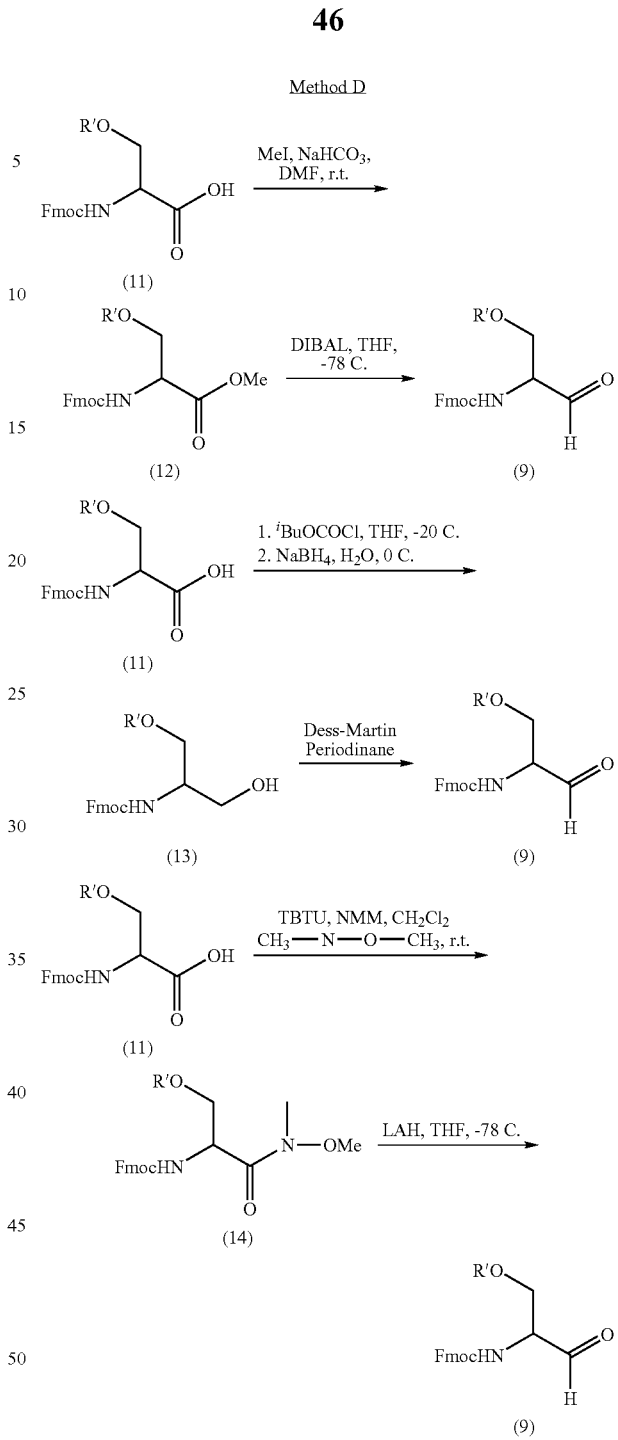

Method D: Synthesis of various Fmoc-O-protected serinals (9). Synthesis of Fmoc-O—R' serine methyl ester (12): A slight suspension of 80 mmol of Fmoc O—R' serine (11), 10.0 g (120 mmol) of solid sodium bicarbonate, and 10.0 mL (160 mmol) of iodomethane in 80 mL of dry dimethylformamide, kept under nitrogen, was stirred at room temperature overnight. The reaction mixture was then poured over 500 mL of water, and the solid filtered. The solid was redissolved in 800 mL of ethyl acetate, and washed with 1×200 mL of water, dried over magnesium sulfate, and concentrated. No purification was required.

| R' | Analytical Data for Compounds (12) |
|---|---|
| ᵗBu | ¹H NMR δ (CDCl₃): 1.14 (s, 9H, ᵗBu), 3.57-3.70 (m, 1H, CH₂—O), 3.75 (s, 3H, O—CH₃), 3.79-3.83 (m, 1H, CH₂—O), 4.01-4.50 (a series of multiples, 4H), 5.64-5.68 (d, 1H, NH), 7.28-7.78 (8H, fulvene), yield = 93% $t_R$ = 7.8 min. |
| Trt | ¹H NMR δ (CDCl₃): 3.42-3.48 (m, 1H, CH₂—O), 3.59-3.66 (m, 1H, CH₂—O), 3.81 (s, 3H, CH₃—O), 4.10-4.18 (m, 1H, CH), 4.36-4.42 (m, 2H, CH₂—O), 4.50-4.57 (m, 1H, CH—N), 5.73-5.78 (d, 1H, NH), 7.22-7.82 (8H, fulvene), yield = quant., $t_R$ = 9.04 min. |

Synthesis of Fmoc-O—R' serinol (13): To a solution of 10.0 mmol of Fmoc O—R' serine (11) in 50 mL of dry tetrahydrofuran, kept at −20° C. under nitrogen, was added 1.77 mL (12.7 mmol) of triethyl amine, followed by the slow addition of 1.57 mL (12.0 mmol) of isobutylchloroformate. The mixture was stirred for 30 minutes, and then poured slowly over an ice-cold solution of 3.77 g (99.6 mmol) of sodium borohydride in 10 mL of water, keeping the temperature below 5° C. The reaction was stirred at 0° C. for 15 minutes, and then quenched with 1N hydrochloric acid solution. The reaction mixture was diluted with 100 mL of ethyl acetate, and the layers separated. The organic layer was washed with 2×25 mL of 1N hydrochloric acid solution, 2×25 mL of water, dried over magnesium sulfate and concentrated. The compounds were purified by silica gel column chromatography.

| R' | Analytical Data for Compounds (13) |
|---|---|
| ᵗBu | ¹H NMR δ (CDCl₃): 1.14 (s, 9H, ᵗBu), 2.90-2.95 (d, 1/2H, CH₂—O), 3.63 (d, 2H, CH₂—O), 3.65-3.93 (m, 3H, CH₂—O), 4.20-4.35 (t, 1H, CH), 4.35-4.45 (d, 2H, CH₂), 5.50-5.57 (d, 1H, NH), 7.26-7.8 (8H, fulvene), yield = 85%, $t_R$ = 6.42 min. |
| Trt | ¹H NMR δ (CDCl₃): 3.24-3.32 (br. d, 1H, CH₂—O), 3.30-3.45 (br. m, 1H, CH₂—O), 3.60-3.987 (br. m, 3H, CH₂—O, and CH—N), 4.13-4.22 (br. m, 1H, CH), 4.32-4.40 (br. d, 2H, CH₂), 5.24-5.32 (br. d, 1H, NH), 7.16-7.76 (23H, fulvene, and Trt), yield = 92%, $t_R$ = 8.39 min. |

Synthesis of Fmoc-O—R' serine Weinreb amide (14): A suspension of 20.2 mmol of Fmoc O—R' serine (11), 6.98 g (21.6 mmol) of 2-(1H-benzotriazol-1-yl)-1,1,3,3-tetramethyluronium tetrafluoroborate (TBTU), and 2.5 mL (22.7 mmol) of N-methyl-morpholine in 80 mL of dry dichloromethane was stirred at room temperature under nitrogen for 20 minutes, and then 3.02 g (31 mmol) of N,O-di-methyl-hydroxylamine hydrochloride and 3.3 mL (30 mmol) of N-methylmorpholine were added, and the suspension stirred at room temperature overnight. The solution formed was then concentrated to dryness, repartitioned between 200 mL of ethyl acetate and 100 mL of water, washed with 2×40 mL of 1N hydrochloric acid solution and then 2×40 mL of saturated sodium bicarbonate solution, dried over magnesium sulfate, and concentrated. No purification was required.

| R' | Analytical Data for Compounds (14) |
|---|---|
| ᵗBu | ¹H NMR δ (CDCl₃): 1.45 (s, 9H, ᵗBu), 3.30 (s, 3H, CH₃—N), 3.55-3.7 (m, 2H, CH₂—O), 3.76 (s, 3H, CH₃—O), 4.19-4.26 (m, 1H, CH), 4.30-4.38 (m, 2H, CH₂—O), 4.82-4.91 (broad m, 1H, CHN), 5.68-5.75 (d, 1H, NH), 7.2-7.8 (8H, fulvene), yield = quant., $t_R$ = 6.59 min. |
| Trt | ¹H NMR δ (CDCl₃): 3.24 (s, 3H, CH₃N), 3.34-3.46 (m 2H, CH₂O), 3.62 (s, 3H, CH₃O), 4.15-4.37 (two m, CH₂, CH), 4.86-4.98 (m 1H, CHN), 5.80-5.86 (d, 1H, NH), 7.18-7.8 (a series of m, 23H, Trt and fulvene), yield = quant., $t_R$ = 8.0 min. |

Synthesis of Fmoc-O—R' serinal (9) from ester (12): To a solution of 3.5 mmol of (12) in 5 mL of tetrahydrofuran, kept at −78° C. under nitrogen, was added slowly 10 mL of N diisobutyl aluminum hydride (DIBAL) solution, stirred for 15 minutes, and quenched by the slow addition of a saturated solution of sodium and potassium tartrate. The reaction was allowed to warm up to room temperature, diluted with 50 mL of ethyl acetate, and 50 mL of a saturated solution of sodium and potassium tartrate was added. The layers were separated, and the aqueous layer re-extracted with 1×50 mL of ethyl acetate. The organic layers were combined, dried over magnesium sulfate, and concentrated. Compounds (9) were used without further purification in the next step.

| R' | Analytical Data for Compounds (9) |
|---|---|
| ᵗBu | ¹H NMR δ (CDCl₃): 1.16 (s, 9H, ᵗBu), 3.59-3.66 (dd, 1H, CH₂O), 3.90-3.98 (dd, 1H, CH₂O), 4.20-4.27 (t, 1H, CH), 4.32-4.45 (two m, 3H, CHN, and CH₂O), 5.64-5.74 (br. d, 1H, NH), 7.28-7.35 (m, 2H, fulvene), 7.36-7.44 (m, 2H, fulvene), 7.58-7.65 (d, 2H, fulvene), 7.73-7.78 (d, 2H, fulvene), 9.62 (s, 1H, CHO). |
| Trt | ¹H NMR δ (CDCl₃): 3.53-3.61 (dd, 1H, CH₂O), 3.66-3.75 (dd, 1H, CH₂O), 4.33-4.47 (two m, 4H, CHN, CH, and CH₂), 5.66-5.75 (d, 1H, NH), 7.20-7.81 (a series of m, 23H, Trt, and fulvene), 9.6 (s, 1H, CHO). |

Synthesis of Fmoc-O—R' serinal (9) from alcohol (13): To a solution of 80 mmol of Fmoc-O—R' serinol (13) in 200 mL of dry dichloromethane, kept at room temperature under nitrogen, was added 88 mmol of Dess-Martin periodinane, and the reaction was stirred for 2.5 hours and quenched by addition of 400 mL of 10% aqueous sodium thiosulfate solution. The layers were separated, and the organic layer concentrated, diluted with 300 mL of ethyl ether, and washed three times with a saturated aqueous bicarbonate solution containing 10% sodium thiosulfate, dried over magnesium sulfate, and concentrated.

Synthesis of Fmoc-O—R' serinal (9) from Weinreb amide (14): To a solution of 8.8 g (20.2 mmol) of crude Fmoc-O—R' serine Weinreb amide intermediate (14) in 60 mL of dry tetrahydrofuran, cooled to −78° C. under nitrogen, was added 30 mL of 1N lithium aluminum hydride solution in tetrahydrofuran. The solution was stirred for 15 minutes and then quenched by the slow addition of 30 mL of a 1.4N solution of potassium hydrogen sulfate. After warming up to room temperature, the solid was filtered and the filtrate concentrated to dryness. The residue was repartitioned between 50 mL of ethyl acetate and 25 mL of 1N hydrochloric acid solution. The layers separated, and the organic layer was dried over magnesium sulfate, filtered, and concentrated.

Synthesis of (2-Fmoc-amino-3-R'—O-propylamino)-2-substituted acetic acid methyl ester (10): compounds (10) were prepared by reductive amination using sodium cyanoborohydride or sodium triacetoxyborohydride as the reducing agent.

Sodium cyanoborohydride method: To a solution of 8.5 mmol of (2) hydrochloride salt in 20 mL of methanol, kept at room temperature under nitrogen, was added 2.3 mmol of solid potassium hydroxide, and the mixture stirred for 25 minutes. A solution of Fmoc-O—R' serinal (9) in 10 mL of methanol was added to the above suspension, and the reaction mixture was stirred for 1 hour. A solution of 8.5 mL of 1N sodium cyanoborohydride in tetrahydrofuran was added slowly, and the reaction stirred for another 1 hour, filtered, and concentrated. The residue was partitioned between ethyl acetate and water, and the organic layer washed with 1×20 mL of saturated sodium bicarbonate, dried over sodium sulfate, and concentrated.

Sodium triacetoxyborohydride method: A suspension of 21 mmol of (2) hydrochloride salt, and 2.9 mL (21 mmol) of triethyl amine in 50 mL of dry tetrahydrofuran, was stirred at room temperature for 45 min, and then a solution of ~20 mmol crude Fmoc-(O—R')-serinal (9) in 30 mL of tetrahydrofuran was added, followed by 1.7 g of 4A powdered molecular sieves, and the suspension was stirred for an additional 2 h. 6.4 g (30 mmol) of solid sodium triacetoxyborohydride was added, and the suspension stirred at room temperature overnight. The suspension was diluted with methanol, the molecular sieves filtered, and the filtrate concentrated. The residue was partitioned between 100 mL of ethyl acetate and 50 mL of water. The organic layer was dried over sodium sulfate, filtered, and concentrated.

Compounds (10) were purified by silica gel column chromatography.

| R' | R | Analytical Data for Compounds (10) |
|---|---|---|
| $^t$Bu | 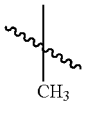 | $^1$H NMR δ (CDCl$_3$): 1.17 (s, 9H, $^t$Bu), 1.26-1.32 (d, 3H, CH$_3$), 2.68-2.80 (br. m, 2H, CH$_2$N), 3.32-3.56 (two br. m, 2H, CH$_2$O), 3.72 (s, 3H, CH$_3$O), 3.66-3.82 (m, 1H, CHN), 4.18-4.28 (t, 1H, CH), 4.30-4.46 (d, 2H, CH$_2$), 5.34-5.44 (br. d, 1H, NH), 7.25-7.44 (two m, 4H, fulvene), 7.59-7.64 (d, 2H, fulvene), 7.74-7.79 (d, 2H, fulvene), yield = 57%, $t_R$ = 4.93 min, (M$^+$ + 1) = 455.67. |
| $^t$Bu | 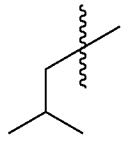 | $^1$H NMR δ (CDCl$_3$): 0.88-0.98 (br. t, 6H CH$_3$), 1.21 (s 9H, $^t$Bu), 1.26-1.34 (m, 2H, CH$_2$), 1.44-1.54 (m, 1H, CH), 2.58-2.86 (two m, 1H, CH$_2$N), 3.25-3.35 (m, 1H, CH$_2$N), 3.37-3.58 (two m, 2H, CH$_2$O), 3.72-3.80 (br. m, 1H, CHN), 4.14-4.31 (m, 1H, CH), 4.32-4.45 (br. d, 2H, CH$_2$), 5.34-5.44 (br. d, 1H, NH), 7.30-7.84 (a series of m, 8H, fulvene), yield = 50%, $t_R$ = 5.66 min, (M$^+$ + 1) = 511.67. |
| $^t$Bu | 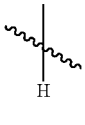 | $^1$H NMR δ (CDCl$_3$): 1.17 (s, 9H, $^t$Bu), 2.68-2.78 (m, 1H, CH$_2$N), 2.82-2.92 (m, 1H, CH$_2$N), 3.35-3.55 (m, 4H, CH$_2$N, and CH$_2$O), 3.73 (s, 3H, CH$_3$O), 3.75-3.85 (m, 1H, CHN), 4.20-4.28 (m, 1H, CH), 4.32-4.48 (m, 2H, CH$_2$), 5.40-5.50 (d, 1H, NH), 7.28-7.8 (a series of m, 8H, fulvene), yield = 44%, $t_R$ = 5.02 min, (M$^+$ + 1) = 441.50. |
| $^t$Bu |  | $^1$H NMR δ (CDCl$_3$): 0.84-0.92 (br. t, 3H, CH$_3$), 1.17 (s, 9H, $^t$Bu), 1.28-1.35 (m, 4H, CH$_2$), 1.48-1.84 (two m, 2H, CH$_2$), 2.62-2.82 (m, 2H, CH$_2$N), 3.20-3.33 (m, 1H, CH$_2$N), 3.35-3.54 (two m, 2H, CH$_2$O), 3.72 (s, 3H, CH$_3$O), 3.64-3.80 (m, 1H, CHN), 4.20-4.28 (t, 1H, CH), 4.32-4.42 (m, 2H, CH$_2$O), 5.34-5.44 (br. d, 1H, NH), 7.25-7.79 (a series of m, 8H, fulvene), yield = 65%, $t_R$ = 5.85 min, (M$^+$ + 1) = 441.27. |
| Trt | 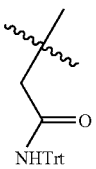 | $^1$H NMR δ (CDCl$_3$): 2.36-2.63 (br. m, 2H, CH$_2$CO), 2.65-2.90 (br. m, 2H, CH$_2$N), 3.05-3.20 (br. m, 2H, CH$_2$O), 3.50-3.64 (br. m, 1H, CHN), 3.68 & 3.69 (two s, 3H, CH$_3$O), 3.82-3.94 (br. m, 1H, CHN), 4.12-4.21 (br. m, 1H, CH), 4.24-4.43 (br. m, 2H, CH$_2$O), 4.90-4.98 (br. d, 1H, NH), 7.15-7.80 (a series of m, 23H, fulvene and Trt), yield = 39%, $t_R$ = 8.13 min, (M$^+$ + 1) = 926.99. |
| Trt | 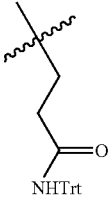 | $^1$H NMR δ (CDCl$_3$): 1.68-1.82 (m, 1H, CH$_2$), 1.85-1.99 (m, 1H, CH$_2$), 2.12-2.37 (m, 2H, CH$_2$CO), 2.58-2.96 (a series of four m, 2H, CH$_2$N), 3.08-3.28 (br. m, 2H, CH$_2$O), 3.66 & 3.67 (two s, 3H, CH$_3$O), 3.76-3.89 (br. m, 1H, CHN), 4.15-4.24 (br. m, 1H, CH), 4.28-4.41 (br. d, 2H, CH$_2$O), 5.10-5.22 (br. d, ½H, NH), 5.28-5.35 (br. d, ½H, NH), 7.15-7.80 (a series of m, 23H, fulvene, and Trt), yield = 43%, $t_R$ = 8.10 min, (M$^+$ + 1) = 940.97. |
| Trt | 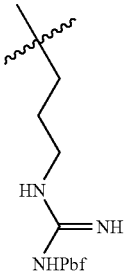 | $^1$H NMR δ (CDCl$_3$): 1.43 (s, 6H, CH$_3$), 1.46-1.56 (m, 4H, CH$_2$), 2.06 (s, 3H, CH$_3$), 2.50 (s, 3H, CH$_3$), 2.57 (s, 3H, CH$_3$), 2.75-2.80 (m, 1H, CH$_2$N), 2.91 (s, 2H, CH$_2$), 3.12-3.32 (three br. m, 4H, CH$_2$N), 3.68 (s, 3H, CH$_3$O), 4.13-4.21 (t, 1H, CH), 4.28-4.38 (d, 2H, CH$_2$), 5.12-5.23 (br. d, 1H, NH), 5.80-6.12 (two br. m, 2H, NH), 7.18-7.80 (a series of m, 23H, fulvene, and Trt), yield = 68%, $t_R$ = 7.52 min, (M$^+$ + 1) = 997.91 |
| Trt | 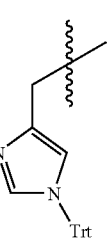 | $^1$H NMR δ (CDCl$_3$): 2.75-2.98 (two m, 2H, CH$_2$N), 3.06-3.18 (m, 1H, CH$_2$N), 3.22-3.33 (m, 1H, CH$_2$N), 3.57 & 3.60 (two s, 3H, CH$_3$O), 3.80-3.92 (m, 1H, CHN), 4.00-4.08 (m, 1H, CH), 4.18-4.30 (br. d, 2H, CH$_2$), 7.00-7.80 (a series of m, 25H, fulvene, Trt, and Imidazole), yield = 57%, $t_R$ = 7.59 min, (M$^+$ + 1) = 949.79. |
| Trt | 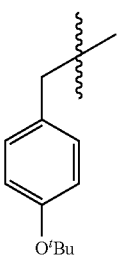 | $^1$H NMR δ (CDCl$_3$): 1.26 & 1.27 (two s, 9H, $^t$Bu), 2.50-2.61 (dd, 1H, CH$_2$—Ph), 2.76-2.86 (m, 2H, CH$_2$—Ph, and CH$_2$N), 2.92-3.20 (m, 1H, CH$_2$N), 2.92-3.20 (m, 2H, CH$_2$O), 3.32-3.46 (m, 1H, CH$_2$O), 3.59 (s, 3H, CH$_2$O), 3.79-3.88 (m, 1H, CHN), 4.18-4.28 (m, 1H, CH), 4.30-4.37 (br. d, 2H, CH$_2$O), 5.18-5.26 (br. d, 1H, NH), 6.80-6.88 (d, 2H, Ph), 6.96-7.02 (d, 2H, Ph), 7.18-7.80 (a series of m, 23H, fulvene, and Trt), yield = 23%. |
| Trt | 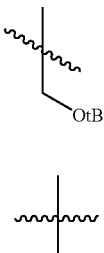 | $^1$H NMR δ (CDCl$_3$): 1.11 (s, 9H, $^t$Bu), 2.54-2.74 (two m, 2H, CH$_2$N), 3.02-3.58 (six m, 6H, CH$_2$O, CH$_2$N, and CHN), 3.70 (s, 3H, CH$_3$O), 3.83-3.93 (m, 1H, CHN), 4.15-4.29 (m 1H, CH), 4.34-4.37 (d, 2H, CH$_2$), 5.46-5.53 (br. d, 1H, NH), 7.18-7.79 (a series of m, 23H, fulvene, and Trt), yield = 45%, (M$^+$ + 1) = 713.42. |
| Trt | 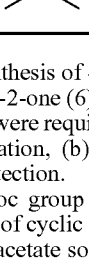 | $^1$H NMR δ (CDCl$_3$): 0.80-0.92 (m, 7H, CH$_3$), 1.75-1.90 (br. m, 1H, CH), 2.6-4.36 (a series of m, 9H, CH$_2$O, CH$_2$N, CHN), 3.68 (s, 3H, CH$_3$O), 5.5 (d, 0.5H, CH), 7.23-7.77 (m, 24H, fulvene and Trt), yield = 72% (3 steps), $t_R$ = 6.86 min, (M$^+$ + 1) = 669.10. |

Synthesis of 4-Fmoc-6-hydroxymethyl-3-substituted-piperazin-2-one (6): For the preparation of compounds (6) three steps were required: (a) Fmoc deprotection with concomitant cyclization, (b) Fmoc protection, and (c) hydroxyl group deprotection.

Fmoc group removal and cyclization: A solution of 10 mmol of cyclic compound in 30 mL of 30% diethyl amine in ethyl acetate solution was stirred at room temperature overnight, and then concentrated to dryness.

(a) Fmoc protection: To a biphasic solution of 10 mmol of compound in 20 mL of tetrahydrofuran and 10 mL of water, was added 2.52 g (30 mmol) of solid sodium bicarbonate, followed by 3.36 g (13 mmol) of Fmoc-Cl. The mixture was stirred for 3 hours, diluted with ethyl acetate, the layers separated, and the organic layer washed with water, dried over magnesium sulfate, and concentrated.

(b) Hydroxyl group deprotection: For compounds containing a $^t$Bu ether protecting group: The compounds were deprotected with a solution of 90% trifluoroacetic acid in dichloromethane for 1-2 hours, and then concentrated to dryness. The residue was dissolved in ethyl acetate and washed with a saturated solution of sodium bicarbonate, dried over magnesium sulfate, and then concentrated. For compounds containing a Trt ether protecting group: the compounds were deprotected by adding a solution of 1-10% trifluoroacetic acid in dichloromethane containing 2-10% tri-isopropyl silane. The reaction was instantaneous. The solution was then neutralized by pouring it into a saturated solution of sodium bicarbonate. The layers were separated, dried over sodium sulfate, and concentrated.

Compounds (6) were purified by silica gel column chromatography.

| R | Analytical Data for Compounds (6) |
|---|---|
| CH$_3$ | $^1$H NMR δ (CDCl$_3$): 1.17-1.35 (br. m, 3H, CH$_3$), 2.64-2.82 (t, 1H, CH$_2$N), 3.2-3.8 (two br. m, 3H, CH$_2$O, CH$_2$N), 4.18-4.44 (br. t, 1H, CH), 4.64-4.90 (br. d, 2H, CH$_2$O), 6.70-6.86 (br. s, 1H, NH), 7.22-7.82 (a series of m, 8H, fulvene), yield = 72%, $t_R$ = 4.64 min, (M$^+$ + 1) = 367.32. |
| (isobutyl) | $^1$H NMR δ (CDCl$_3$): 0.64-1.02 (m, 6H, CH$_3$), 1.45-1.63 (m, 3H, CH$_2$, and CH), 2.65-2.84 (m, 1H, CH$_2$N), 2.89-3.76 (a series of br. m, 5H, CH$_2$O, and CHN), 4.17-4.28 (br. m, 1H, CH), 4.48-4.82 (three br. m, CH$_2$O, NH, and OH), 6.95-7.82 (a series of br. m, 8H, fulvene), yield = 51%, $t_R$ = 5.43 min, (M$^+$ + 1) = 409.08. |
| H | $^1$H NMR δ (CDCl$_3$): 3.17-3.78 (a series of br. m, 5H, CH$_2$O, CH$_2$N, and CHN), 4.21-4.27 (t, 1H, CH), 4.42-4.68 (br. peak, 2H, CH$_2$O), 6.62 (br. s, 1H, NH), 7.28-7.81 (a series of m, 8H, fulvene), yield = 67%, $t_R$ = 4.50 min, (M$^+$ + 1) = 353.45. |
| (sec-butyl) | $^1$H NMR δ (CDCl$_3$): 0.72-0.90 (br. peak, 3H, CH$_3$), 1.0-1.40 (br. peak, 4H, CH$_2$), 1.48-1.90 (three br. peaks, 2H, CH$_2$), 2.68-2.80 (t, 1H, CH$_2$N), 3.10-3.70 (four br. peaks, 4H, CH$_2$O, CHN, and CH$_2$N), 4.15-4.25 (br. peak, 1H, CH), 4.54-4.62 (br. d, 2H, CH$_2$O), 7.25-7.80 (a series of m, 8H, fulvene), yield = 72%, $t_R$ = 5.77 min, (M$^+$ + 1) = 408.95. |
| NHTrt (with C=O) | $^1$H NMR δ (CDCl$_3$): 2.50-3.38 (four overlapping br. m, 7H, CH$_2$—CO, CH$_2$N, CH$_2$O, and CHN), 3.42-3.64 (m, ½H, CHN), 3.70-3.88 (m, ½H, CHN), 4.16-4.23 (br. d, 1H, CH), 4.48-4.68 (br. m, 2H, CH$_2$O), 4.94-5.05 (br. d, 1H, NH), 6.95-7.80 (a series of m, 23H, fulvene and Trt), yield = 83%, $t_R$ = 7.04 min, (M$^+$ + 1) = 652.61. |
| NHTrt (longer chain with C=O) | $^1$H NMR δ (CDCl$_3$): 1.67-1.78 (br. m, 1H, CH$_2$), 1.81-2.0 (br. m, 1H, CH$_2$), 2.10-2.43 (br. m, 2H, CH$_2$—CO), 2.58-2.81 (br. m, 2H, CH$_2$N), 3.02-3.66 (a series of br. m, 4H, CH$_2$O, and CHN), 4.17-4.23 (br. m, 1H, CH), 4.40-4.80 (br. m, 2H, CH$_2$O), 7.15-7.80 (a series of m, 23H, fulvene, and Trt), yield = 80%, $t_R$ = 7.04 min, (M$^+$ + 1) = 666.66. |
| NHPbf, =NH, HN (guanidine side chain) | $^1$H NMR δ (CDCl$_3$): 1.43 (s, 6H, CH$_3$), 1.50-1.60 (br. m, 4H, CH$_2$), 2.10 (s, 3H, CH$_3$), 2.48 (s, 3H, CH$_3$), 2.55 (s, 3H, CH$_3$), 2.92 (s, 2H, CH$_2$), 3.08-3.47 (two m, 3H, CH$_2$O, and CH$_2$N), 3.57-3.97 (a series of m, 3H, CH$_2$O,and CHN), 4.15-4.25 (br. m, 1H, CH), 4.44-4.74 (br. m, 2H, CH$_2$), 7.20-7.80 (a series of br. m, 8H, fulvene), yield = 91%, $t_R$ = 6.05 min, (M$^+$ + 1) = 704.71. |
| Imidazole-Trt | $^1$H NMR δ (CDCl$_3$): 2.14-2.56 (two m, 2H, CH$_2$-Im), 2.90-3.90 (a series of m, 4H, CH$_2$N, and CH$_2$O), 4.0-4.74 (a series of m, 4H, CHN, CH, CH$_2$), 7.0-7.80 (a series of multiples, 25H, fulvene, Im, and Trt), yield = 64%, $t_R$ = 5.27 min, (M$^+$ + 1) = 675.08. |
| O$^t$Bu (tyrosine-like) | $^1$H NMR δ (CDCl$_3$): 1.29 (s, 9H, $^t$Bu) 2.47-2.74 (a series of m, 2H, CH$_2$Ph), 2.90-3.04 (m, 1H, CH$_2$Ph), 3.06-3.45 (three m, 6H, CH$_2$O, and CH$_2$N), 3.89-4.29 (three m, 2H, CH, and CHN), 4.32-4.42 (m, 1H, CHN), 4.56-4.66 (m, 2H, CH$_2$), 6.81-7.80 (a series of m, 12 H, fulvene, and Ph), yield = 71%, (M$^+$ + 1) = 515.81. |
| OtBu | $^1$H NMR δ (CDCl$_3$): 1.00 & 1.10 (two s, 9H, $^t$Bu), 3.0-3.74 (four br. m, 7H, CH$_2$O, CH$_2$N, and CHN), 3.86-4.26 (a series of m, 2H, CHN, and CH), 4.42-4.68 (br. d, 2H, CH$_2$), 7.26-7.80 (a series of br. m, 8H, fulvene), yield = 55%, (M$^+$ + 1) = 439.08. |

Synthesis of 4-Fmoc-5-substituted-6-oxo-piperazine-2-carboxylic acid (7): Compounds (7) were prepared as described in method A. Compounds (7) were purified by silica gel column chromatography.

| R | Analytical Data for Compounds (7) |
|---|---|
| CH$_3$ | $^1$H NMR δ (CDCl$_3$): 1.08-1.20 (br. peak, 1.5H, CH$_3$), 1.30-1.38 (br. peak, 1.5H, CH$_3$), 2.86-3.07 (br. m, 1H, CH$_2$N), 3.83-3.97 (br. m, 1H, CH$_2$N), 4.18-4.37 (a series of br. peaks, 2H, CH and CHN), 4.40-4.74 (two br. peaks, 3H, CH$_2$O, and CHN), 7.28-7.82 (a series of m, 8H, fulvene), 8.92-9.10 (br. s, 1H, CO$_2$H), yield = 51%, $t_R$ = 4.80 min, (M$^+$ + 1) = 381.57. |
| (isobutyl) | $^1$H NMR δ (CDCl$_3$): 0.40-1.60 (a series of br. peaks, 9H, CH, CH$_2$, and CH$_3$), 2.81-3.09 (br. peak, 1H, CH$_2$N), 3.68-3.80 (br. peak, 2H, CHN), 3.96-4.32 (br. peaks, 2H, CH, and CNH), 4.48-4.68 (br. peak, CH$_2$O), 7.26-7.84 (a series of m, 8H, fulvene), yield = 50%, $t_R$ = 5.57 min, (M$^+$ + 1) = 423.15. |
| H | $^1$H NMR δ (CDCl$_3$): 3.77-3.99 (m, 1H, CHN), 3.90-4.35 (a series of m, 5H, CH$_2$N, CH), 4.44-4.57 (d, 2H, CH$_2$), 7.3-7.82 (a series of m, 8H, fulvene), yield = 48%, $t_R$ = 4.58 min, (M$^+$ + 1) = 367.30. |

-continued

| R | Analytical Data for Compounds (7) |
|---|---|
| ![structure] branched alkyl | $^1$H NMR δ (CDCl$_3$): 0.69-1.90 (a series of br. peaks, CH$_2$, and CH$_3$), 2.85-3.05 (br. peak, 2H, CH$_2$N), 3.65-3.95 (two br. peaks, 1H, CHN), 4.00-4.40 (two br. peaks, CH$_2$N, and CH), 4.41-4.74 (br. peak, 3H, CH$_2$O, and CHN), 7.20-7.80 (a series of br. m, 8H, fulvene), yield = 70%, $t_R$ = 5.93 min, (M$^+$ + 1) = 423.42. |
| CH$_2$CH(NHTrt)C(O)— | $^1$H NMR δ (CDCl$_3$): 2.51-3.06 (a series of m, 2H, CH$_2$—CO), 3.85-4.86 (a series of m, 7H, CH$_2$N, CHN, CH, and CH$_2$O), 7.0-7.78 (a series of br. m, 23H, fulvene and Trt), yield = 30%, $t_R$ = 7.04 min, (M$^+$ + 1) = 666.79. |
| (CH$_2$)$_2$CH(NHTrt)C(O)— | $^1$H NMR δ (CDCl$_3$): 1.74-2.46 (a series of br. m, 4H, CH$_2$—CO, and CH$_2$), 3.78-4.06 (two m, 2H, CH$_2$N), 4.16-4.68 (a series of br. m, 5H, CHN, CH, and CH$_2$O), 7.14-7.82 (a series of br. m, 23H, fulvene, and Trt), yield = 47%, $t_R$ = 7.11 min, (M$^+$ + 1) = 680.33. |
| —(CH$_2$)$_3$NHC(=NH)NHPbf | $^1$H NMR δ (CDCl$_3$): 1.08-1.60 (a series of br. peaks, 8H, CH$_2$, and CH$_3$), 2.12 (s, 3H, CH$_3$), 2.48 (s, 3H, CH$_3$), 2.57 (s, 3H, CH$_3$), 2.92 (s, 2H, CH$_3$), 3.10-3.25 (br. m, 2H, CH$_2$N), 3.82-4.28 (a series of br. m, 4H, CH$_2$N, CHN, CH), 4.40-4.70 (br. m, 3H, CHN, and CH$_2$O), 7.20-7.80 (a series of br. m, 8H, fulvene), yield = 42%, $t_R$ = 6.15 min, (M$^+$ + 1) = 718.69. |
| —CH$_2$-C$_6$H$_4$-O$^t$Bu | $^1$H NMR δ (CDCl$_3$): 1.28 & 1.34 (two s, 9H, $^t$Bu), 2.42-3.64 (a series of br. m, 5H, CH$_2$N, CHN, and CH$_2$Ph), 4.0-4.76 (a series of br. m, 4H, CHN, CH, and CH$_2$O), 6.60-6.96 (br. m, 4H, Ph), 7.20-7.80 (a series of br. m, 8H, fulvene), yield = 67%, (M$^+$ + 1) = 529.17. |
| —CH$_2$-OtBu | $^1$H NMR δ (CDCl$^3$): 0.96- & 1.10 (two s, 9H, $^t$Bu), 3.04-3.18 (br. m, 0.5H, CH$_2$N), 3.30-3.94 (four br. m, 3.5H, CH$_2$N, and CH$_2$O), 3.98-4.32 (br. m, 2H, CH, and CHN), 4.33-4.74 (two br. m, 3H, CHN, CH$_2$O), 7.28-7.80 (a series of m, 8H, fulvene), yield = 60%, (M$^+$ + 1) = 453.37. |

Method E: (2-Fmoc-amino-3-hydroxy-propyl-Cbz-amino)-2-substituted acetic acid methyl ester (15) were prepared by reductive amination of Fmoc serinal (OR') (9) with an α amino ester (2), using either sodium cyanoborohydride or sodium triacetoxyborohydride as the reducing agent. The secondary amine was protected with benzylchloroformate, and then the hydroxyl group deprotected with trifluoroacetic acid solution. Compounds (15) were then Fmoc deprotected. The amino ester intermediates cyclized immediately to form 4-Cbz-3-substituted 6-hydroxymethyl-piperazin-2-ones (16). Fmoc 3-substituted 6-hydroxymethyl-piperazin-2-ones (6) were prepared by protecting group exchange, and then oxidized to the desired products (7) as described in method A.

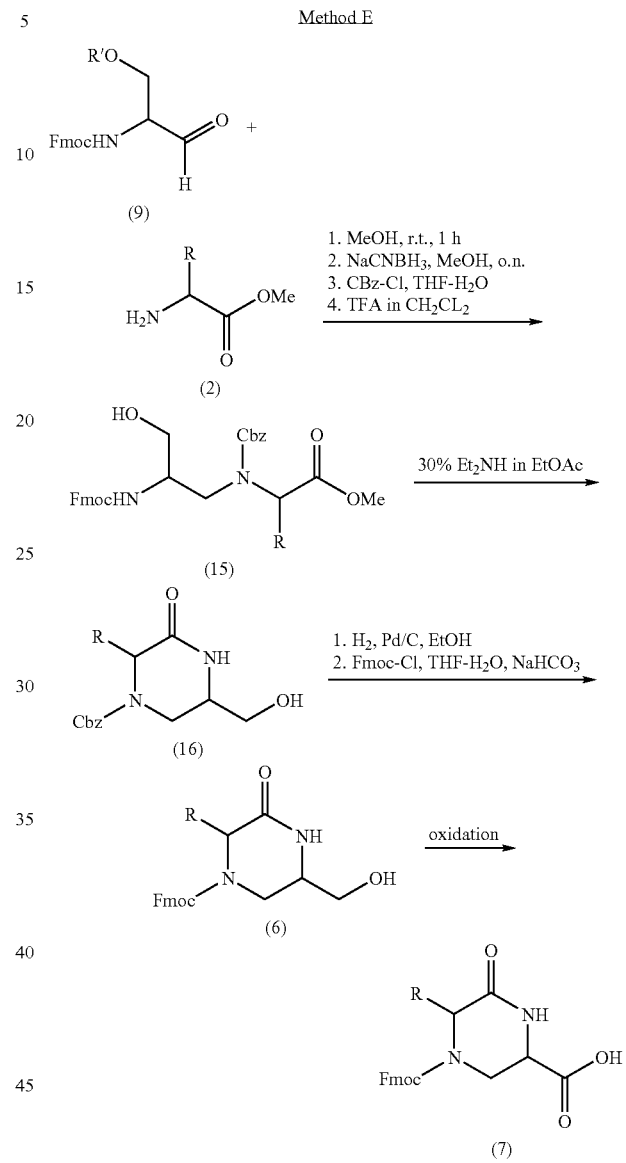

Method E

Synthesis of (2-Fmoc-amino-3-hydroxy-propyl-Cbz-amino)-2-substituted acetic acid methyl ester (15): A suspension of 67 mmol of amino ester hydrochloride (2), and 20.9 mmol of solid potassium hydroxide in 80 mL of methanol was stirred at room temperature for 25 minutes, and then added to a suspension of (9) in 250 mL of methanol. The reaction mixture was stirred for 1.5 hours, followed by the slow addition of 70 mL of 1N sodium cyanoborohydride solution in tetrahydrofuran. The reaction was stirred overnight, and then concentrated. The residue was partitioned between 300 mL of tetrahydrofuran and 50 mL of 1N hydrochloric acid solution. The layers were separated, and the organic layer neutralized with a solution of 239 mmol of sodium bicarbonate in 50 mL of water, and then 66 mmol of benzyl chloroformate was added slowly, and the reaction was stirred for 3 hours, diluted with 200 mL of ethyl acetate, and the layers separated. The organic layer was dried over magnesium sulfate, and concentrated. The residue was dissolved in a solution of trifluoroacetic acid in dichloromethane, and stirred at room temperature for 2 hours. The solution was poured over 200 mL of saturated sodium bicarbonate solution. The layers separated, and the organic layer was dried over magnesium sulfate, and concentrated. Compounds (15) were purified by silica gel column chromatography.

| R | Analytical Data for Compounds (15) |
|---|---|
|  | $^1$H NMR δ (CDCl$_3$): 1.38-1.45 (d, 9H, $^t$Bu), 2.68-2.78 (m, ½H, CH$_2$—CO), 3.0-3.20 (m, and s together, 3.5H, CH$_2$—CO, CH$_2$—O, and CH$_3$—O), 3.52-3.60 (m, 1H, CH$_3$—O), 3.96-4.40 (a series of multiples, 4H), 4.96-5.10 (m, 2H, CH$_2$—O), 5.77-5.83 (m, ½H, NH), 7.14-7.79, (a series of m, 23H, Trt and fulvene), yield = 70%, $t_R$ = 9.82 min. |

Synthesis of 4-Cbz-6-hydroxymethyl-3-substituted-piperazin-2-ones (16): A solution of 24 mmol of (15) in 100 mL of 30% diethyl amine in ethyl acetate was stirred at room temperature overnight, and then concentrated to dryness. The compounds were purified by silica gel column chromatography.

| R | Analytical Data for Compounds (16) |
|---|---|
| 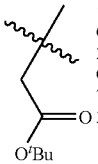 | $^1$H NMR δ (CDCl$_3$): 1.36 (d, 9H, $^t$Bu), 2.60-2.90 (m, 2H, CH$_2$—CO), 2.94-3.20 (br. m, 2H, CH$_2$N, 3.38-3.50 (br. m, 2H, CH$_2$—O), 3.86-4.20 (m, 1H, CH—N), 4.74-4.84 (br, 1H, OH), 5.10-5.15 (s, 2H, CH$_2$—O), 7.26-7.36 (s, 5H, Ph), 7.87-7.95 (s, 1H, NH), yield = 70%, $t_R$ = 4.66 mm, (M$^+$ + 1) = 379.41. |

Synthesis of 4-Fmoc-6-hydroxymethyl-3-substituted-piperazin-2-ones (6): A suspension of 15 mmol of (16), and 1.8 g of 10% palladium on carbon in 50 mL of ethanol was hydrogenated at room temperature and atmospheric pressure until HPLC showed that the reaction was complete. The mixture was then filtered through celite, concentrated, and the residue was dissolved in 35 mL of tetrahydrofuran, and 10 mL of water, and then 62 mmol of solid sodium bicarbonate was added, followed by 16 mmol of Fmoc-Cl, and the mixture was stirred for 3 hours, diluted with 100 mL of ethyl acetate and 10 mL of water. The layers were separated, and the organic layer dried over magnesium sulfate, and concentrated. Compounds (6) were purified by silica gel column chromatography.

| R | Analytical Data for Compounds (6) |
|---|---|
|  | $^1$H NMR δ (CDCl$^3$): 1.41 (s, 9H, $^t$Bu), 2.20-2.40 (m, ½H, CH$_2$—CO), 2.64-2.96 (m, 1.5H, CH$_2$—CO), 2.98-3.16 (m, 1H, CH$_2$O), 3.2-3.8 (a series of br. m, 4H, CH$_2$O and CH$_2$N), 4.20-4.38 (two m, CHN, and CH), 4.5-4.67 (br. m, 2H, CH$_2$O), 4.70-4.83 (br. m, ½H, NH), 7.27-7.84 (a series of m, 8H, fulvene), yield = 77%, $t_R$ = 5.78 min, (M$^+$ + 1) = 467.82. |

Synthesis of 4-Fmoc-5-substituted-6-oxo-piperazine-2-carboxylic acid (7): Compounds (7) were prepared as described in method A, and purified by silica gel column chromatography.

| R | Analytical Data for Compounds (7) |
|---|---|
| 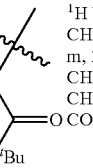 | $^1$H NMR δ (CDCl$_3$): 1.4 (s, 9H, $^t$Bu), 2.20-2.33 (br. d, 1H, CH$_2$—CO), 2.55-2.67 (br. d, 1H, CH$_2$—CO), 3.25-3.52 (br. m, 2H, CH$_2$N), 3.82-3.94, and 4.07-4.18 (br. peaks, 1H, CHN), 4.20-4.42 (m, 2H, CHN, CH), 4.50-4.72 (m, 2H, CH$_2$—O), 7.30-7.82 (8H, fulvene), 9.20-9.35 (br. s, 1H CO$_2$H), yield = 63%, $t_R$ = 6.60 min, (M$^+$ + 1) = 481.17. |

Method F: (2-Cbz-amino-3-benzyloxy-propylamino)-2-substituted acetic acid methyl esters (20) were prepared by reductive amination of Cbz serinal (OBn) (19) with an α-amino ester (2), using either sodium cyanoborohydride or sodium triacetoxyborohydride as the reducing agent. The Cbz O-Benzyl serinal (19) required for the reductive amination was obtained by oxidation of Cbz serinol (OBn) (18) with Dess-Martin periodinane. Hydrogenation of (20) followed by cyclization gave 3-substituted 6-hydroxymethyl-piperazin-2-ones which was then Fmoc protected to 4-Fmoc-3-substituted 6-hydroxymethyl-piperazin-2-ones (6). The final products (7) were obtained as described in method A.

Method F

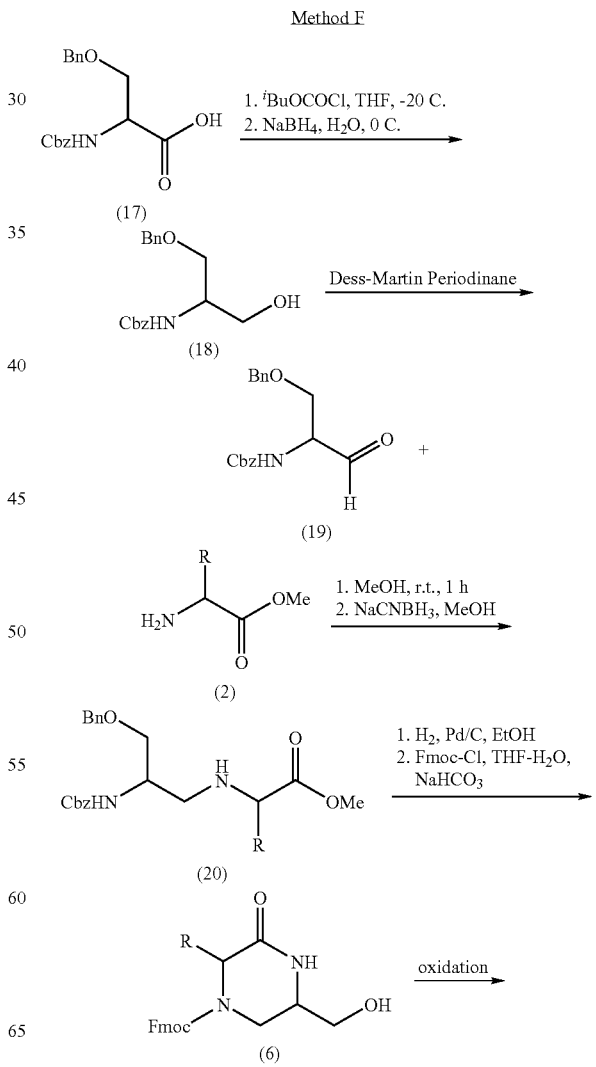

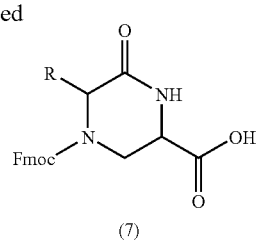

(7)

Synthesis of Cbz-serinol (OBn) (18): Compound (18) was prepared as described for compound (13). Compound (18) was obtained in 79% yield after silica gel column chromatography purification. $^1$H NMR δ (CDCl$_3$) 3.57-3.74 (two m, 3H, CHN, and CH$_2$O), 3.76-3.96 (two m, 2H, CH$_2$O), 4.50 (s, 2H, CH$_2$O), 5.10 (s, 2H, CH$_2$O), 5.40-5.50 (br. d, 1H, NH), 7.22-7.38 (m, 10H, Ph); HPLC t$_R$=5.33 min, (M$^+$+Na$^+$)=337.64.

Synthesis of Cbz serinal (OBn) (19): Compound (19) was prepared as described for compound (9). To a solution of 80 mmol of Cbz-O-Bn serinol (18) in 200 mL of dry dichloromethane, kept at room temperature under nitrogen, was added 88 mmol of Dess-Martin periodinane, and the reaction stirred for 2.5 hours, and then quenched by addition of 400 mL of 10% aqueous sodium thiosulfate solution. The layers were separated, and the organic layer concentrated, diluted with 300 mL of ethyl ether, and washed three times with a saturated aqueous bicarbonate solution containing 10% sodium thiosulfate, dried over magnesium sulfate, and concentrated. Compound (19) was obtained in 99% crude yield, and used without further purification. $^1$H NMR δ (CDCl$_3$) 3.69-3.78 (dd, 1H, CH$_2$O), 3.99-4.06 (dd, 1H, CH$_2$O), 4.37-4.46 (m, 1H, CHN), 4.47-4.52 (d, 2H, CH$_2$O), 5.14 (s, 2H, CH$_2$O), 5.65-5.75 (br. d, 1H, NH), 7.14-7.48 (a series of m, 9H, Ph), 7.98-8.08 (dd, 1H, Ph), 9.63 (s, 1H, CHO).

Synthesis of (2-Cbz-amino-3-benzyloxy-propylamino)-2-substituted acetic acid methyl esters (20): Compounds (20) were prepared as described for compound (10), but using Cbz serinal (19) as the aldehyde. Compounds (20) were purified by silica gel column chromatography.

| R | Analytical Data for Compounds (20) |
|---|---|
| ![benzyl-OtBu] | $^1$H NMR δ (CDCl$_3$): 1.30 (s, 9H, $^t$Bu), 2.50-2.96 (m, 3H, CH$_2$Ph, and CH$_2$N), 3.28-3.54 (m, 3H, CH$_2$N, and CH$_2$O), 3.59 and 3.61 (two s, 3H, CH$_3$O), 3.68-3.86 (m, 1H, CHN), 4.41-4.45 (d, 2H, CH$_2$O), 5.08 (s, 2H, CH$_2$O), 5.25-5.37 (br. t, 1H, NH), 6.84-6.88 (d, 2H, Ph), 6.98-7.04 (d, 2H, Ph), 7.24-7.37 (m, 10H, Ph), yield = 50%, (M$^+$ + 1) = 549.35. |

Synthesis of 4-Fmoc-6-hydroxymethyl-3-substituted-piperazin-2-ones (6): A suspension of 38 mmol of (20) in 160 mL of ethanol, 38 mL of 1N hydrochloric acid, and 20 g of 10% palladium on carbon was hydrogenated at room temperature and atmospheric pressure until HPLC showed that the reaction was complete. The mixture was then filtered through celite, and concentrated to dryness. The residue was diluted with 75 mL of tetrahydrofuran and neutralized with a saturated sodium bicarbonate solution. 106 mmol of solid sodium bicarbonate, and 53 mmol of Fmoc chloride were added, and the reaction stirred at room temperature until HPLC showed the reaction was complete, diluted with 300 mL of ethyl acetate and 300 mL of brine. The layers were separated, and the organic layer washed twice with brine, dried over magnesium sulfate, and concentrated. The products (6) were purified by silica gel column chromatography.

Synthesis of 4-Fmoc-5-substituted-6-oxo-piperazine-2-carboxylic acid (7): Compounds (7) were prepared as described in method A.

Synthesis of 2,2-disubstituted Ketopiperazine Scaffolds Mimicking Amino Acids without Functionalized Side Chains (Method G)

The syntheses of 4-Fmoc-5-substituted-6-oxo-piperazine-2-methyl-2-carboxylic acid scaffolds mimicking amino acids without functionalized side chains was carried out using method G. 2-Boc-amino-3-(methoxycarbonyl-1-substituted-methylamino-2-methyl-propionic acid tert-butyl esters (23) were prepared by reductive amination of 2-Boc-amino-2-methyl-3-oxo-propionic acid methyl ester (22) with an α-amino ester (2), using either sodium cyanoborohydride or sodium triacetoxyborohydride as the reducing agent. Compound (22) required for the reductive amination was obtained by oxidation of α-methyl-Boc serine tert-butyl ester (21) with Dess-Martin periodinane. The Boc group of (23) was removed with 2N hydrogen chloride in dioxane, and the amino esters cyclized to unprotected 5-substituted-6-oxo-piperazine-2-methyl-2-carboxylic acid tert-butyl esters (24), which were protected with Fmoc chloride to give 4-Fmoc-5-substituted-6-oxo-piperazine-2-methyl-2-carboxylic acid tert-butyl esters, which were deprotected with trifluoroacetic acid to give the final products (25).

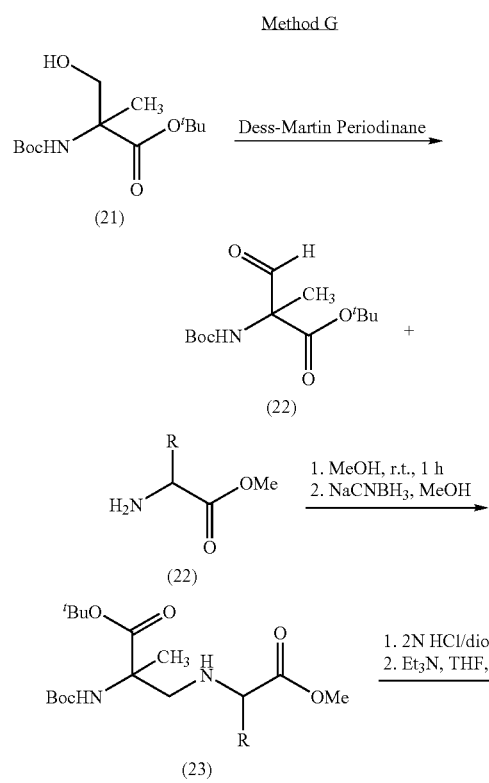

-continued

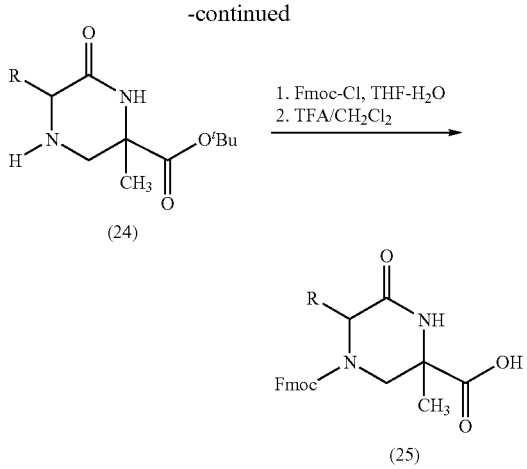

(24)

1. Fmoc-Cl, THF-H$_2$O
2. TFA/CH$_2$Cl$_2$ (25)

Synthesis of 2-Boc-amino-2-methyl-3-oxo-propionic acid tert-butyl ester (22): Oxidation of Boc α-Methyl serine tert-butyl ester (21) was done using Dess-Martin periodinane as describe before gave the desired product (22) in 96% crude yield. The compound was used without further purification in the next step. $^1$H NMR δ (CDCl$_3$): 1.44 (s, 18H, $^t$Bu), 1.46 (s, 3H, CH$_3$), 5.63-5.70 (br. s, 1H, NH), 9.5 (s, 1H, CHO)

Synthesis of 2-Boc-amino-3-(methoxycarbonyl-1-substituted-methylamino-2-methyl-propionic acid tert-butyl ester (23): Compounds (23) were prepared using a procedure similar to the one described for compound (10), but using compound (22) as the aldehyde. Compounds (23) were purified by silica gel column chromatography.

| R | Analytical Data for Compounds (23) |
|---|---|
| 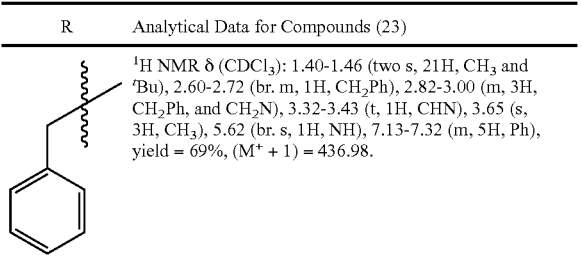 | $^1$H NMR δ (CDCl$_3$): 1.40-1.46 (two s, 21H, CH$_3$ and $^t$Bu), 2.60-2.72 (br. m, 1H, CH$_2$Ph), 2.82-3.00 (m, 3H, CH$_2$Ph, and CH$_2$N), 3.32-3.43 (t, 1H, CHN), 3.65 (s, 3H, CH$_3$), 5.62 (br. s, 1H, NH), 7.13-7.32 (m, 5H, Ph), yield = 69%, (M$^+$ + 1) = 436.98. |

Synthesis of 2-methyl-6-oxo-5-substituted-piperazine-2-carboxylic acid (25): A solution of 4 mmol of (23) in 8 mL of 2N hydrogen chloride in dioxane was stirred at room temperature for 5 hours, and then concentrated to dryness. The residue was suspended in 20 mL of tetrahydrofuran, neutralized with 10 mmol of triethylamine, and stirred at 60° C. for 2 days. It was then concentrated to dryness, resuspended in 20 mL of tetrahydrofuran and 10 mL of water, solid sodium bicarbonate was added to adjust the pH to basic, followed by 5.6 mmol of solid Fmoc chloride, and the reaction mixture stirred overnight at room temperature, the pH adjusted to 1 with 1N hydrochloric acid solution, diluted with 100 mL of ethyl acetate, and the layers separated. The organic layer was washed with 2×100 mL of brine, dried over magnesium sulfate and concentrated. The residue was dissolved in 10 mL of 50% trifluoroacetic acid in dichloromethane, and the solution stirred at room temperature for 3 hours. The solvent was concentrated, and the products (25) purified by silica gel column chromatography.

| R | Analytical Data for Compounds (25) |
|---|---|
| 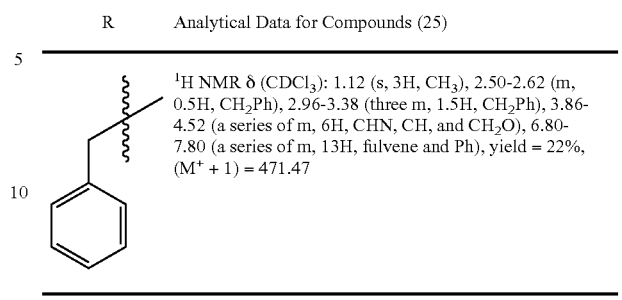 | $^1$H NMR δ (CDCl$_3$): 1.12 (s, 3H, CH$_3$), 2.50-2.62 (m, 0.5H, CH$_2$Ph), 2.96-3.38 (three m, 1.5H, CH$_2$Ph), 3.86-4.52 (a series of m, 6H, CHN, CH, and CH$_2$O), 6.80-7.80 (a series of m, 13H, fulvene and Ph), yield = 22%, (M$^+$ + 1) = 471.47 |

Synthesis of 2,2-disubstituted Ketopiperazine Scaffolds Mimicking Amino Acids with Functionalized Side Chains (Method H)

The syntheses of 4-Fmoc-5-substituted-6-oxo-piperazine-2-methyl-2-carboxylic acid scaffolds mimicking amino acids with functionalized side chains are performed using method H. 2-Alloc-amino-3-(methoxycarbonyl-1-substituted-methylamino-2-methyl-propionic acid methyl ester (30) is prepared by reductive amination of 2-Alloc-amino-2-methyl-3-oxo-propionic acid methyl ester (28) with an α-amino allyl ester (29), using either sodium cyanoborohydride or sodium triacetoxyborohydride as the reducing agent, followed by protection of the secondary amine with benzylchloroformate. Compound (28) required for the reductive amination is obtained by oxidation of (27) with Dess-Martin periodinane. The allyl ester and the alloc groups of analogs (30) are removed using tetrakistriphenyl phosphine palladium (0) and the amino acid cyclized by reaction with a peptide coupling reagent to give 5-substituted-6-oxo-piperazine-2-methyl-2-carboxylic acid methyl esters (31). 4-Fmoc-5-substituted-6-oxo-piperazine-2-methyl-2-carboxylic acids (25) are obtained by saponification of the methyl ester, followed by protecting group exchange.

Method H

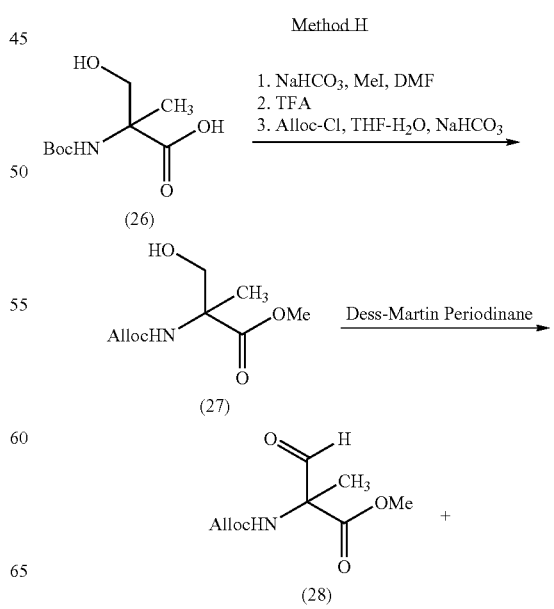

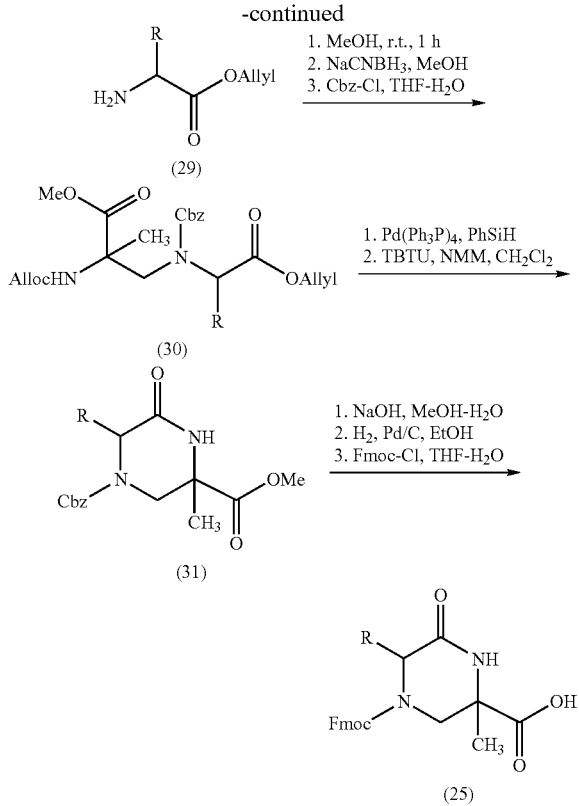

Synthesis of Alloc α-methyl serine methyl ester (27): A solution of 8 mmol of Boc α-methyl serine (26), 1.0 g (12 mmol) of solid sodium bicarbonate, and 1.0 mL (16 mmol) of iodomethane in 8 mL of dry dimethylformamide, kept under nitrogen is stirred overnight. The reaction mixture is then poured over 50 mL of water, and extracted with 50 mL of diethyl ether, and washed with 1×20 mL of water, dried over magnesium sulfate, and concentrated. The residue is dissolved in 20 mL of 90% trifluoroacetic acid in dichloromethane, and the solution is stirred at room temperature for 3 hours, and then concentrated to dryness. The residue is dissolved in 35 mL of tetrahydrofuran, and 10 ml of water, followed by addition of 30 mmol of solid sodium bicarbonate, and the slow addition of 12 mmol of allyl chloroformate. The mixture is stirred at room temperature for 2 hours, diluted with 50 mL of ethyl acetate, and the layers separated. The organic layer is then washed with 1×10 mL of saturated sodium bicarbonate, and 1×10 ml of 1N hydrochloric acid, and 1×10 mL of water, dry over magnesium sulfate, and concentrated. Compound (27) is purified by silica gel column chromatography.

Synthesis of 2-Alloc-amino-2-methyl-3-oxo-propionic acid methyl ester (28): Oxidation of Alloc α-methyl serine methyl ester (27) is done using Dess-Martin periodinane as described above to yield the desired product (28).

Synthesis of 2-Alloc-amino-3-(methoxycarbonyl-1-substituted-methyl-Cbz-amino-2-methylpropionic acid allyl ester (30): Compounds (30) are prepared using a procedure similar to the one described for compounds (15), but using compound (28) as the aldehyde.

Synthesis of 4-Cbz-2-methyl-6-oxo-5-substituted-piperazine-2-carboxylic acid methyl ester (31): To solution of 10 mmol of compound (30) in 30 mL of dichloromethane, kept at room temperature under nitrogen, is added 2 equivalents of phenylsilane and 0.3 equivalents of tetrakistriphenylphosphine palladium (0), and the solution stirred for 2 hours, and then 11 mmol of TBTU, and 14 mmol of N-methyl-morpholine are added, and the solution stirred at room temperature for 2 hours, and then concentrated to dryness.

Synthesis of 4-Fmoc-2-methyl-6-oxo-5-substituted-piperazine-2-carboxylic acid (25): To a solution of 10 mmol of compound (31) in 25 mL of methanol, kept at room temperature under nitrogen, is added slowly 11 mmol of 1N sodium hydroxide solution, and the reaction is stirred at room temperature overnight, neutralized with 21 mL of 1N hydrochloric acid solution, 1 g of 10% palladium on carbon is added, and the suspension hydrogenated at room temperature and atmospheric pressure for 3 hours. The suspension is filtered through celite and concentrated. The residue is redissolved in 25 mL of tetrahydrofuran, and 10 mL of water, followed by the addition of 30 mmol of solid sodium bicarbonate, and 10 mmol of Fmoc chloride, and the reaction is stirred at room temperature under nitrogen for 2 hours. The reaction is then diluted with 50 mL of ethyl acetate, and acidified with 1N hydrochloric acid solution. The layers are then separated, and the organic layer is washed with 1×20 mL of water, dried over magnesium sulfate, and concentrated. Compounds (25) are purified by silica gel column chromatography.

Synthesis of (5-substituted-6-oxo-piperazin-2-yl)-acetic acid Scaffolds (Methods I, J, K)

The syntheses of (5-substituted-6-oxo-piperazin-2-yl)-acetic acid scaffolds were carried out by several methods.

Method I: (tert-butyl 3-protected-amino-4-(methoxycarbonyl-substituted-methylamino)-butyrates (35) were prepared by reductive amination of tert-butyl 3-protected-amino-4-oxo-butyrate (34) with α-amino esters (2), using either sodium cyanoborohydride or sodium triacetoxyborohydride as the reducing agent. The tert-butyl 3-protected-amino-4-oxo-butyrate (34) required for the reductive amination was prepared by lithium aluminum hydride (LAH) reduction of the Weinreb amide derivatives (33). Tert-butyl (3-protected-amino-4-(methoxycarbonyl-substituted-methylamino)-butyrate analogs (35) were then deprotected, cyclized, and Fmoc protected to give tert-butyl (5-substituted-6-oxo-piperazin-2-yl)-acetates (36), which were then deprotected to give the final products (37).

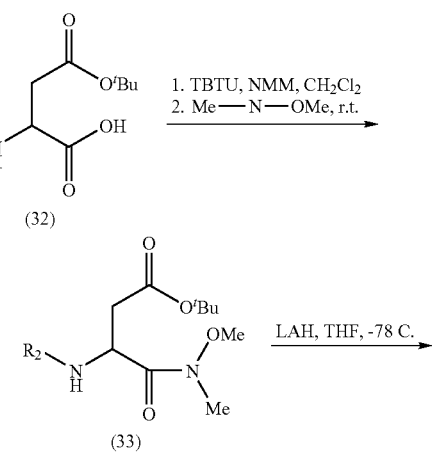

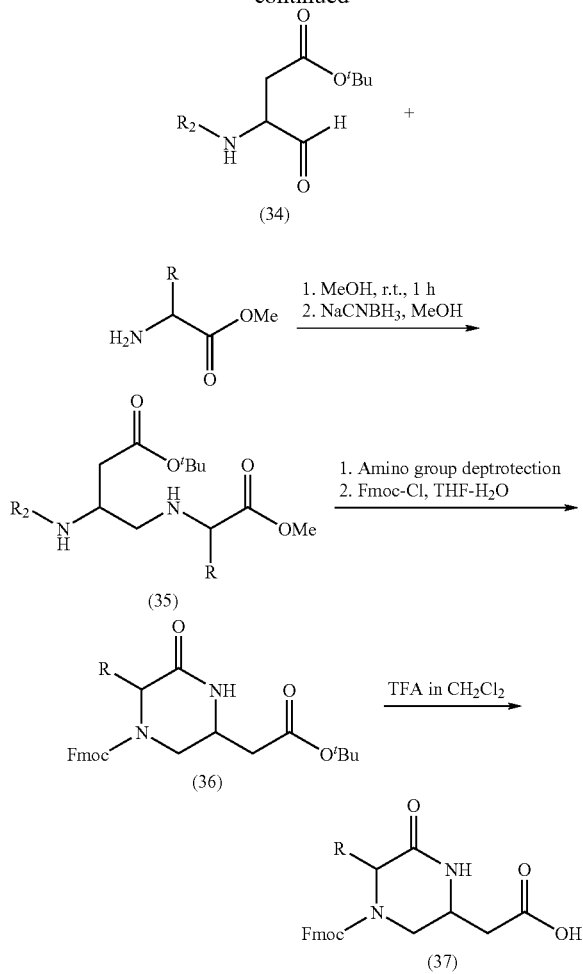

(34)

(35)

(36)

(37)

Synthesis of amino protected Asp-(O$^t$Bu) Weinreb amide (33): Compounds (33) were prepared using a procedure similar to the one described for compound (14).

| R$_2$ | Analytical Data for Compounds (33) |
|---|---|
| Cbz | $^1$H NMR δ (CDCl$_3$): 1.40 (s, 9H, $^t$Bu), 2.47-2.59 (dd, 1H, CH$_2$CO), 3.20 (s, 3H, CH$_2$N), 3.77 (s, 3H, CH$_3$O), 4.96-5.05 (br. m, 1H, CHN), 5.05-5.12 (br. d, 2H, CH$_2$O), 5.58-5.66 (br. d, 1H, NH), 7.30-7.36 (br. m, 5H, Ph), yield = 90% |
| Fmoc | $^1$H NMR δ (CDCl$_3$): 1.45 (s, 9H, $^t$Bu), 2.55-2.64 (dd, 1H, CH$_2$CO), 2.69-2.80 (dd, 1H, CH$_2$O), 3.60 (s, 3H, CH$_3$N), 3.79 (s, 3H, CH$_3$O), 4.18-4.26 (t, 1H, CH), 4.32-4.40 (d, 2H, CH$_2$O), 4.98-5.19 (m, 1H, CHN), 5.70-5.76 (br. d, 1H, NH), 7.35-7.80 (a series of m, 8H, fulvene), yield = quant. |

Synthesis of tert-butyl 3-amino protected-amino-4-oxo-butyrate (34): Compounds (34) were prepared using a procedure similar to the one described for compound (9).

| R$_2$ | Analytical Data for Compounds (34) |
|---|---|
| Cbz | $^1$H NMR δ (CDCl$_3$): 1.40 (s, 9H, $^t$Bu), 2.69-2.81 (dd, 1H, CH$_2$CO), 2.89-3.01 (dd, 1H, CH$_2$CO), 4.33-4.42 (m 1H, CHN), 5.12 (s, 2H, CH$_2$O), 5.83-5.88 (br. d, 1H, NH), 7.31-7.39 (br. m, 5H, Ph), 9.64 (s, 1H, CHO) |
| Fmoc | $^1$H NMR δ (CDCl$_3$): 1.45 (s, 9H, $^t$Bu), 2.58-3.02 (a series of m, 2H, CH$_2$CO), 4.20-4.28 (t, 1H, CH), 4.35-4.49 (m, 3H, CH$_2$O, and CHN), 5.85-5.92 (br. d, 1H, NH), 7.27-7.80 (a series of m, 8H, fulvene), 9.65 (s, 1H, CHO) |

Synthesis of tert-butyl 3-Protected-amino-4-(methoxycarbonyl-substituted-methylamino)-butyrate (35): Compounds (35) were prepared using a procedure similar to the one described for compounds (10), but using compounds (34) as the aldehyde.

| R$_2$ | R | Analytical Data for Compounds (35) |
|---|---|---|
| Cbz | 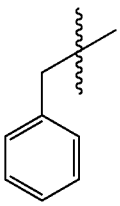 | $^1$H NMR δ (CDCl$_3$): 1.40 (s, 9H, $^t$Bu), 2.27-3.02 (a series of m, 6H, CH$_2$CO, CH$_2$Ph, and CH$_2$N), 3.43-3.52 (t, 1H, CHN), 3.65 (s, 3H, CH$_3$O), 3.84-3.98 (m, 1H, CHN), 5.08 (s, 2H, CH$_2$O), 5.33-5.44 (br. d, 1H, NH), 7.11-7.42 (a series of m, 10H, Ph), yield = 60%, t$_R$ = 4.79 min, (M$^+$ + 1) = 471.20. |
| Cbz | 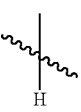 | $^1$H NMR δ (CDCl$_3$): 1.55 (s, 9H, $^t$Bu), 2.42-2.68 (br. m, 2H, CH$_2$N), 2.74-2.92 (two dd, 2H, CH$_2$O), 3.46-3.50 (d, 2H, CH$_2$N), 3.78 (s, 3H, CH$_3$O), 4.02-4.14 (m, 1H, CHN), 5.15 (s, 2H, CH$_2$O), 7.40-7.45 (m, 5H, Ph), t$_R$ = 3.82, (M$^+$ + 1) = 381.28 |
| Cbz | 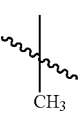 | $^1$H NMR δ (CDCl$_3$): 1.25-1.30 (d, 3H, CH$_3$), 1.44 (s, 9H, $^t$Bu) 2.38-2.65 (a series of m, 2H, CH$_2$CO), 2.66-2.85 (m, 2H, CH$_2$N), 3.60-3.70 (m, 1H, CHN), 3.7 (s, 3H, CH$_3$O), 3.9-4.1 (m, 1H, CHN), 5.1 (s, 2H, CH$_2$O), 5.4-5.6 (br. t, 1H, NH), 7.28-7.4 (m, 5H, Ph), t$_R$ = 3.81 min, (M$^+$ + 1) = 395.25. |

-continued

| R₂ | R | Analytical Data for Compounds (35) |
|---|---|---|
| Cbz | [structure] | ¹H NMR δ (CDCl₃): 0.84-0.91 (m, 6H, CH₃), 1.08-1.30 (m, 1H, CH), 1.45 (s, 9H, ᵗBu) 1.45-1.70 (m, 2H, CH₂), 2.39-2.60 (m, 3H, CH₂CO, CH₂N), 2.74-2.86 (dd, 1 H, CH₂N), 2.98-3.16 (dd, 1H, CHN), 3.7 (s, 3H, CH₃O), 3.92-4.08 (br. m, 1H, CHN), 5.1 (s, 2H, CH₂O), 7.26-7.45 (m, 5H, Ph), $t_R$ = 4.56 min, (M⁺ + 1) = 437.31. |

Synthesis of tert-butyl (4-Fmoc-5-substituted-6-oxo-piperazin-2-yl)-acetate (36): For compounds containing Fmoc amino protecting group, a solution of 10 mmol of compound (35) in 30 mL of 30% diethyl amine in ethyl acetate solution was stirred at room temperature overnight, and then concentrated to dryness. For compounds containing Cbz amino protecting group, a solution of 10 mmol of compound (35) in 30 mL of ethanol was hydrogenated at room temperature and atmospheric pressure for 2 hours, filtered through celite, and concentrated to dryness. For Fmoc protection, the residue was dissolved in 20 mL of tetrahydrofuran, and 10 mL of water, and 2.52 g (30 mmol) of solid sodium bicarbonate was added, followed by the addition of 3.3 g (13 mmol) of Fmoc-Cl. The mixture was stirred for 3 hours and diluted with ethyl acetate. The layers separated, and the organic layer was washed with water, dried over magnesium sulfate, and concentrated. Compounds (36) were purified by silica gel column chromatography.

| R | Analytical Data for Compounds (36) |
|---|---|
| [structure: benzyl] | ¹H NMR δ (CDCl₃): 1.44 (s, 9H, ᵗBu), 1.71-2.10 (m, 2H, CH₂CO), 2.10-2.30 (br. d, 1H, CHN), 2.62-2.82 (br. d, 1H, CH₂Ph), 2.90-3.74 (a series of br. m, 3H, CH₂N, CHN), 3.80-4.07 (br. d, 1H, CHN), 4.10-4.50 (br. m, 3H, CH₂O, and CH), 6.74-7.80 (a series of m, 23H, fulvene, and Ph), yield = 75%, $t_R$ = 7.15 min, (M⁺ + 1) = 527.20. |
| [structure] | ¹H NMR δ (CDCl₃): 0.77-1.94 (a series of m, and two s, 18H, ᵗBu, CH₂, and CH₃), 2.07-2.76 (three m, 3H, CH₂CO, and CHN), 2.86-3.80 (four m, 2H, CH₂N), 4.16-4.27 (m, 1H, CH), 4.30-4.43 (m, 1H, CHN), 4.50-4.70 (br. m, 2H, CH₂O), 7.26-7.79 (a series of m, 8H, fulvene), yield = 40% for three steps, $t_R$ = 7.31 min, (M⁺ + 1) = 493.47. |
| [structure with H] | ¹H NMR δ (CDCl₃): 1.45 (s, 9H, ᵗBu), 1.9-2.5 (m 2H, CH₂CO), 3.02-4.7 (a series of m, 8 H, CH, CH₂, CH₂N), 7.25-7.78 (three m, 8H, fulvene), $t_R$ = 6.42 min, (M⁺ + 1) = 431.31. |
| [structure with CH₃] | ¹H NMR δ (CDCl₃): 1.20-1.35 (br. m, 3H, CH₃), 1.45 (s, 9H, ᵗBu) 2.1-2.80 (three m, 3H, CH₂CO, CH₂N), 3.1-4.1 (four m, 3H, CH₂N, CHN), 4.18-4.26 (br. t, 1H, CH), 4.28-4.46 (br. m, 1H, CHN), 4.50-4.68 (br. m, 2H, CH₂), 7.28-7.8 (three m, 8H, fulvene), $t_R$ = 6.29 min, (M⁺ + 1) = 451.24. |

-continued

| R | Analytical Data for Compounds (36) |
|---|---|
| [structure] | ¹H NMR δ (CDCl₃): 1.20-1.60 (br. m, and s, 15H, CH₃, ᵗBu) 2.21-2.80(3 br. m, 2H, CH₂CO), 3.0-3.9 (four br. m, 2H, CH₂N), 4.18-4.26 (br. m, 2H, CH, CHN), 4.38-4.86 (br. m, 3H, CH₂, CHN), 7.26-7.86 (a series of m, 8 H, fulvene), $t_R$ = 6.90 min, (M⁺ + 1) = 493.31. |

Synthesis of (4-Fmoc-5-substituted-6-oxo-piperazin-2-yl)-acetate (37): Compounds (36) were deprotected with 90% trifluoroacetic acid solution in dichloromethane for 3 hours, and then concentrated to dryness. Final products (37) were purified by silica gel column chromatography.

| R | Analytical Data for Compounds (37) |
|---|---|
| [benzyl structure] | ¹H NMR δ (CDCl₃): 1.82-2.13 (br. t, 1H, CHN), 2.32-2.53 (br. d, 1H, CH₂CO). 2.63-2.81 (br. d, 1H, CH₂CO), 2.90-3.29 (two br. m, CH₂Ph), 3.38-3.59 (br. m, 1H, CH₂N), 3.66-3.85 (br. m, 1H, CH₂N), 3.95-4.24 (two overlapping br. peaks, 2H, CHN, CH), 4.30-4.93 (br. d, 2H, CH₂O), 6.84-7.82 (a series of m, 13H, fulvene, and Ph), 8.08-8.25 (br. d, 1H, CO₂H), yield = quant., $t_R$ = 5.57 min, (M⁺ + 1)=471.07. |
| [structure] | ¹H NMR δ (CDCl₃): 0.72-1.92 (five br. m, 9H, CH₂, and CH₃), 2.14-2.70 (two br m, 3H, CH₂CO, and CHN), 3.26-3.62 (two br. m, 1H, CH₂N), 3.70-3.90 (br. m, 1H, CH₂N), 4.03-4.30 (two m, 2H, CHN, and CH), 4.42-4.82 (br. m, 2H, CH₂O), 7.28-7.82 (a series of m, 8H, fulvene), 7.97 (s, 1H, CO₂H), yield = 90%, $t_R$ =5.61 min, (M⁺ + 1) = 437.76. |
| [structure with H] | ¹H NMR δ (CDCl₃): 2.10-2.66 (m, 2H, CH₂CO), 3.2-3.92 (four m, 3H, CH₂N, CHN), 3.97-4.06 (m, 1H, CH), 4.2-4.3 (m, 2H, CH₂), 4.48-4.62 (m, 2H, CH₂N), 7.24-7.81 (a series of m, 8H, fulvene), $t_R$ = 4.74 min, (M⁺ + 1) = 381.13. |
| [structure with CH₃] | ¹H NMR δ (CDCl³): 1.15-1.37 (br. m, 3H, CH₃), 2.22-2.78 (three br. m, 2H, CH₂CO), 3.0-4.10 (five br. m, 3H, CH₂N, CHN), 4.15-4.40 (m, 1H, CH), 4.45-4.7 (br. m, 3H, CH₂, CHN), 7.26-8.10 (a series of m, 8H, fulvene), $t_R$ = 4.66 min, (M⁺ + 1) = 395.32. |
| [structure] | ¹H NMR δ (CDCl₃): 0.6-1.2 (m, 6H, CH₃), 1.22-2.8 (four m, 4H, CH₂CO, CH₂), 3.1-4.0 (five m, 3H, CH₂N, CHN), 4.18-4.32 (m, 1H, CH), 4.41-4.84 (m, 3H, CH₂, CHN), 7.26-8.2 (a series of m, 8H, fulvene), $t_R$ = 5.46 min, (M⁺ + 1) = 437.37. |

Method J: Diphenylmethyl 3-Fmoc-amino-4-(methoxycarbonyl-substituted-methylamino)-butyrates (41) were prepared by reductive amination of diphenylmethyl 3-Fmoc-amino-4-oxo-butyrate (40) with α-amino esters (2), using either sodium cyanoborohydride or sodium triacetoxyborohydride as the reducing agent. The diphenylmethyl 3-Fmoc-amino-4-oxo-butyrate (40) required for the reductive amination was prepared by lithium aluminum hydride reduction of the Weinreb amide derivative (39), which was formed from commercially available Fmoc-aspartic acid α-allyl ester derivative (38) by protection of the β-ester under Mitsunobu conditions. The allyl ester was removed using palladium (0) catalyst, followed by Weinreb amide formation using TBTU as the coupling agent. Diphenylmethyl 3-Fmoc-amino-4-(methoxycarbonyl-substituted-methylamino)-butyrate (41) was then Fmoc deprotected, cyclized, diphenylmethyl ester removed by hydrogenation, followed by Fmoc protection to give the final product (4-Fmoc-5-substituted-6-oxo-piperazin-2-yl)-acetic acid (37).

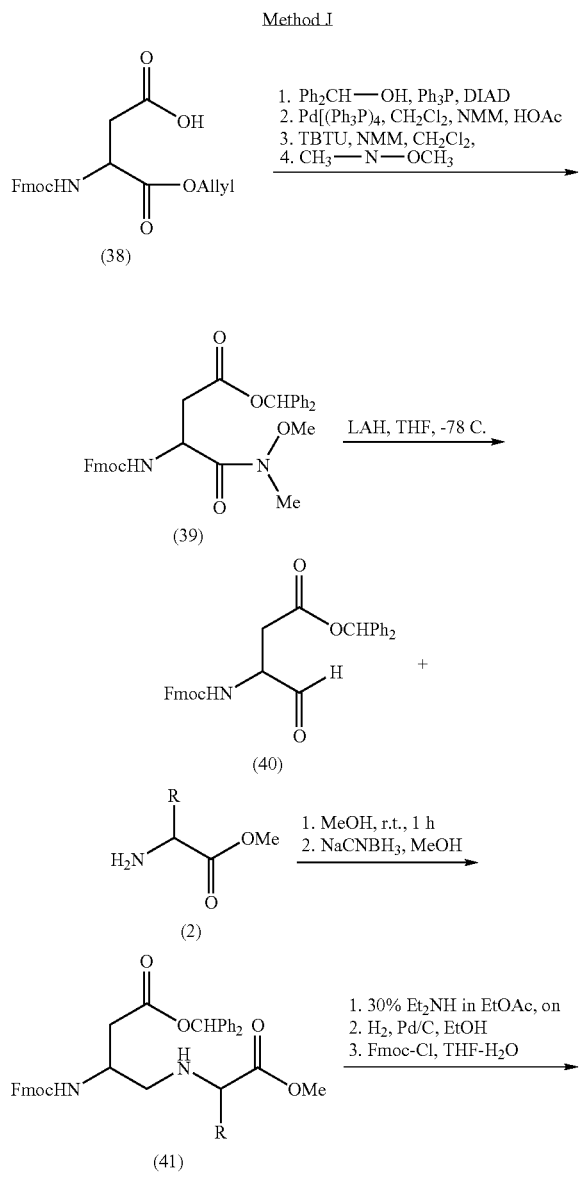

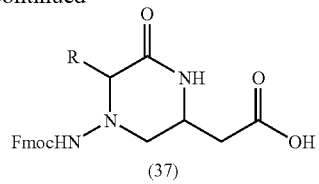

Synthesis of Fmoc-Asp-(OCHPh$_2$) Weinreb amide (39): To a solution of 5.1 g (13.0 mmol) of Fmoc-aspartic acid α-allyl ester (38) in 30 mL of dry tetrahydrofuran, containing 3.4 g (13 mmol) of triphenylphosphine, and 2.41 g (13.1 mmol) of diphenylmethanol, kept at 0° C. under nitrogen, was added slowly 2.6 mL (13.4 mmol) of diisopropyl azodicarboxylate. The ice bath was removed, and the reaction stirred at room temperature overnight, concentrated to dryness, and then purified by silica gel column chromatography. $^1$H NMR δ (CDCl$_3$) 2.96-3.06 (dd, 1H, CH$_2$CO), 3.15-3.26 (dd, 1H, CH$_2$CO), 4.18-4.76 (a series of m, 3H, CH, CH$_2$), 5.14-5.32 (m, 1H, CHN), 5.76-5.86 (m, 1H, CHO), 7.20-7.80 (a series of m, 18H, fulvene, and Ph); HPLC t$_R$=7.68 min, (M$^+$+Na$^+$)= 583.90.

The product (9.8 mmol) was then dissolved in 40 mL of a dichloromethane:acetic acid:N-methyl morpholine solution at 37:2:1, containing 1.5 g (1.3 mmol) of tetrakis triphenylphosphine palladium (0), and the solution stirred at room temperature overnight, concentrated to dryness, and partitioned between 100 mL of ethyl acetate and 30 mL of water. The layers were separated, and the organic layer washed with 1×50 mL of water, dried over sodium sulfate, and concentrated. The residue was suspended in 20 mL of dry dichloromethane, and 1.65 mL (15 mmol) of N-methyl morpholine, and 4.07 g (12.7 mmol) of TBTU were added, and the suspension stirred at room temperature for 20 minutes, followed by the addition of 1.65 mL (15 mmol) of N-methyl morpholine, and 1.52 g (15.6 mmol) of N,O-dimethyl hydroxylamine hydrochloride salt. The suspension was stirred at room temperature for 2 hours, concentrated, partitioned between 100 mL of ethyl acetate and 50 mL of water. The organic layer was washed with 1×30 mL of water, 1×30 mL of saturated sodium bicarbonate solution, and 1×30 mL of 1N hydrochloric acid solution, dried over sodium sulfate, and concentrated. The product was purified by silica gel column chromatography. $^1$H NMR δ (CDCl$_3$) 2.76-2.88 (dd, 1H, CH$_2$CO), 2.89-3.00 (dd, 1H, CH$_2$CO), 3.16 (s, 3H, CH$_3$N), 3.70 (s, 3H, CH$_3$O), 4.14-4.22 (dd, 1H, CH), 4.28-4.40 (t, 2H, CH$_2$), 5.07-5.16 (dd, 1H, CHN), 5.69-5.76 (d, 1H, CHO), 7.24-7.8 (a series of m, 18H, fulvene, and Ph); HPLC t$_R$=7.08, (M$^+$+Na$^+$)=587.03.

Synthesis of Diphenylmethyl 3-Fmoc-amino-4-oxo-butyrate (40): Compound (40) is prepared using a procedure similar to the one described for compound (9).

Synthesis of Diphenylmethyl 3-Fmoc-amino-4-(methoxycarbonyl-substituted-methylamino)-butyrate (41): Compounds (41) were prepared using a procedure similar to the one described for compound (10), but using compound (40) as the aldehyde.

| R | Analytical Data for Compounds (41) |
|---|---|
| ![structure with HN, =NH, NHPbf] | $^1$H NMR δ (CDCl$_3$) 1.2-1.7 (m, 4H, CH$_2$), 1.42 (s, 3H, CH$_3$Ph), 1.60 (s, 6H, CH$_3$—Ph), 2.07 (s, 2H, CH$_2$), 2.52 (s, 3H, CH$_3$—Ph), 2.58 (s, 3H, CH$_3$—Ph), 2.08-2.80 (a series of m, 2H, CH$_2$CO), 3.0-3.2 (m, 2H, CH$_2$N), 3.64 (s, 3H, CH$_3$O), 3.96-4.10 (m, 1H, CHN), 4.20-4.28 (m, 1H, CH), 4.28-4.40 (br. m, 2H, CH$_2$), 5.82-6.18 (m, 1H, CHO), 7.24-7.80 (a series of m, 18H, fulvene, and Ph), HPLC t$_R$ = 6.53, (M$^+$ + 1) = 930.56. |

Synthesis of (4-Fmoc-5-substituted-6-oxo-piperazin-2-yl)-acetic acid (37): A solution of 10 mmol of compound (41) in 30 mL of 30% diethylamine in ethyl acetate was stirred at room temperature for 3 hours. The solution was then concentrated to dryness, redissolved in 2×30 mL of ethyl acetate, and reconcentrated. The residue dissolved in 50 mL of ethanol, and 20 mL of 1N hydrochloric acid solution, and hydrogenated at room temperature and atmospheric pressure overnight, filtered through celite, and concentrated to dryness. The residue was dissolved in 20 mL of tetrahydrofuran, and 10 mL of water, and 2.52 g (30 mmol) of solid sodium bicarbonate was added, followed by the addition of 3.3 g (13 mmol) of Fmoc-Cl. The mixture was stirred for 3 hours, diluted with 100 mL of ethyl acetate, the layers separated, and the organic layer washed with 2×50 mL of water, dried over magnesium sulfate, and concentrated. The product was purified by silica gel column chromatography.

| R | Analytical Data for Compounds (37) |
|---|---|
| ![structure with HN, =NH, NHPbf] | $^1$H NMR δ (CDCl$_3$) 1.2-1.6 (m, and s, 7H, CH$_2$, CH$_3$Ph), 2.10 (s, 2H, CH$_2$), 2.46 (s, 3H, CH$_3$—Ph), 2.56 (s, 3H, CH$_3$—Ph), 2.46-2.63 (br. m, 2H, CH$_2$CO), 3.0-3.95 (3 br. m, 5H, CH$_2$N, CHN), 4.10-4.30 (br. m, 1H, CH), 4.40-4.80 (br. m, 3H, CHN, CH$_2$), 7.22-7.80 (a series of m, 8H, fulvene), HPLC t$_R$ = 5.73, (M$^+$ + 1) 732.24. |

Method K: The syntheses of (5-substituted-6-oxo-piperazin-2-yl)-acetic acid scaffolds are done starting from commercially available Fmoc-Aspartic acid α tert-butyl ester (42). Fmoc-aspartic acid α tert-butyl ester is reduced to Fmoc-Homoserine α tert-butyl ester with sodium borohydride via the mixed anhydride, followed by protection of the alcohol with benzyl bromide to give Fmoc-Homoserine benzyl ether α tert-butyl ester (43). The tert-butyl ester is then removed with trifluoroacetic acid, and the acid is reduced to the alcohol with sodium borohydride via the mixed anhydride to give 2-Fmoc-amino-4-benzyloxy-1-butanol (44). Alcohol (44) is then converted to 2-Fmoc-amino-4-benzyloxybutanal (45) using Dess-Martin periodinane as described previously. Reductive amination of 2-Fmoc-amino-4-benzyloxybutanal (45) and α-amino ester (2) gives the (2-Fmoc-amino-4-benzyloxy-butylamino)-2-substituted acetic acid methyl ester (46). Fmoc deprotection with diethyl amine gives the free primary amine which cyclizes to 6-benzyloxyethyl-3-substituted-piperazin-2-one spontaneously. The benzyl ether is removed by hydrogenation, and the secondary amine is protected as its Fmoc derivative to give 4-Fmoc-6-hydroxymethyl-3-substituted-piperazin-2-ones (47). Finally, the primary alcohol is oxidized to the acid to give the final products (48) as described in method A.

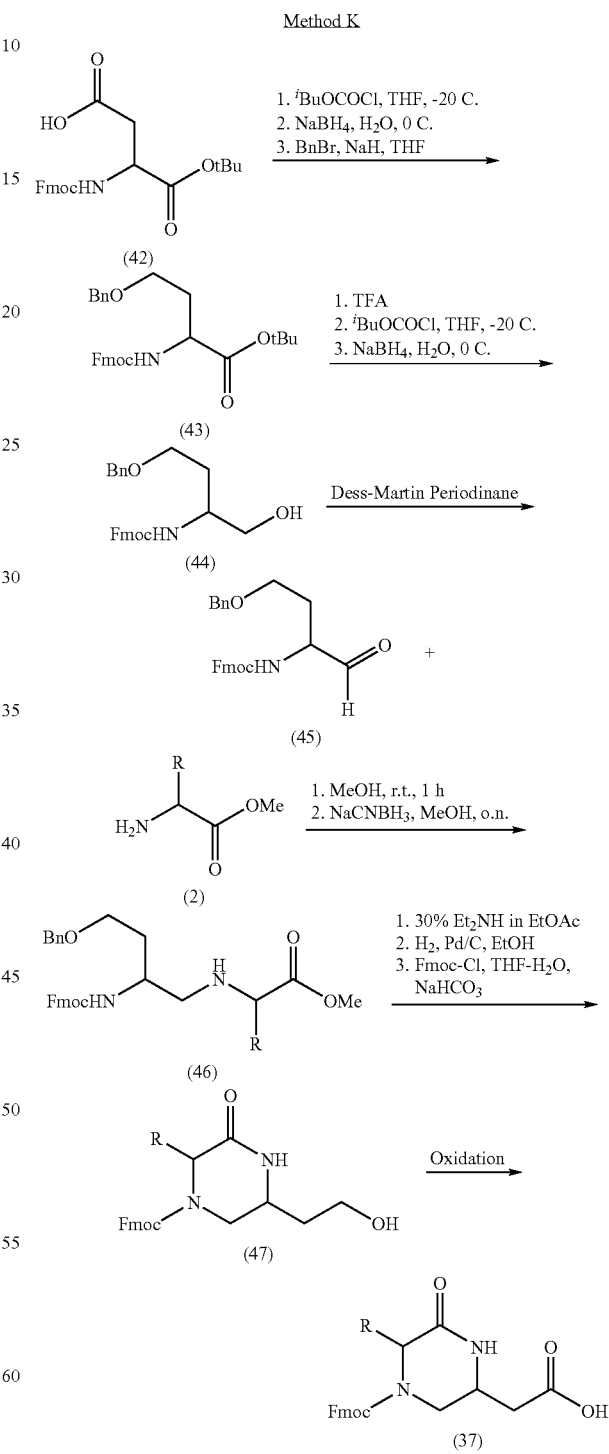

Synthesis of Fmoc-Homoserine (OBn) α tert-butyl ester (43): To a solution of 10.0 mmol of Fmoc Asp-O$^t$Bu (42) in 50 mL of dry tetrahydrofuran, kept at −20° C. under nitrogen, is added 1.77 mL (12.7 mmol) of triethyl amine, followed by the slow addition of 1.57 mL (12.0 mmol) of isobutylchloroformate. The mixture is stirred for 30 minutes, and then poured slowly over an ice-cold solution of 3.77 g (99.6 m mol) of sodium borohydride in 10 mL of water, keeping the temperature below 5° C. The reaction is stirred at 0° C. for 15 minutes, and then quenched with 1N hydrochloric acid solution. The reaction mixture is diluted with 100 mL of ethyl acetate, and the layers separated. The organic layer was washed with 2×25 mL of 1N hydrochloric acid solution, 2×25 mL of water, dried over magnesium sulfate and concentrated, and purified by silica gel column chromatography. Purified compound is then dissolved in 30 mL of tetrahydrofuran, and 12 mmol of 60% sodium hydride dispersion in mineral oil is added, followed by 0.2 mmol of tetrabutylammonium iodide and 12 mmol of benzyl bromide, and the mixture is stirred overnight, quenched with 50 mL of saturated aqueous sodium bicarbonate, and extracted with 100 mL of ethyl acetate. The compound is then purified by silica gel column chromatography.

Synthesis of 2-Fmoc-amino-4-benzyloxy-1-butanol (44): Deprotection of the tert-butyl ester using 90% trifluoroacetic acid is done as described for compound (37) in method I, followed by reduction of the acid to the alcohol with sodium borohydride via the mixed anhydride intermediate as described for compound (13).

Synthesis of 2-Fmoc-amino-4-benzyloxy-butanal (45): 2-Fmoc-amino-4-benzyloxy-1-butanol (44) is oxidized to the aldehyde using Dess-Martin periodinane as described for the synthesis of (9).

Synthesis of (2-Fmoc-amino-4-benzyloxy-butylamino)-2-substituted acetic acid methyl ester (46): reductive amination of 2-Fmoc-amino-4-benzyloxy-butanal (45) with an α-amino ester (2) using either sodium cyanoborohydride or sodium triacetoxyborohydride as the reducing agent is done as described for the synthesis of (10).

Synthesis of 4-Fmoc-6-hydroxymethyl-3-substituted-piperazin-2-ones (47): Fmoc deprotection of (2-Fmoc-amino-4-benzyloxy-butylamino)-2-substituted acetic acid methyl ester (46) with concomitant cyclization, followed by de-benzylation and Fmoc reprotection is done as described for compound (37) in method J.

Synthesis of 4-Fmoc-5-substituted-6-oxo-piperazin-2-yl-acetic acid (37): Oxidation of 4-Fmoc-6-hydroxymethyl-3-substituted-piperazin-2-ones (47) to the acid is done as described in method A. The choice of the oxidizing agent used is based on the nature of the group in the 5-position.

Synthesis of 2-Substituted 3-Oxo-[1,4]-diazepane-5-carboxylic acid Scaffolds (Methods L, M, N)

The synthesis of 2-substituted 3-oxo-[1,4]-diazepane-5-carboxylic acid scaffolds is done using several methods.

Method L: tert-butyl 2-Cbz-amino-4-(benzyloxycarbonyl-substituted-methyl-Boc amino)-butyrates (52) are prepared by reductive amination of tert-butyl Cbz-2-amino-4-oxo-butyrate (50) with amino ester (51), using either sodium cyanoborohydride or sodium triacetoxyborohydride as the reducing agent, followed by Boc protection of the secondary amine. The tert-butyl Cbz-2-amino-4-oxo-butyrate (50) required for the reductive amination is prepared by lithium aluminum hydride reduction of the Weinreb amide derivative (49). The diazepane ring is formed by protecting group removal, followed by cyclization with a peptide forming reagent to give (53). Finally, 4-Fmoc-2-substituted-3-oxo-[1,4]-diazepane-5-carboxylic acids (54) are formed by protecting group exchange.

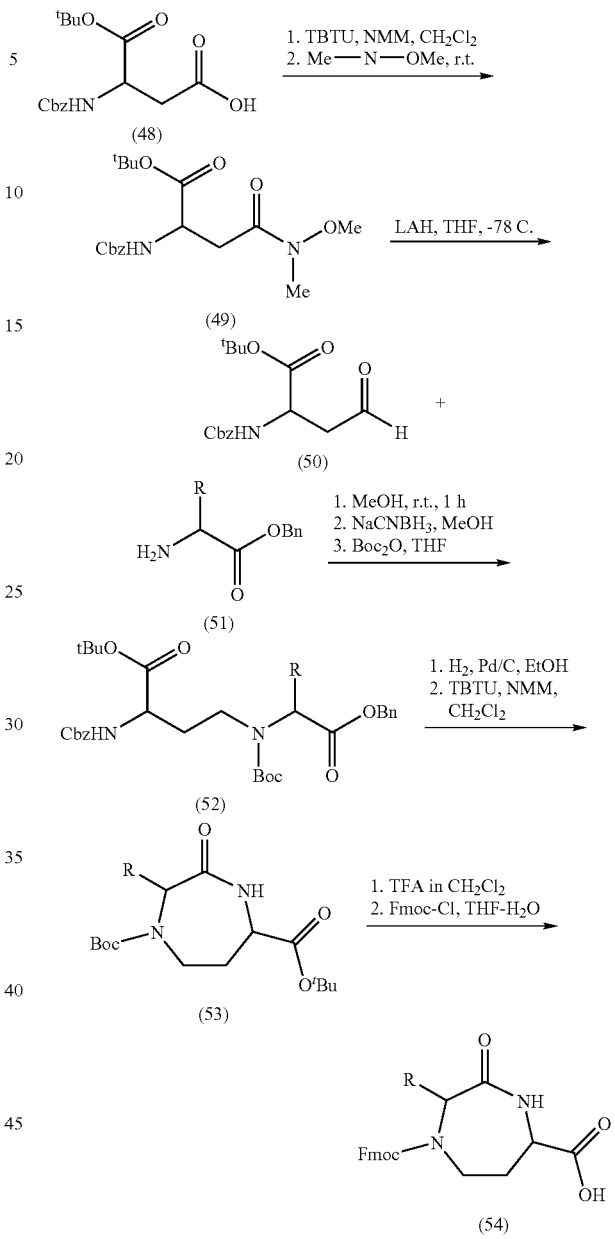

Synthesis of Cbz-Asp-(Weinreb amide)-O$^t$Bu (49): Compound (49) is prepared using a procedure similar to the one described for compound (14).

Synthesis of tert-butyl 3-Cbz-amino-4-oxo-butyrate (50): Compound (50) is prepared using a procedure similar to the one described for compound (9).

Synthesis of tert-butyl 2-Cbz-amino-4-(benzyloxycarbonyl-substituted-methylamino)-butyrate (52): The reductive amination is done with procedure similar to the one described for compound (10). The secondary amine is protected by reaction of the crude mixture with 2 equivalents of Boc dicarbonate in tetrahydrofuran.

Synthesis of tert-butyl 1-Boc 2-substituted-3-oxo-[1,4]-diazepane-5-carboxylate (53): A solution of 10 mmol of compound (52) in 30 mL of ethanol is hydrogenated at room temperature and atmospheric pressure for 2 hours, filter through celite, and concentrated to dryness. The residue is dissolved in 100 mL of dichloromethane and 1.2 equivalents of TBTU, and 2.6 equivalents of N-methyl-morpholine are added. The solution is stirred at room temperature overnight, and then concentrated. The residue is partitioned between 50 mL of ethyl acetate and 25 mL of 1N hydrochloric acid solution, washed with 1×20 mL of a saturated sodium bicarbonate solution, dried over magnesium sulfate, and concentrated.

Synthesis of 1-Fmoc 2-substituted-3-oxo-[1,4]-diazepane-5-carboxylic acid (54): A solution of 10 mmol of compound (53) in 10 mL of 90% trifluoroacetic acid in dichloromethane is stirred at room temperature for 2 hours, and then the solution is concentrated to dryness. The residue is dissolved in 20 mL of tetrahydrofuran and 10 mL of water, and 2.52 g (30 mmol) of solid sodium bicarbonate is added, followed by the addition of 3.36 g (13 mmol) of Fmoc-Cl. The mixture is stirred for 3 hours, and then diluted with ethyl acetate. The layers are separated, and the organic layer washed with 2×50 mL of water, dried over magnesium sulfate, and concentrated.

Method M: the reduced dipeptide analogs (60) are prepared by reductive amination of diphenylmethyl Alloc-2-amino-4-oxo-butyrate (59) with amino ester (29), using either sodium cyanoborohydride or sodium triacetoxyborohydride as the reducing agent, followed by Cbz protection of the secondary amine. Diphenylmethyl Alloc-2-amino-4-oxo-butyrate (59) required for the reductive amination is prepared by lithium aluminum hydride reduction of the Weinreb amide derivative (58), which is prepared by protecting group exchange of Weinreb amide derivative (57). The diazepane ring is then formed by allyl and alloc group removal, followed by ring closure in the presence of a peptide forming reagent. 2-substituted 3-oxo-[1,4]-diazepane-5-carboxylic acid scaffolds (54) are formed by protecting group exchange.

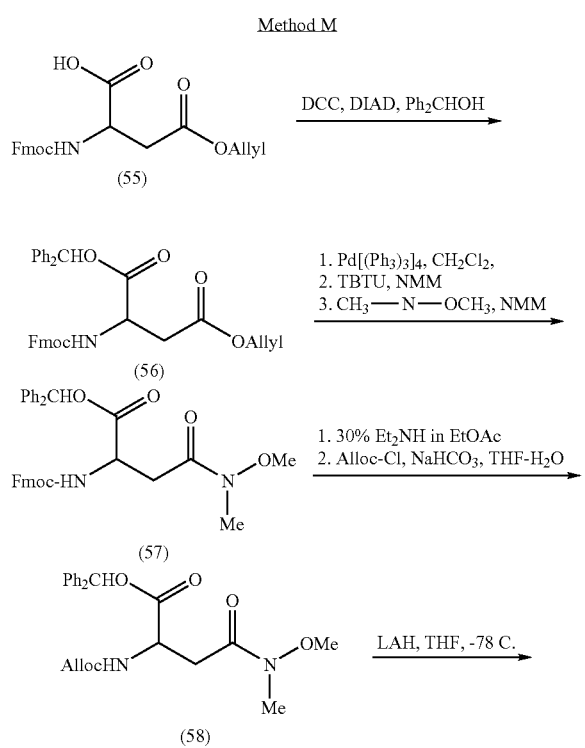

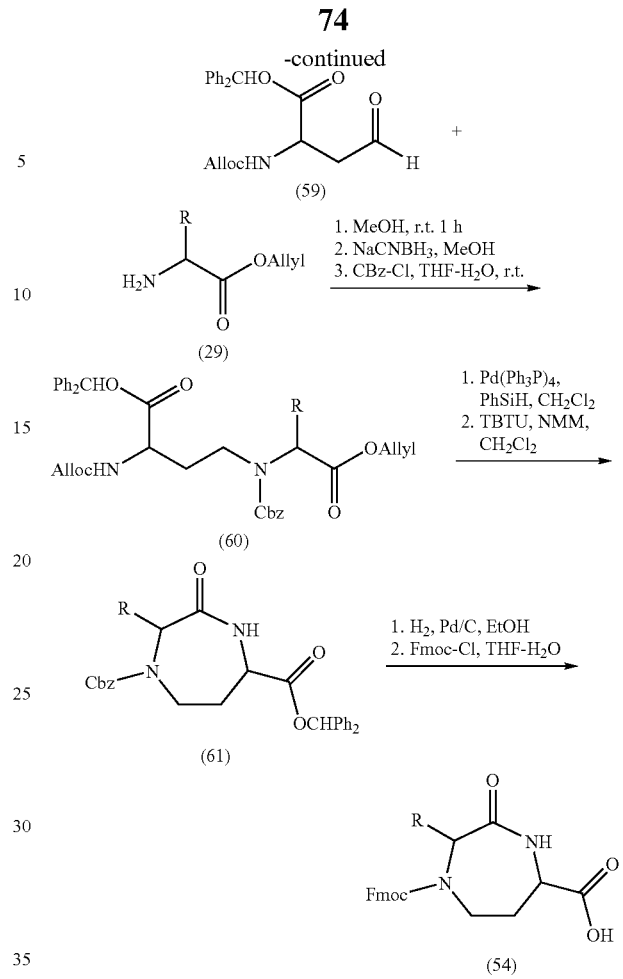

Synthesis of Fmoc-Asp-(Weinreb amide)-OCHPh$_2$ (57): Compound (57) is prepared using a procedure similar to the one described for compound (39).

Synthesis of Alloc-Asp-(Weinreb amide)-OCHPh$_2$ (58): A solution of 10 mmol of compound (56) in 20 mL of 30% diethylamine in ethyl acetate is stirred for 2 hours, and concentrated to dryness. The residue is dissolved in 20 mL of tetrahydrofuran and 10 mL of water, and 2.52 g (30 mmol) of solid sodium bicarbonate is added, followed by the addition of 13 mmol of Alloc-Cl. The mixture is stirred for 3 hours, and then diluted with ethyl acetate. The layers are separated, and the organic layer washed with water, dried over magnesium sulfate, and concentrated. Compound (58) is purified by silica gel column chromatography.

Synthesis of diphenylmethyl 3-Alloc-amino-4-oxo-butyrate (59): Compound (59) is prepared using a procedure similar to the one described for compound (9).

Synthesis of diphenyl methyl 2-Alloc-amino-4-(allyloxycarbonyl-substituted-methylamino)-butyrate (60): compound 60 is prepared by reductive amination using a procedure similar to the one described for compounds (15), but using compound (59) as the aldehyde. The product is purified by silica gel column chromatography.

Synthesis of diphenylmethyl 1-Cbz 2-substituted-3-oxo-[1,4]-diazepane-5-carboxylate (61): To a solution of 10 mmol of compound (60) in 30 mL of dichloromethane, kept at room temperature under nitrogen, is added 2 equivalents of phenylsilane and 0.3 equivalents of tetrakistriphenylphosphine palladium (0), and the solution stirred for 2 hours, and then 1.2 equivalents of TBTU and 1.3 equivalents of N-methyl-morpholine are added. The solution is stirred at room temperature overnight and concentrated. The residue is partitioned between 50 mL of ethyl acetate and 25 mL of 1N hydrochloric acid solution, washed with 1×20 mL of a saturated sodium bicarbonate solution, dried over magnesium sulfate, and concentrated.

Synthesis of 1-Fmoc 2-substituted-3-oxo-[1,4]-diazepane-5-carboxylic acid (54): A solution of 10 mmol of compound (61) in 30 mL of ethanol is hydrogenated at room temperature for 2 hours, filtered through celite, and then the solution is concentrated to dryness. The residue is dissolved in 20 mL of tetrahydrofuran, and 10 mL of water, and 2.52 g (30 mmol) of solid sodium bicarbonate is added, followed by the addition of 3.36 g (13 mmol) of Fmoc-Cl. The mixture is stirred for 3 hours, and then diluted with ethyl acetate. The layers are separated, and the organic layer washed with water, dried over magnesium sulfate, and concentrated.

Method N: Fmoc-Aspartic acid β tert-butyl ester is reduced to Fmoc-Aspartanol β tert-butyl ester (63) with sodium borohydride via the mixed anhydride, followed by protection of the alcohol with allyl bromide to give Fmoc-Aspartanol allyl ether β tert-butyl ester (64). The tert-butyl ester is then removed with trifluoroacetic acid, and the acid reduced to the alcohol with sodium borohydride via the mixed anhydride to give 3-Fmoc-amino-4-allyloxy-1-butanol (65). Alcohol (65) is then converted to 3-Fmoc-amino-4-allyloxybutanal (66) using Dess-Martin periodinane as described previously. Reductive amination of 3-Fmoc-amino-4-allyloxybutanal (66) and α amino ester (51), followed by alloc protection on the secondary amine, gives the (3-Fmoc-amino-4-allyloxy-butyl-alloc-amino)-2-substituted acetic acid benzyl esters (67). Alloc 7-allyloxymethyl-3-substituted-[1,4]-diazepan-2-ones (68) are formed by saponification of the benzyl ester, followed by Fmoc deprotection with diethyl amine to give the free primary amine which is cyclized using a peptide forming reagent such as TBTU. The final products (54) are formed by protecting group exchange: the allyl ether and the alloc are removed by palladium (0), and the secondary amine is protected as its Fmoc derivative to give 4-Fmoc-7-benzyloxymethyl-3-substituted-[1,4]-diazepan-2-ones, followed by primary alcohol oxidation to the acid to give the final products (54). The choice of the oxidizing agent used is based on the nature of the group in the 2-position.

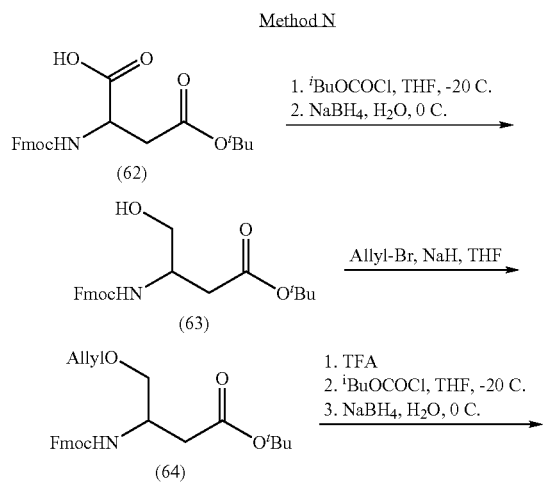

Method N

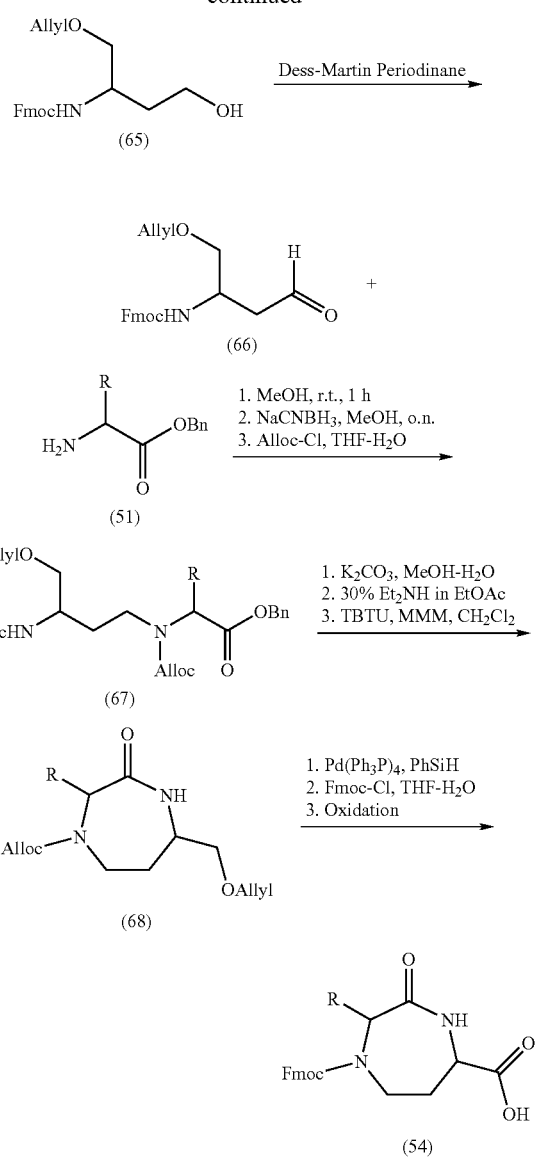

Synthesis of Fmoc-Aspartanol β tert-butyl ester (63): Compound (63) is prepared as described for the synthesis of compound (13), using Fmoc-Aspartic acid β tert-butyl ester (62) as the starting material.

Synthesis of 3-Fmoc-amino-4-allyloxy-butyric acid tert-butyl ester (64): To a solution of 10 mmol of (63) in 30 mL of tetrahydrofuran, kept at room temperature under nitrogen, is added 12 mmol of 60% sodium hydride dispersion in mineral oil, 2 mmol of tetrabutylammonium iodide, and 13 mmol allyl bromide, and the mixture is stirred overnight, quenched with 10 mL of saturated aqueous sodium bicarbonate, and extracted with 50 mL of ethyl acetate.

Synthesis of 3-Fmoc-amino-4-allyloxy-1-butanol (65): Compound (65) is prepared as described for the synthesis of compound (44).

Synthesis of 3-Fmoc-amino-4-allyloxy-butanal (66): 3-Fmoc-amino-4-allyloxy-1-butanol (65) is oxidized to the aldehyde using Dess-Martin periodinane as described for the synthesis of (9).

Synthesis of (3-Fmoc-amino-4-allyloxy-butyl-alloc-amino)-2-substituted acetic acid methyl ester (67): reductive amination of 3-Fmoc-amino-4-benzyloxy-butanal (66) with an α-amino ester (51) using either sodium cyanoborohydride or sodium triacetoxyborohydride as the reducing agent as described for compound (10), followed by protection of the secondary amine as the alloc derivative, is done as described for compound (15), but using allyl chloroformate instead of benzyl chloroformate.

Synthesis of 4-Alloc-7-allyloxymethyl-3-substituted-[1,4]-diazepan-2-ones (68): A solution of 10 mmol of (3-Fmoc-amino-4-allyloxy-butyl-alloc-amino)-2-substituted acetic acid methyl ester (67), 20 mmol of potassium carbonate in 20 mL of methanol, and 10 mL of water is stirred at room temperature for 3 hours, neutralized with 21 mL of a 1N hydrochloric acid solution, and then concentrated to dryness. The residue is dissolved in 20 mL of 30% diethyl amine in ethyl acetate and stirred at 3 hours, and then concentrated to dryness. The residue is dissolved in 100 mL of dichloromethane, and 12 mmol of TBTU and 24 mmol of N-methylmorpholine are added, and the solution stirred at room temperature overnight, and then concentrated to dryness. The residue is partitioned between 30 mL of ethyl acetate and 30 mL of 1N hydrochloric acid solution, and then the layers separated. The organic layer is washed with 30 mL of a saturated sodium bicarbonate solution, dried over magnesium sulfate, and purified by silica gel column chromatography.

Synthesis of 4-Fmoc-2-substituted-3-oxo-[1,4]-diazepane-5-carboxylic acid (54): To solution of 10 mmol of compound (68) in 30 mL of dichloromethane, kept at room temperature under nitrogen, is added 2 equivalents of phenylsilane and 0.3 equivalents of tetrakistriphenylphosphine palladium (0), and the solution then stirred for 2 hours, and concentrated to dryness. The secondary amine is dissolved in 20 mL of tetrahydrofuran, and 10 mL of water, followed by the addition of 2.52 g (30 mmol) of solid sodium bicarbonate, and 1.2 equivalents of Fmoc-Cl and the biphasic solution is stirred at room temperature for 2 hours, diluted with 30 mL of ethyl acetate, and the layers separated. Oxidation of 4-Fmoc-7-hydroxymethyl-3-substituted-[1,4]-diazepan-2-ones to the final product (54) is done as described in method A. The choice of the oxidizing agent used is based on the nature of the group in the 2-position, as in Method A for the conversion of (6) to (7).

Synthesis of 6-substituted-5-oxo-piperazine-2-carboxylic acid Scaffolds (Method O)

The syntheses of 6-substituted-5-oxo-piperazine-2-carboxylic acid scaffolds containing non-functionalized side chains in the 6-position are done as outlined in Method O, starting from commercially available 3-Fmoc-amino-1,2-propan-diol 1-chloro-trityl resin (69) which is oxidized to the ketone (70) using Dess-Martin periodinane. Reductive amination of ketone (70) with an α amino ester (2) gives resin bound (1-aminomethyl-2-chloro-trityloxy-ethylamino)-2-substituted acetic acid methyl ester (71), which is cyclized to 5-chlorotrityloxymethyl-3-substituted-piperazin-2-one (72) after deprotection of the amine. Reprotection of the secondary amine, followed by cleavage from the resin, gives Fmoc-5-hydroxymethyl-3-substituted-piperazin-2-one (73) which is oxidized to 6-substituted-5-oxo-piperazine-2-carboxylic acid (74) using either of the procedures described in method A.

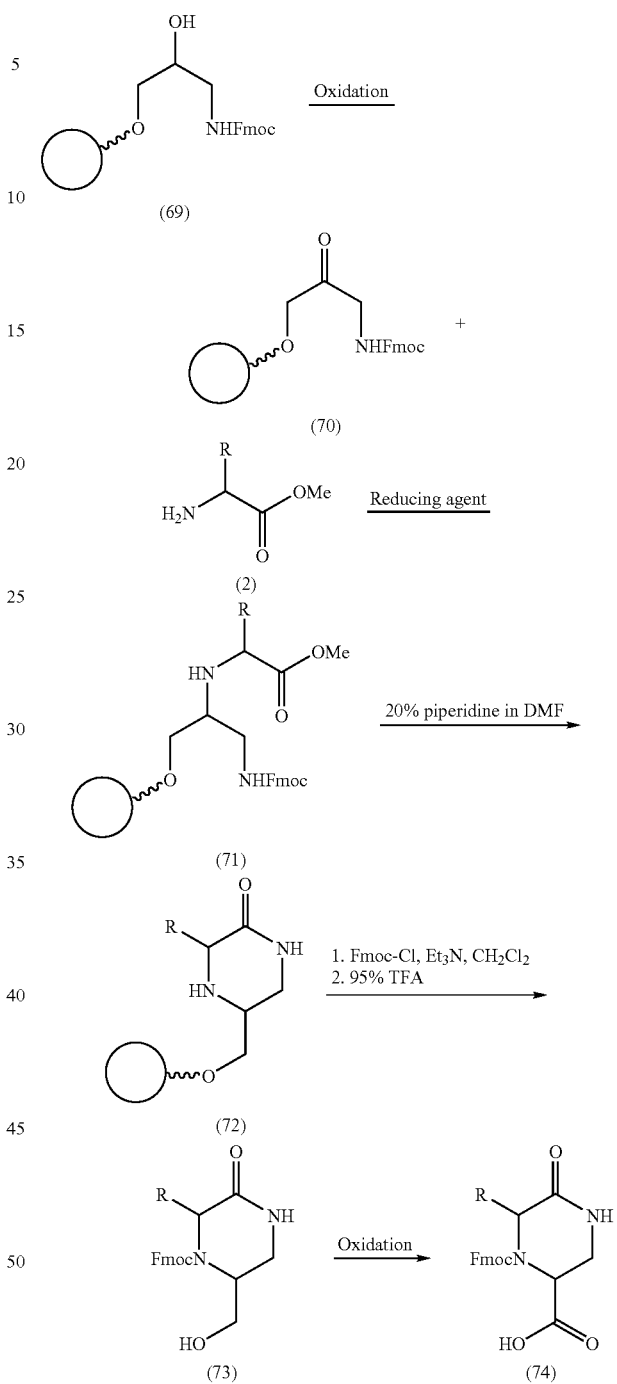

Synthesis of 1-amino-3-chlortrityloxy-propan-2-one (70): the oxidation of resin bound alcohol (69) is done by sulfur trioxide oxidation, NMO/TPAP (N-methylmorpholine-N-oxide/tetrapropyl ammonium perrthenate) oxidation, or PDC oxidation. For sulfur trioxide oxidation, a procedure similar to the one described in Parikh, J. R. and Doering, W. V., *J. Am. Chem. Soc.* 89:5505-5 507 (1967) is used. For NMO/TPAP oxidation, to 0.3 mmol of resin-bound alcohol is added a solution of 3 mmol of N-methylmorpholine N-oxide in 10 mL of dry dimethylformamide, and then 0.06 mmol of tetrapropylammonium perruthenate (TPAP) is added to the resin suspension. The reaction is shaken for 80 minutes. The solvent is drained, the resin washed with tetrahydrofuran and dichloromethane, and then dried under vacuum. For PDC oxidation, a suspension of resin bound alcohol in 0.2 M pyridinium dichromate in dimethylformamide is shaken at 37° C. for 4 hours, the solvent is drained, and the resin washed with dimethylformamide, tetrahydrofuran, and dichloromethane.

Synthesis of (1-aminomethyl-2-chloro-trityloxy-ethylamino)-2-substituted acetic acid methyl ester (71): the reductive amination of resin bound ketone (70) with amino ester is done by one of two different methods. In one method, a solution of 2.6 mmol of α amino ester (2) in 20 mL of 1% acetic acid in dimethylformamide is added 2.6 mmol of sodium triacetoxyborohydride, followed by the immediate addition of 0.5 mmol of ketone-derivatized resin (70), and the mixture is shaken for 60 minutes, rinsed with methanol, 10% di-isopropyl ethyl amine, dimethylformamide, and methanol. In a second method, a suspension of 0.05 mmol of ketone-derivatized resin (70) and 2.0 M α amino ester hydrochloride (2) in methanol, containing 0.05 M sodium cyanoborohydride is shaken at room temperature for 5 hours, drained, and washed.

Synthesis of 5-chlorotrityloxymethyl-3-substituted-piperazin-2-one (72): A suspension of 0.05 mmol of resin in 10 mL of 20% piperidine in dimethylformamide is shaken at room temperature for 2 hours.

Synthesis of Fmoc-5-hydroxymethyl-3-substituted-piperazin-2-one (73): A suspension of 0.05 mmol of (72) in 10 mL of dichloromethane, containing 0.25 mmol of Fmoc-Cl and 0.25 mmol of triethyl amine is stirred at room temperature for 6 hours, drained, and washed with dichloromethane. The resin is resuspended in 10 mL of 95% trifluoroacetic acid in dichloromethane, and the suspension shaken for 2 hours, and filtered, and the filtrate is concentrated.

Synthesis of Fmoc-6-substituted-5-oxo-piperazine-2-carboxylic acid (74): Oxidation of (73) to the desired product is done by any of the procedures described for method A.

Synthesis of α,α-Disubstituted Amino Acids
(Methods P and Q)

In certain of the peptidomimetics of the invention, it is possible and contemplated to employ a disubstituted amino acid residue, such as an α,α-disubstituted amino acid where the substituents are either the same or different. In one aspect, an α,α-disubstituted amino acid is employed in either the Aaa$^1$ or Aaa$^8$ position, wherein at least one of the side chains of the α,α-disubstituted amino acid is a side chain of Nle, Ala, Leu, Ile, Val, Nva, Met(O) or Met(O$_2$). The following synthetic Methods P and Q describe making α,α-di-n-butylglycine (2-Amino-2-butyl-hexanoic acid), wherein each of the side chains are —(CH$_2$)$_3$—CH$_3$, and thus each is the same as the side chain of Nle. However, it is to be understood that similar methods and schemes may be employed in the making of other α,α-disubstituted amino acids, where the substituents are either the same or different. Additionally, any method of making an α,α-disubstituted amino acid may be employed in the practice of this invention, and the practice of this invention is not limited to the methods of the following synthetic schemes. Thus any method known in the art for the synthesis of α,α-disubstituted amino acids may be employed in the practice of this invention. The following teach alternative methods for the making of α,α-disubstituted amino acids: Clark J. S, and Middleton M. D.: Synthesis of novel alpha-substituted and alpha,alpha-disubstituted amino acids by rearrangement of ammonium ylides generated from metal carbenoids. Org. Lett. 4(5):765-8 (2002); Guino M., Hii K. K.: Wang-aldehyde resin as a recyclable support for the synthesis of alpha,alpha-disubstituted amino acid derivatives. Org. Biomol. Chem. 3(17):3188-93 (2005); and Kotha S., Behera M.: Synthesis and modification of dibenzylglycine derivatives via the Suzuki-Miyaura cross-coupling reaction. J. Pept. Res. 64(2):72-85 (2004).

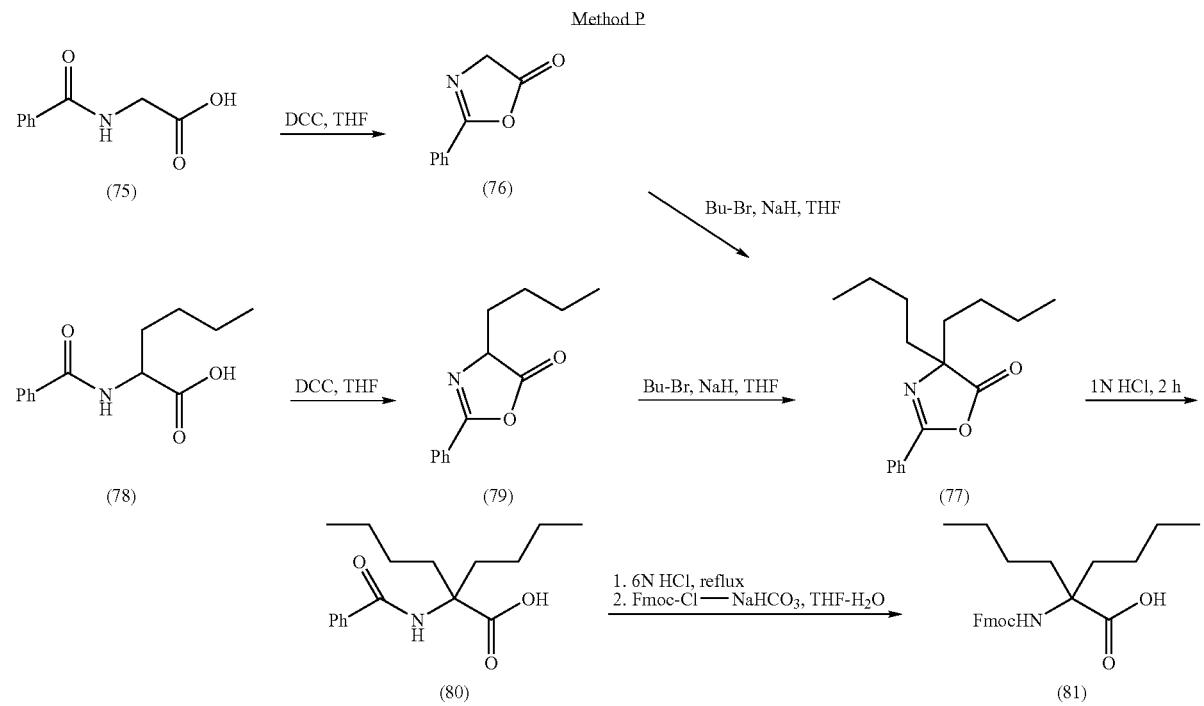

Synthesis of Benzoyl di-n-butylglycine (80): To a solution of 10 mmol benzoyl glycine (75) in 20 mL of dichloromethane, kept at 0° C. under nitrogen, is added slowly 12 mmol of N,N'-dicyclohexylcarbodiimide (DCC), and the reaction stirred for 2 hours to yield compound (76). The solid is filtered off, and the filtrate concentrated. The residue is dissolved in 15 mL of tetrahydrofuran, cooled to 0° C., and then 24 mmol of sodium hydride is added, followed by 30 mmol of n-butyl bromide. The suspension is stirred at 0° C. for 2 hours and then allowed to warm to room temperature, and the solution concentrated to dryness to yield compound (77). Alternatively, compound (77) can also be prepared from benzoyl norleucine (78) in a similar manner except that 12 mmol of sodium hydride and 15 mmol of n-butyl bromide are used. Compound (77) is dissolved in methanol, 50 mL of 1N hydrochloric acid solution is added, and the solution stirred for 2 hours, and concentrated. Compound (80) is purified by silica gel column chromatography.

Synthesis of Fmoc di-n-butylglycine (81): 10 mmol of compound (80) is dissolved in 30 mL of dioxane, and 10 mL of 6N hydrochloric acid solution is added, and the solution is refluxed overnight. The reaction is cooled to room temperature, concentrated to dryness, redissolved in 30 mL of tetrahydrofuran, and 10 mL of water and 30 mmol of sodium bicarbonate is added, followed by 15 mmol of Fmoc-Cl. The biphasic solution is stirred for 1 hour, and the tetrahydrofuran removed under vacuum. The aqueous solution is extracted with 1×50 mL of diethyl ether, acidified with 1N hydrochloric acid solution, and extracted with 2×50 mL of ethyl acetate. The ethyl acetate layers are combined, dry over sodium sulfate, and concentrated. Compound (81) is purified by silica gel column chromatography.

Similar methods may be employed by starting with any appropriate amino acid derivative (similar to compound 78), and by using an appropriate alkyl butyl, aryl butyl, or aralkyl butyl reagent the scheme will yield a variety of disubstituted (R, R') amino acid surrogates where R and R' are different.

Synthesis of Fmoc-α,α di-n-butyl glycine (87): To a suspension of 20 mmol of glycine methyl ester hydrochloride (82), and 2 g of powdered molecular sieves in 40 mL of dry tetrahydrofuran, kept at room temperature, is added 24 mmol of potassium hydroxide, followed by 22 mmol of benzaldehyde. The suspension is stirred for 2 hours, filtered, and the filtrate concentrated. The residue is redissolved in 40 mL of dry toluene, and then added to a suspension of 60 mmol of sodium hydride in toluene, followed by the addition of 60 mmol of n-butyl bromide. The suspension is stirred for 12 hours, followed by addition of 30 mL of a solution of 6N hydrochloric acid, stirred at room temperature for 2 hours, and then the layers separated. The hydrochloride salt of (84) thus obtained is used in situ for preparation of (87). To isolate (84) as the hydrochloride salt the aqueous layer is concentrated to dryness and the product crystallized from dry methanol-ether.

Alternatively, compound (84) can be prepared from norleucine methyl ester hydrochloride using a similar synthetic procedure except that 30 mmol of sodium hydride and 30 mmol of n-butyl bromide are used for conversion of (86) to (84).

The aqueous mixture of the hydrochloride form of compound (84) as obtained above is heated to reflux for 1 hour and then cooled to room temperature. It is neutralized with solid sodium hydroxide and then diluted with 30 mL of tetrahydrofuran. Sodium bicarbonate (30 mmol) is added followed by 15 mmol of Fmoc-Cl. The biphasic solution is stirred for 1 hour, and the tetrahydrofuran removed under vacuum. The aqueous solution is extracted with 1×50 mL of diethyl ether, acidified with 1N hydrochloric acid solution, and extracted with 2×50 mL of ethyl acetate. The ethyl acetate layers are combined, dried over sodium sulfate, and concentrated. Compound (87) is purified by silica gel column chromatography.

Similar methods may be employed by starting with any appropriate amino acid derivative (similar to compound 85), and by using an appropriate alkyl butyl, aryl butyl, or aralkyl

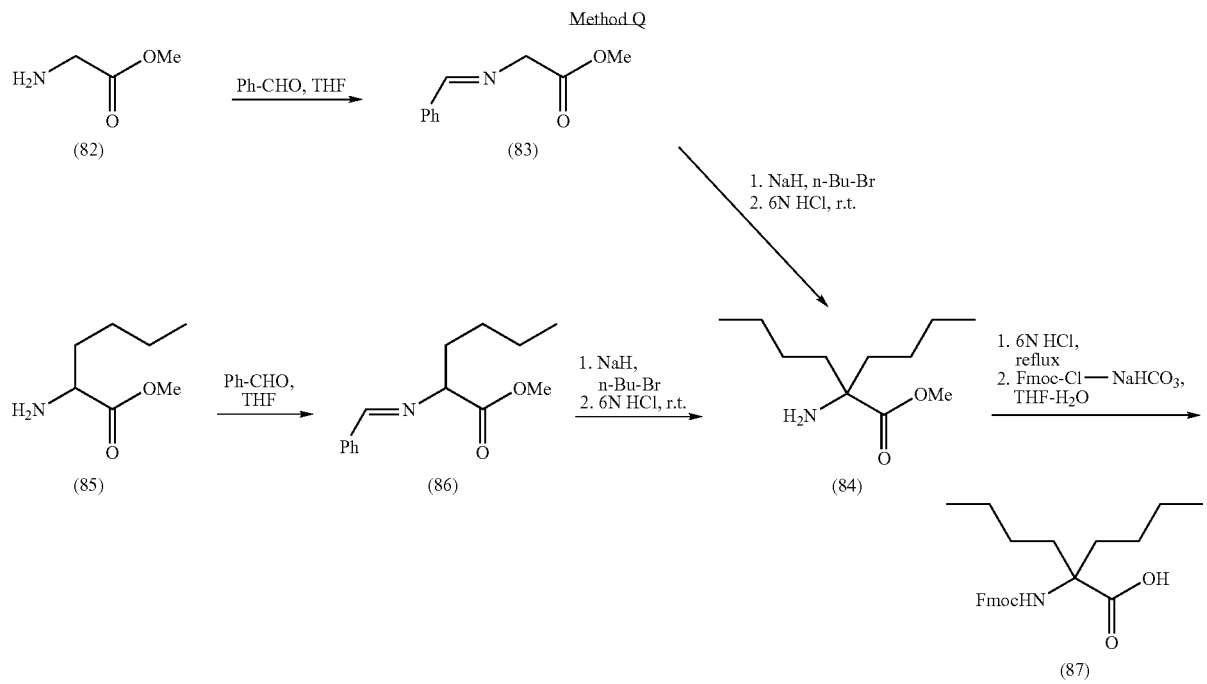

Method Q butyl reagent the scheme will yield a variety of disubstituted (R, R') amino acid surrogates where R and R' are different.

Synthesis of Disubstituted (R, R') Scaffolds (Method R)

The invention further provides for peptidomimetics in which surrogates are employed with two R groups, R and R'. The following method describes synthesis of Fmoc protected (R)-5,5-dibutyl-6-oxo-piperazine-2-carboxylic acid, where R and R' are each groups corresponding to a norleucine side chain moiety. It may be seen that the method below may be modified, based in part on the foregoing methods, to produce similar disubstituted (R, R') amino acid surrogates. Similar methods may be employed such that starting with any appropriate amino acid derivative (a compound similar to compound (84)) the scheme can yield a variety of disubstituted (R, R') amino acid surrogates where R and R' are different.

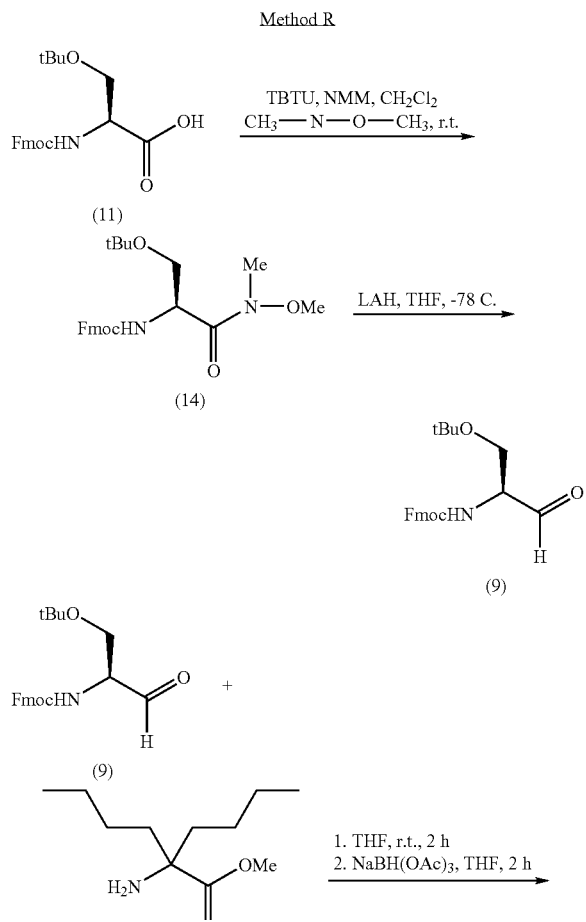

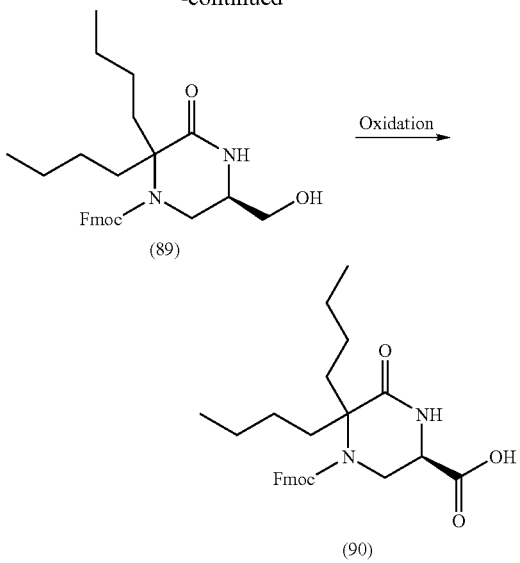

Synthesis of (2-Fmoc-amino-3-tert-butoxy-propylamino)-2,2,di-n-butyl acetic acid methyl ester (88): A suspension of 21 mmol of (84, scheme Q), and 2.9 mL (21 mmol) of triethyl amine in 50 mL of dry tetrahydrofuran, is stirred at room temperature for 45 minutes, and then a solution of ~20 mmol crude Fmoc-(O-t-butyl)-serinal (9, scheme D) in 30 mL of tetrahydrofuran is added, followed by 1.7 g of 4 Å powdered molecular sieves, and the suspension is stirred for an additional 2 hours. 6.4 g (30 mmol) of solid sodium triacetoxyborohydride is added, and the suspension stirred at room temperature overnight. The suspension is diluted with methanol, the molecular sieves filtered, and the filtrate concentrated. The residue is partitioned between 100 mL of ethyl acetate and 50 mL of water. The organic layer is dried over sodium sulfate, filtered, and concentrated. Compound (88) is purified by silica gel column chromatography.

Synthesis of 4-Fmoc-6-hydroxymethyl-3,3-di-n-butyl-piperazin-2-one (89): A solution of 10 mmol of compound (88) in 30 mL of 30% diethyl amine in ethyl acetate is stirred at room temperature overnight, and then concentrated to dryness. The residue is dissolved in 20 mL of tetrahydrofuran and 10 mL of water, 2.52 g (30 mmol) of solid sodium bicarbonate is added, followed by 3.36 g (13 mmol) of Fmoc-Cl. The mixture is stirred for 3 hours, diluted with 50 mL of ethyl acetate, the layers separated, and the organic layer washed with 30 mL of water, dried over magnesium sulfate, and concentrated. The crude mixture is dissolved in a solution of 10 mL of 90% trifluoroacetic acid in dichloromethane, stirred for 2 hours, and then concentrated to dryness. The residue is dissolved in ethyl acetate and washed with 50 mL of a saturated solution of sodium bicarbonate, dried over magnesium sulfate, and concentrated. Compound (89) is purified by silica gel column chromatography.

Synthesis of 4-Fmoc-5,5-di-n-butyl-6-oxo-piperazine-2-carboxylic acid (90): To a solution of 8 mmol alcohol (89) in 81 mL of acetonitrile kept at room temperature, is added phosphate buffer solution (prepared with 0.72 g of sodium phosphate monobasic and 1.43 g of sodium phosphate dibasic in 29.5 mL of water), followed by the addition of 0.33 g (2.1 mmol) of TEMPO, and 1.86 g (16.5 mmol) of sodium chlorite, and the biphasic solution is placed in an oil bath kept at 43° C. A solution of 4.3 mL (2.6 mmol) of sodium hypochlorite solution (prepared by mixing 1.9 mL of 10-13% sodium hypochlorite solution, and 2.4 mL of water) is added slowly. The reaction is stirred at 43° C. for 4 hours, cooled to room temperature, 20 mL of 10% sodium hydrogen sulfite added, stirred for 10 minutes, diluted with 50 mL of ethyl acetate, and the layers separated. The organic layer is washed with 1×10 mL of brine, 1×10 mL of 1N hydrochloric acid solution, dried over sodium sulfate, and concentrated. Compound (90) is purified by silica gel column chromatography.

7. Synthetic Methods for Peptidomimetics Including Surrogates

The peptidomimetics including one or more surrogates of formula I as disclosed in the several embodiments of this invention may be readily synthesized by any known conventional procedure for the formation of a peptide linkage between amino acids. Such conventional procedures include, for example, any solution phase procedure permitting a condensation between the free α-amino group of an amino acid residue having its carboxyl group or other reactive groups protected and the free primary carboxyl group of another amino acid residue having its amino group or other reactive groups protected. In a preferred conventional procedure, the peptidomimetics of this invention may be synthesized by solid-phase synthesis and purified according to methods known in the art. The amino acid surrogates may be incorporated into peptidomimetics of this invention by methods substantially similar to or identical to those employed with residues. Any of a number of well-known procedures utilizing a variety of resins and reagents may be used to prepare the peptidomimetics of this invention.

The process for synthesizing the peptidomimetics may be carried out by a procedure whereby each amino acid or amino acid surrogate in the desired sequence is added one at a time in succession to another amino acid residue or amino acid surrogate or by a procedure whereby peptide fragments with the desired amino acid sequence, which may include one or more amino acid surrogates, are first synthesized conventionally and then condensed to provide the desired peptidomimetics. The resulting peptidomimetic may optionally be cyclized to yield a cyclic peptidomimetic of the invention.

Solid phase peptide synthesis methods are well known and practiced in the art. In such methods the synthesis of compounds of the invention can be carried out by sequentially incorporating the desired amino acid residues or amino acid surrogates one at a time into the growing peptide chain according to the general principles of solid phase methods. These methods are disclosed in numerous references, including Merrifield R. B., Solid phase synthesis (Nobel lecture). *Angew. Chem.* 24:799-810 (1985) and Barany et al., *The Peptides, Analysis, Synthesis and Biology*, Vol. 2, Gross E. and Meienhofer J., Eds. Academic Press, 1-284 (1980).

In chemical syntheses of peptidomimetics, reactive side chain groups of the various amino acid residues or amino acid surrogates are protected with suitable protecting groups, which prevent a chemical reaction from occurring at that site until the protecting group is removed. Also common is the protection of the α-amino group of an amino acid residue or amino acid surrogate while that entity reacts at the carboxyl group, followed by the selective removal of the α-amino protecting group to allow a subsequent reaction to take place at that site. Specific protecting groups have been disclosed and are known in solid phase synthesis methods and solution phase synthesis methods.

α-amino groups may be protected by a suitable protecting group, including a urethane-type protecting group, such as benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropoxycarbonyl, 9-fluorenylmethoxycarbonyl (Fmoc) and p-methoxybenzyloxycarbonyl (Moz); aliphatic urethane-type protecting groups, such as t-butyloxycarbonyl (Boc), diisopropylmethoxycarbonyl, isopropoxycarbonyl, and allyloxycarbonyl. Fmoc is preferred for α-amino protection.

Guanidino groups may be protected by a suitable protecting group, such as nitro, p-toluenesulfonyl (Tos), Z, pentamethylchromanesulfonyl (Pmc), adamantyloxycarbonyl, pentamethyldihydrobenzofuran-5-sulfonyl (Pbf), Fmoc and Boc. Pbf is one preferred protecting group for Arg. Other preferred protecting groups include Z, Fmoc, and Boc. It is to be understood that particularly guanidino protecting groups may be cleaved and removed during the synthetic process, or may alternatively not be cleaved or removed, in which event the side chain with the protecting group forms a derivative of an amino acid side chain moiety as defined herein. Particularly where the protecting group is labile, and may be removed by some mechanism in vivo upon administration to a patient, the peptidomimetic becomes a "prodrug", which is to say a compound that is a drug precursor which, following administration to a patient, is converted to the desired drug form in vivo via some chemical or physiological process (e.g., a prodrug on being brought to physiological pH or through enzyme action is converted to the desired drug form).

The peptidomimetics of the invention described herein can be prepared using solid phase synthesis, either manually or by means of an automated peptide synthesizer, using programming modules as provided by the manufacturer and following the protocols set forth by the manufacturer, or by modifications of the manufacturer's protocols to improve the yield of difficult couplings.

Solid phase synthesis is conveniently commenced from the C-terminal end of the peptidomimetic by coupling a protected α-amino acid, α-amino acid surrogate or α-amino alcohol mimetic to a suitable resin. Such starting material is prepared by attaching an α-amino-protected amino acid or α-amino-protected amino acid surrogate by an ester linkage to a p-benzyloxybenzyl alcohol (Wang) resin or a 2-chlorotrityl chloride resin, by an amide bond between an Fmoc-Linker, such as p-[(R,S)-α-[1-(9H-fluor-en-9-yl)-methoxyformamido]-2,4-dimethyloxybenzyl]-phenoxyacetic acid (Rink linker) to a benzhydrylamine (BHA) resin, or by other means well known in the art, such as by attaching an α-amino-protected alcohol mimetic to 3,4-dihydro-2H-pyran-2-yl-methanol linker attached to chloromethyl polystyrene resin. Fmoc-Linker-BHA resin supports are commercially available and generally used when feasible. The resins are carried through repetitive cycles as necessary to add amino acids sequentially. The α-amino Fmoc protecting groups are removed under basic conditions. Piperidine, piperazine, diethylamine, or morpholine (20-40% v/v) in N,N-dimethylformamide (DMF) may be used for this purpose.

Following removal of the α-amino protecting group, the subsequent protected amino acids or amino acid surrogates are coupled stepwise in the desired order to obtain an intermediate, protected peptide-resin. The activating reagents used for coupling of the amino acids in the solid phase synthesis of the peptides are well known in the art. After the peptidomimetic is synthesized, if desired, the orthogonally protected side chain protecting groups may be removed using methods well known in the art for further derivatization of the compound.

Reactive groups in a peptidomimetic can be selectively modified, either during solid phase synthesis or after removal from the resin. For example, compounds can be modified to obtain N-terminus modifications, such as acetylation, while on resin, or may be removed from the resin by use of a cleaving reagent and then modified. Methods for N-terminus modification, such as acetylation, or C-terminus modification, such as amidation or introduction of an N-acetyl group, are known in the art. Similarly, methods for modifying side chains of amino acids are well known to those skilled in the art of peptide synthesis. The choice of modifications made to reactive groups present on the peptidomimetic will be determined, in part, by the characteristics that are desired in the peptidomimetic.

The peptidomimetics are, in one embodiment, cyclized prior to cleavage from the resin. For cyclization through reactive side chain moieties, the desired side chains are deprotected, and the compound suspended in a suitable solvent and a cyclic coupling agent added. Suitable solvents include, for example DMF, dichloromethane (DCM) or 1-methyl-2-pyrrolidone (NMP). Suitable cyclic coupling reagents include, for example, 2-(1H-benzotriazol-1-yl)-1,1,3,3-tetramethyluronium tetrafluoroborate (TBTU), 2-(1H-benzotriazol-1-yl)-1,1,3,3-tetramethyluronium hexafluorophosphate (HBTU), benzotriazole-1-yl-oxy-tris(dimethylamino)phosphonium-hexafluorophosphate (BOP), benzotriazole-1-yl-oxy-tris(pyrrolidino)phosphoniumhexafluorophosphate (PyBOP), 2-(7-aza-1H-benzotriazol-1-yl)-1,1,3,3-tetramethyluronium tetrafluoroborate (TATU), 2-(2-oxo-1(2H)-pyridyl)-1,1,3,3-tetramethyluronium tetrafluoroborate (TPTU) or N,N'-dicyclohexylcarbodiimide/1-hydroxybenzotriazole (DCCI/HOBt). Coupling is conventionally initiated by use of a suitable base, such as N,N-diispropylethylamine (DIPEA), sym-collidine or N-methylmorpholine (NMM).

Following cleavage of peptidomimetics from the solid phase following synthesis, the peptidomimetic can be purified by any number of methods, such as reverse phase high performance liquid chromatography (RP-HPLC), using a suitable column, such as a $C_{18}$ column. Other methods of separation or purification, such as methods based on the size or charge of the peptidomimetic, can also be employed. Once purified, the peptidomimetic can be characterized by any number of methods, such as high performance liquid chromatograph (HPLC), amino acid analysis, mass spectrometry, and the like.

Peptidomimetics of the present invention with a substituted amide derivative C-terminus, typically an N-alkyl group, are prepared by solid phase synthesis commenced from the C-terminal end of the peptidomimetic by coupling a protected α-amino acid or amino acid surrogate to a suitable resin. Such methods for preparing substituted amide derivatives on solid phase have been described in the art. See, for example, Barn D. R., Morphy J. R., Rees D. C. Synthesis of an array of amides by aluminum chloride assisted cleavage of resin-bound esters. *Tetrahedron Lett.* 37, 3213-3216 (1996); DeGrado W. F., Kaiser E. T. Solid-phase synthesis of protected peptides on a polymer bound oxime: Preparation of segments comprising the sequences of a cytotoxic 26-peptide analogue. *J. Org. Chem.* 47:3258-3261 (1982). Such starting material can be prepared by attaching an α-amino-protected amino acid or amino acid surrogate by an ester linkage to a p-benzyloxybenzyl alcohol (Wang) resin by well known means. The peptide chain is grown with the desired sequence of amino acids or amino acid surrogates, the product cyclized and resin-treated with a solution of appropriate amine and aluminum chloride (such as methyl amine, dimethyl amine, ethylamine, and so on) in dichloromethane. The resulting amide derivative peptidomimetic is released in solution from the resin. The resin is filtered and the amide derivative peptidomimetic recovered by concentration of solvent followed by precipitation with ether. The crude peptidomimetic is dried and remaining amino acid side chain protective groups cleaved using trifluoroacetic acid (TFA) in the presence of water and 1,2-ethanedithiol (EDT). The final product is precipitated by adding cold ether and collected by filtration. Final purification is by RP-HPLC using a $C_{18}$ column.

In one preferred method, peptidomimetics are synthesized by the following methods. Each of the peptidomimetics has one or two amino acid surrogates based on a keto-piperazine structure. The amino acid surrogates were synthesized as described above. The peptidomimetics are synthesized using Fmoc chemistry. A manual synthetic approach is used for couplings immediately before and after incorporation of the keto-piperazine amino acid surrogate.

The following protocol is employed to attach an amino acid surrogate to resin, such as where the amino acid surrogate was in a terminal position. Rink amide resin (loading at 0.3 mmol/g, Advanced ChemTech) is allowed to swell in DMF for 30 minutes. Fmoc deprotection of the resin was accomplished using 20% piperidine/DMF for 20 minutes. Coupling of the resin with the selected Fmoc-protected keto-piperazine amino acid surrogate (2 eq) is accomplished by overnight incubation in DMF with PyBop (2 eq) and DIEA (4 eq). If following Kaiser testing a positive result is obtained, the coupling reaction is conducting a second time. Acetylation, if required, is carried out using $Ac_2O$ (10 eq) and pyridine (20 eq) in DMF.

The following protocol is employed to attach a keto-piperazine amino acid surrogate to peptide-resin. Coupling is carried out by mixing Fmoc-protected keto piperazine amino acid surrogate (2 eq), TBTU (2 eq) and DIEA (4 eq) in DMF and overnight incubation, again with a repeat of the coupling reaction if a positive Kaiser test is obtained. Acetylation is carried out using $Ac_2O$ (10 eq) and pyridine (20 eq) in DMF.

The following protocol is employed to couple an Fmoc-protected amino acid to a keto-piperazine amino acid surrogate on solid phase. In most instances at least two coupling cycles were needed, and frequently three cycles were employed. In a typical cycle Fmoc-protected amino acid (4 eq) is mixed with HOAt (4 eq) and DIC (4 eq) in DMF for 30 minutes. The resulted mixture is then mixed overnight in a SPE tube with a keto-piperazine amino acid surrogate attached directly or through intermediates to resin.

Couplings between amino acids that were not directly adjacent to a keto-piperazine amino acid surrogate in the sequence are conducted using standard protocols for solid phase peptide synthesis.

The following protecting groups are employed: Boc for Lys and Orn, t-Butyl for Tyr and Ser, Trityl for Cys and His, O-t-Butyl for Asp and Pbf for Arg.

Peptidomimetics are cleaved from resin employing a mixture of TFA/thioanisole/phenol/$H_2O$/EDT (87.5/2.5/2.5/5/2.5) (5 mL) for 3 hours. The resulting material is filtered and precipitated from cold ether under freezing conditions for one hour.

For peptidomimetic compounds containing cysteine or other amino acid residues with reactive sulfhydrals, which are intended to be cyclized by means of disulfide bond formation, the precipitated cysteinyl peptidomimetic is washed with cold ether at least three times before being use in an oxidation step. For cyclization to form disulfide bonds via air oxidation, crude cysteinyl compound is dissolved in a mixture of acetonitrile and water. The pH of the reaction mixture is adjusted to 7-8 using 5% $NH_4OH$. The resulted solution is stirred slowly with 150 mg granular activated carbon for 2 days. Completion of cyclization is confirmed by LC-MS analysis before proceeding to the next process step. After cyclization, solid carbon is filtered from solution. The filtrate is lyophilized or dried in a speed-vac to obtain crude cyclic compound.

For peptidomimetic compounds intended to be cyclized by means of a lactam bridge, in one embodiment the lactam bridge may be formed prior to cleavage of the peptidomimetic from the resin. A peptidomimetic-resin is synthesized with orthogonally protected amino acid side chain functionalities forming the bridge. For example, orthogonal side chains protection may comprise an alloc group for side chain amine group protection and an allyl ester group for carboxyl protection. After synthesis of the peptidomimetic on the resin, both the alloc and allyl ester groups can be selectively removed, such as by treating the peptidomimetic-resin with Pd(PPh$_3$)$_4$/ PhSiH$_3$. The resulting groups are then condensed to form a lactam bridge using a condensation reagent such as PyBOP, HBTU, TBTU, TATU, or DIC/HOBt in the presence of a base such as DIPEA or NMM.

Alternatively, Nde (1-(4-nitro-1,3-dioxo-indan-2-ylidene) ethyl) or ivDde (1-(4,4-dimethyl-2-6-dioxo-cyclohexylidene)-3-methyl-butyl) can be employed as the side chain amino protecting group and side chain and ODmab ester (4-(N(1(4,4-dimethyl-2,6-dioxocyclohexylidene)-3-methyl-butyl)amino)benzyl ester) as the side chain carboxylic acid protecting group. Both of these groups can be removed by treatment of the peptide-resin with 2% hydrazine in DMF. In yet other aspect, the amino side chain functionality can be protected with Mtt (4-methyl trityl) and the carboxylic side chain functionality can be protected with OPip ester (phenyl isopropyl ester), both of which are removed selectively by treating the peptide resin with 1% TFA in DCM.

Following cleavage of peptides from the solid phase following their synthesis, the peptide can be purified by any number of methods, such as reverse phase high performance liquid chromatography (RP-HPLC), using a suitable column, such as a C$_{18}$ column. Other methods of separation or purification, such as methods based on the size or charge of the peptide, can also be employed. Once purified, the peptide can be characterized by any number of methods, such as high performance liquid chromatograph (HPLC), amino acid analysis, mass spectrometry, and the like.

Certain compounds of the invention, where the surrogate of formula I is bound to resin or other peptide solid support and is at the C-terminal position, may be synthesized by means of the following scheme.

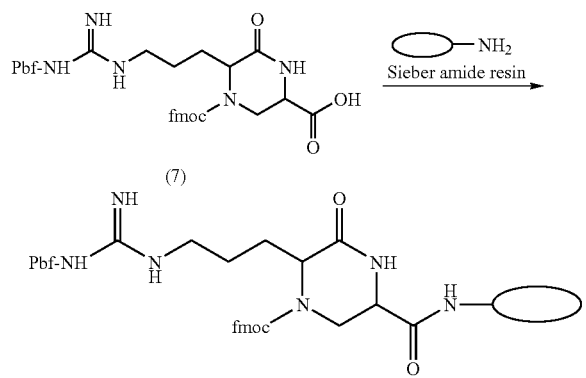

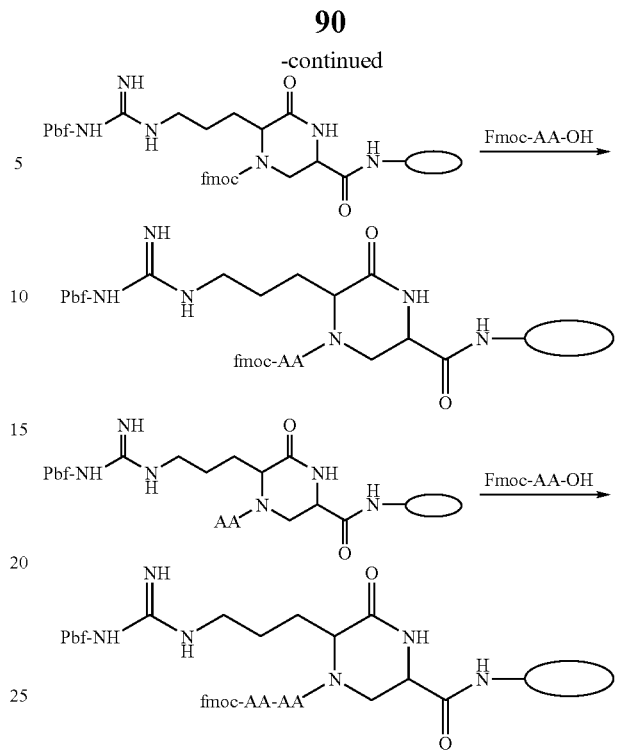

Surrogate (7) is prepared by the scheme of method A above, or any alternative method. Fmoc protected Sieber amide resin was treated by swelling the resin in a 1:1 mixture of dimethylformamide and dichloromethane for 45 minutes, followed by filtering and washing with dimethylformamide. The washed resin is then deprotected with 20% piperidine in dimethylformamide for 15 minutes, filtered, and washed with dimethylformamide.

A solution of Fmoc-protected surrogate (7) in dimethylformamide is added to the deprotected Sieber amide resin as prepared above, followed by solid PyBop and diisopropylethylamine, followed by additional dimethylformamide. The mixture is agitated overnight with nitrogen bubbling. The resin is filtered and washed with dimethylformamide, capped with capping solution consisting of a 3:2:1 solution of dimethylformamide:acetic anhydride:pyridine for 30 minutes, filtered, and washed with dimethylformamide to provide surrogate (7) complexed to resin.

The resulting Fmoc-protected surrogate (7) complexed to resin is deprotected with 20% piperidine in dimethylformamide for 15 minutes, filtered, and washed with dimethylformamide to yield surrogate (7) complexed to resin. A solution of the desired Fmoc-AA-OH (4 eq, where AA is any desired amino acid) in dimethylformamide is added to surrogate (7) complexed to resin, followed by a solution of HCTU (60 mmol, 4 eq), and diisopropylethylamine (120 mmol, 8 eq) in DMF and coupled overnight with nitrogen bubbling. The resulting Fmoc-AA-surrogate (7)-resin is isolated by filtration and washed with dimethylformamide. In order to ensure complete coupling, the product can be again treated with a solution of Fmoc-AA-OH as above overnight with nitrogen bubbling. The resulting resin is filtered and washed with dimethylformamide.

The resulting Fmoc-AA-surrogate (7)-resin is then capped with capping solution as above for 30 minutes. The resin is then filtered, washed with dimethylformamide, dichloromethane, MeOH, and diethyl ether, and then dried under vacuum.

Thereafter each succeeding amino acid is coupled using conventional peptide coupling methods.

Optional PEGylation of compounds made employing a surrogate of formula I may be performed, including by the methods described below.

PEGylation of reactive amine groups, such as lysine or ornithine side chains, an omega amino aliphatic in the N-terminal position, or an amine group of a surrogate of formula I in the C-terminal position, is accomplished by dissolving 0.005 mmol purified compound in 2 mL of dimethylsulfoxide, followed by the addition of 55.5 mg (0.011 mmol, 2 eq) of PEG-5K-OSu (5,000 Da MW methoxy-PEG with a succinimidyl propionate reactive group), with 17.7 µL (0.13 mmol, 20 eq) of triethyl amine then added, with the solution stirred at room temperature for 3 hours. Excess PEG-5K-OSu is quenched by the addition of 7 µL (0.111 mmol, 10 eq) of ethanol amine, and the reaction stirred overnight.

PEGylation of reactive carboxyl groups, such as Asp or Glu side chains or a terminal carboxyl on a compound on either a terminal amino acid residue or a terminal surrogate of formula I, is accomplished by coupling PEG-NH$_2$ (PEG-amine), to the peptidomimetic containing a carboxylate group in the side chain of Asp or Glu or at the C-terminus. The peptidomimetic (0.005 mmol) is dissolved in DMSO (2 mL), followed by the addition of 55.5 mg (0.011 mmol, 2 eq) of PEG-NH$_2$ and HOBt (0.01 mmol). The coupling is started by the addition of 0.0055 mmole of coupling reagent N-ethyl-N'-(3-dimethylaminopropyl)-carbodiimide (EDAC). The slightly cloudy solution stirred at room temperature overnight. The PEGylated peptidomimetic is then purified by HPLC.

PEGylation of reactive thiol groups, such as Cys or Hcys side chains or a thiol group in R$^1$ of the surrogate of formula I, is accomplished by treating the peptidomimetic in DMSO with PEG-methyl-maleimide reagent (SunBio, Orinda, Calif.) overnight. The PEGylated peptidomimetic is then purified by HPLC.

Following PEGylation, the resulting crude peptidomimetic mixture is purified by HPLC, yielding a PEG derivatized peptidomimetic including one or more amino acid surrogates.

In related aspects, hydroxyethyl starch (HES), and generally hydroxyalkyl starch (HAS), may be employed as a prosthetic group, rather than PEG, and similarly serves as a macromolecular carrier. Methods of use of HES and HAS for conjugation of drug are described in WO1999/042139; EP1476470, US2005/0063943 and US 2007/0134197, among others, and are incorporated herein by reference.

In addition, Fc fragments of immunoglobulin, such as IgG, can also be employed as a macromolecular carrier. A method of preparing this macromolecule and its conjugation to biologically active groups and drugs is described in WO2005/047334, incorporated herein by reference.

The PEG, HES, HAS and Fc conjugation is employed to improve the in vivo pharmacokinetic and pharmacodynamic profile of the peptidomimetics of this invention by improving their in vivo stability and half lives.

8. Assay Systems for Peptidomimetics

The melanocortin receptor-specific peptidomimetics of this invention may be tested by a variety of assay systems to determine binding and functional status.

Competitive inhibition assay using [I$^{125}$]-NDP-α-MSH. A competitive inhibition binding assay was performed using membrane homogenates prepared from HEK-293 cells that express recombinant hMC4-R, hMC3-R, or hMC5-R, and from B-16 mouse melanoma cells (containing endogenous MC1-R). In some instances, HEK-293 cells that express recombinant hMC1-R were employed. In the examples that follow, all MC3-R, MC4-R and MC5-R values are for human recombinant receptors. MC1-R values are for B-16 mouse melanoma cells, unless the heading is "hMC1-R", in which case the value is for human recombinant MC1-R. Assays were performed in 96 well GF/B Millipore multiscreen filtration plates (MAFB NOB10) pre-coated with 0.5% bovine serum albumin (Fraction V). Membrane homogenates were incubated with 0.2 nM (for hMC4-R) 0.4 nM (for MC3-R and MC5-R) or 0.1 nM (for mouse B16 MC1-R or hMC1-R) [I$^{125}$]-NDP-α-MSH (Perkin Elmer) and increasing concentrations of test peptidomimetics in buffer containing 25 mM HEPES buffer (pH 7.5) with 100 mM NaCl, 2 mM CaCl$_2$, 2 mM MgCl$_2$, 0.3 mM 1,10-phenanthroline, and 0.2% bovine serum albumin. After incubation for 60 minutes at 37° C., the assay mixture was filtered and the membranes washed three times with ice-cold buffer. Filters were dried and counted in a gamma counter for bound radioactivity. Non-specific binding was measured by inhibition of binding of [I$^{125}$]-NDP-α-MSH in the presence of 1 µM NDP-α-MSH. Maximal specific binding (100%) was defined as the difference in radioactivity (cpm) bound to cell membranes in the absence and presence of 1 µM NDP-α-MSH. Radioactivity (cpm) obtained in the presence of test compounds was normalized with respect to 100% specific binding to determine the percent inhibition of [I$^{125}$]-NDP-α-MSH binding. Each assay was conducted in triplicate and the actual mean values are described, with results less than 0% reported as 0%. Ki values for test peptidomimetics were determined using Graph-Pad Prism® curve-fitting software.

Competitive binding assay using [I$^{125}$]-AgRP (83-132). Competitive binding studies using [I$^{125}$]-AgRP (83-132) were carried out using membrane homogenates isolated from cells that express hMC4-R. The assays were performed in 96-well GF/B Millipore multiscreen filtration plates (MAFB NOB10) pre-coated with 0.5% bovine serum albumin (Fraction V). The assay mixture contained 25 mM HEPES buffer (pH 7.5) with 100 mM NaCl, 2 mM CaCl$_2$, 2 mM MgCl$_2$, 0.3 mM 1,10-phenanthroline, 0.5% bovine serum albumin, membrane homogenates, radioligand [I$^{125}$]-AgRP (83-132) (Perkin Elmer) and increasing concentrations of peptidomimetics in a total volume of 200 µL. Binding was measured at radioligand concentrations of 0.2 nM. After incubating for 1 hour at 37° C., the reaction mixture was filtered and washed with assay buffer containing 500 mM NaCl. The dried discs were punched out from the plate and counted on a gamma counter. The total binding of the radioligand did not exceed 10% of the counts added to the reaction mixture. Ki values for test peptidomimetics were determined using Graph-Pad Prism® curve-fitting software.

Assay for agonist activity. Accumulation of intracellular cAMP was examined as a measure of the ability of the test peptidomimetics to elicit a functional response in HEK-293 cells that express MC4-R. Confluent HEK-293 cells that express recombinant hMC4-R were detached from culture plates by incubation in enzyme-free cell dissociation buffer. Dispersed cells were suspended in Earle's Balanced Salt Solution containing 10 mM HEPES (pH 7.5), 1 mM MgCl$_2$, 1 mM glutamine, 0.5% albumin and 0.3 mM 3-isobutyl-1-methyl-xanthine (IBMX), a phosphodiesterase inhibitor. The cells were plated in 96-well plates at a density of 0.5×10$^5$ cells per well and pre-incubated for 30 minutes. Cells were exposed for 1 hour at 37° C. to test peptidomimetics dissolved in DMSO (final DMSO concentration of 1%) at a concentration range of 0.05-5000 nM in a total assay volume of 200 µL. NDP-α-MSH was used as the reference agonist. At the end of the incubation period, cells were disrupted by the addition of 50 μL of lysis buffer (cAMP EIA kit, Amersham) followed by vigorous pipetting. Levels of cAMP in the lysates were determined using a cAMP EIA kit (Amersham). Data analysis was performed by nonlinear regression analysis with Graph-Pad Prism® software. The maximum efficacies of the test peptidomimetics were compared to that achieved by the reference melanocortin agonist NDP-αMSH.

9. In Vivo Animal Tests for Peptidomimetics

Food intake after IN and IP dosing. Changes in food intake are evaluated for selected compounds. Male C57BL/6 mice are obtained from Jackson labs (Bar Harbor, Me.). Animals are individually housed in conventional plexiglass hanging cages and maintained on a controlled 12 hour on/off light cycle. Water and pelleted (Harlan Teklad 2018 18% Protein Rodent Diet) food is provided ad libitum. The mice are dosed IP (by intraperitoneal injection) after a 24 hour fast or IN (by intranasal administration) with vehicle or selected peptidomimetics (0.1-3 mg/kg, and in some cases up to 10 mg/kg). All animals are dosed once a day (or up to four consecutive days) at the start of the "lights off" period. The changes in food intake weight for the 4 hour and 20 hour period after dosing relative to control animals administered vehicle is determined.

Induction of Penile Erection. The ability of peptidomimetics of this invention to induce penile erection (PE) in male rats are evaluated with selected peptidomimetics. Male Sprague-Dawley rats weighing 200-250 g are kept on a 12 hour on/off light cycle with food and water ad libitum. All behavioral studies are performed between 10 a.m. and 5 p.m. Groups of 4-8 rats are administered peptidomimietics at a variety of doses via an intravenous (IV) route, and may alternatively be administered peptidomimetics by an intracerebroventricular (ICV) route. Immediately after treatment, rats are placed into individual polystyrene cages (27 cm long, 16 cm wide, and 25 cm high) for behavioral observation. Rats administered peptidomimetics by an IV route are observed for one hour, and the number of yawns, grooming bouts and PEs are recorded in 10-minute bins. For rats administered peptidomimietics by an ICV routes, rats are observed for two hours.

10. Combination Therapy with Peptidomimetics

Combination Therapy for Sexual Dysfunction. It is also possible and contemplated to use peptidomimetics of this invention in combination with other drugs or agents, such as for treatment of sexual dysfunction. These other drugs and agents may include agents that induce erectile activity, including phosphodiesterase-5 (PDE-5) inhibitors, testosterone, prostaglandin and the like. In a preferred embodiment of the invention, peptidomimetics of the invention are used in combination with a therapeutically effective amount of a cyclic-GMP-specific phosphodiesterase inhibitor or an alpha-adrenergic receptor antagonist. The teachings and disclosure of U.S. patent application Ser. No. 11/139,730, filed May 26, 2005, and entitled "Multiple Agent Therapy for Sexual Dysfunction", are incorporated here by reference as if set forth in full.

The present invention thus provides methods of treating sexual dysfunction, the methods comprising the step of administering to the patient having or at risk of having sexual dysfunction a therapeutically effective amount of a peptidomimetics of this invention in combination with a therapeutically effective amount of a second sexual dysfunction pharmaceutical agent. The peptidomimetics of this invention may be administered simultaneously with, prior to or subsequent to administration with a therapeutically effective amount of a second sexual dysfunction pharmaceutical agent. Preferably the peptidomimetics of this invention is administered within one hour, preferably within less than one-half hour, of administration of a therapeutically effective amount of a second sexual dysfunction pharmaceutical agent. However, for certain forms of combination therapy, such as for example in combination with a therapeutically effective amount of a hormone or hormone-related sexual dysfunction pharmaceutical agent, the hormone or hormone-related sexual dysfunction pharmaceutical agent may be administered on an independent schedule, such that there is no set or specific temporal relationship between administration of the peptidomimetics of this invention and the hormone or hormone-related sexual dysfunction pharmaceutical agent. Thus, for example, the hormone or hormone-related sexual dysfunction pharmaceutical agent may be administered on a daily or other dose, or by means of patches or other continuous administration schedules, with administration of the peptidomimetics of this invention when desired or needed by the patient.

The present invention thus provides methods of treating sexual dysfunction, the methods comprising the step of administering to a patient having or at risk of having sexual dysfunction a therapeutically effective amount of a peptidomimetics of this invention in combination with another compound that is useful in the treatment of sexual dysfunction. In a preferred embodiment of combination therapy the sexual dysfunction is female sexual dysfunction. In an especially preferred embodiment of combination therapy the sexual dysfunction is erectile dysfunction.

The present invention also provides pharmaceutical compositions that comprise a peptidomimetic of this invention and a second compound useful for the treatment of sexual dysfunction. In an embodiment of the composition, the additional compounds useful for the treatment of sexual dysfunction are preferably selected from but not limited to the group consisting of a phosphodiesterase inhibitor; a cyclic-GMP-specific phosphodiesterase inhibitor; prostaglandins; apomorphine; oxytocin modulators; α-adrenergic antagonists; androgens; selective androgen receptor modulators (SARMs); buproprion; vasoactive intestinal peptide (VIP); neutral endopeptidase inhibitors (NEP); and neuropeptide Y receptor antagonists (NPY).

In an embodiment of the method and composition, the second sexual dysfunction pharmaceutical agent is testosterone.

In another embodiment of combination therapy, the second sexual dysfunction pharmaceutical agent is a type V phosphodiesterase (PDE-5) inhibitor. For example, the PDE-5 inhibitor may be Viagra®, a brand of sildenafil, Levitra®, a brand of monohydrochloride salt of vardenafil, or Cialis®, a brand of tadalafil. Other PDE-5 inhibitors are disclosed in U.S. patent application Ser. No. 11/139,730, filed May 26, 2005, and entitled "Multiple Agent Therapy for Sexual Dysfunction", incorporated here by reference.

In another embodiment of the composition above, the second compound useful for the treatment of sexual dysfunction is an estrogen agonist/antagonist. In one embodiment, the estrogen agonist/antagonist is (−)-cis-6-phenyl-5-[-4-(2-pyrrolidin-1-yl-ethoxy)-phenyl]-5,6,7,8-tetrahydro-napththalene-2-ol (also known as lasofoxifene) or an optical or geometric isomer thereof; a pharmaceutically acceptable salt, N-oxide, ester, quaternary ammonium salt; or a prodrug thereof. More preferably, the estrogen agonist/antagonist is in the form of a D-tartrate salt.

In yet another embodiment of the composition above, the estrogen agonist/antagonist is selected from the group consisting of tamoxifen, 4-hydroxy tamoxifen, raloxifene, droloxifene, toremifene, centchroman, idoxifene, 6-(4-hydroxy-phenyl)-5-[4-(2-piperidine-1-yl-ethoxy)-benzyl]-napthalen-2-ol, {4-[2-(2-aza-bicyclo[2.2.1]hept-2-yl)-ethoxy]-phenyl}-[6-hydroxy-2-(4-hydroxy-phenyl)-benzo[b]thiophen-3-yl]-methanone, EM-652, EM-800, GW 5368, GW 7604, TSE-424 and optical or geometric isomers thereof; and pharmaceutically acceptable salts, N-oxides, esters, quaternary ammonium salts, and prodrugs thereof.

In yet another embodiment, a peptidomimetic of this invention may be used in combination with any known mechanical aids or devices.

The present invention also provides kits for the treatment of sexual dysfunction (including erectile dysfunction), the kits comprising: a first pharmaceutical composition including a peptidomimetic of this invention; a second pharmaceutical composition comprising a second compound useful for the treatment of sexual dysfunction; and, a container for the first and second compositions.

Combination Therapy and Weight Regulation. It is also possible and contemplated to use peptidomimetics of this invention in combination with other drugs or agents for treatment of various weight and feeding-related disorders. Peptidomimetics of this invention may be employed for decreasing food intake and/or body weight in combination with any other agent or drug heretofore employed as a diet aid, or for decreasing food intake and/or body weight. Peptidomimetics of this invention may further be employed for increasing food intake and/or body weight in combination with any other agent or drug heretofore employed for increasing food intake and/or body weight.

Drugs that reduce energy intake include, in part, various pharmacological agents, referred to as anorectic drugs, which are used as adjuncts to behavioral therapy in weight reduction programs. Classes of anorectic drugs include, but are not limited to, noradrenergic and serotonergic agents. Noradrenergic medications may be described as those medications generally preserving the anorectic effects of amphetamines but with weaker stimulant activity. The noradrenergic drugs, except phenylpropanolamine, generally act through a centrally mediated pathway in the hypothalamus that causes anorexia. Phenylpropanolamine, a racemic mixture of norephedrine esters, causes a release of norepinephrine throughout the body and stimulates hypothalamic adrenoreceptors to reduce appetite.

Suitable noradrenergic agents include, but are not limited to, diethylpropion such as TENUATE™ (1-propanone, 2-(diethylamino)-1-phenyl-, hydrochloride) commercially available from Merrell; mazindol (or 5-(p-chlorophenyl)-2,5-dihydro-3H-imidazo[2,1-a]isoindol-5-ol) such as SANOREX™ commercially available from Novartis or MAZANOR™ commercially available from Wyeth Ayerst; phenylpropanolamine (or Benzenemethanol, alpha-(1-aminoethyl)-, hydrochloride); phentermine (or Phenol, 3-[[4,5-dihydro-1H-imidazol-2-yl]ethyl](4-methylphenyl)amino], monohydrochloride) such as ADIPEX-P™ commercially available from Lemmon, FASTIN™ commercially available from Smith-Kline Beecham and Ionamin™ commercially available from Medeva; phendimetrazine (or (2S,3S)-3,4-Dimethyl-2-phenylmorpholine L-(+)-tartrate (1:1)) such as METRA™ commercially available from Forest, PLEGINE™ commercially available from Wyeth-Ayerst; PRELU-2™ commercially available from Boehringer Ingelheim, and STATOBEX™ commercially available from Lemmon; phendamine tartrate such as THEPHORIN™ (2,3,4,9-Tetrahydro-2-methyl-9-phenyl-1H-indenol[2,1-c]pyridine L-(+)-tartrate (1:1)) commercially available from Hoffmann-LaRoche; methamphetamine such as DESOXYN™ Tablets ((S)—N, (alpha)-dimethylbenzeneethanamine hydrochloride) commercially available from Abbott; and phendimetrazine tartrate such as BONTRIL™ Slow-Release Capsules (-3,4-Dimethyl-2-phenylmorpholine Tartrate) commercially available from Amarin.

Suitable serotonergic agents include, but are not limited to, sibutramine such as MERIDIA™ capsules (a racemic mixture of the (+) and (−) enantiomers of cyclobutanemethanamine, 1-(4-chlorophenyl)-N,N-dimethyl-(alpha)-(2-methylpropyl)-, hydrochloride, monohydrate) commercially available from Knoll, fenfluramine such as Pondimin™ (Benzeneethanamine, N-ethyl-alpha-methyl-3-(trifluoromethyl)-, hydrochloride) commercially available from Robbins; dexfenfluramine such as Redux™ (Benzeneethanamine, N-ethyl-alpha-methyl-3-(trifluoromethyl)-, hydrochloride) commercially available from Interneuron. Fenfluramine and dexfenfluramine stimulate release of serotonin and inhibit its reuptake. Sibutramine inhibits the reuptake of serotonin, norepinephrine and dopamine, but does not stimulate secretion of serotonin.

Other serotonergic agents useful with the practice of the present invention include, but are not limited to, certain auoretic gene 5HT1a inhibitors (brain, serotonin) such as carbidopa and benserazide as disclosed by U.S. Pat. No. 6,207,699 which is incorporated herein by reference; and certain neurokinin 1 receptor antagonist and selective serotonin reuptake inhibitors including fluoxetine, fluvoxamine, paroxtine, sertraline and other useful compounds as disclosed by U.S. Pat. No. 6,162,805 which is incorporated herein by reference. Other potential agents that may be employed include, for example, 5HT2c agonists.

Other useful compounds for reducing energy intake include, but are not limited to, certain aryl-substituted cyclobutylalkylamines as disclosed by U.S. Pat. No. 6,127,424 which is incorporated herein by reference; certain trifluoromethylthiophenylethylamine derivatives as disclosed by U.S. Pat. No. 4,148,923 which is incorporated herein by reference; certain compounds as disclosed by U.S. Pat. No. 6,207,699 which is incorporated herein by reference; certain kainite or AMPA receptor antagonists as disclosed by U.S. Pat. No. 6,191,117 which is incorporated herein by reference; certain neuropeptide receptor subtype 5 as disclosed by U.S. Pat. No. 6,140,354 which is incorporated herein by reference; and certain alpha-blocking agents as disclosed by U.S. Pat. No. 4,239,763 which is incorporated herein by reference.

Moreover, several peptides and hormones regulate feeding behavior. For example, cholecystokinin and serotonin act to decrease appetite and food intake. Leptin, a hormone produced by fat cells, controls food intake and energy expenditure. In obese persons who are losing weight without medications, a decrease in weight is associated with a decrease in circulating levels of leptin, suggesting its role in weight homeostasis. Obese patients with high leptin levels are thought to have peripheral leptin resistance secondary to the down-regulation of leptin receptors. Non-limiting examples of useful compounds affecting feeding behavior include certain leptin-lipolysis stimulated receptors as disclosed by WO 01/21647 which is incorporated herein by reference; certain phosphodiesterase enzyme inhibitors as disclosed by WO 01/35970 which is incorporated herein by reference; certain compounds having nucleotide sequences of the mahogany gene as disclosed by WO 00/05373 which is incorporated herein by reference; and certain sapogenin compounds as disclosed by U.S. Pat. No. 4,680,289 which is incorporated herein by reference.

Other useful compounds include certain gamma peroxisome proliferator activated receptor (PPAR) agonists as disclosed by WO 01/30343 and U.S. Pat. No. 6,033,656 which are incorporated herein by reference and certain polypeptides such as fibroblast growth factor-10 polypeptides as disclosed by WO 01/18210 which is incorporated herein by reference.

Moreover, monoamine oxidase inhibitors that decrease energy intake or increase energy expenditure are useful with the practice of the present invention. Suitable, but non-limiting, examples of monoamine oxidase inhibitors include befloxatone, moclobemide, brofaromine, phenoxathine, esuprone, befol, toloxatone, pirlindol, amiflamine, sercloremine, bazinaprine, lazabemide, milacemide, caroxazone and other certain compounds as disclosed by WO 01/12176 which is incorporated herein by reference.

Certain compounds that increase lipid metabolism are also useful with the practice of the present invention. Such compounds include, but are not limited to, evodiamine compounds as disclosed by U.S. Pat. No. 6,214,831 which is incorporated herein by reference.

Nutrient partitioning agents and digestive inhibitors are another strategy in the treatment of obesity by interfering with the breakdown, digestion or absorption of dietary fat in the gastrointestinal tract. Gastric and pancreatic lipases aid in the digestion of dietary triglycerides by forming them into free fatty acids that are then absorbed in the small intestine. Inhibition of these enzymes leads to inhibition of the digestion of dietary triglycerides. Non-limiting examples include a lipase inhibitor, orlistat, such as XENICAL™ capsules ((S)-2-formylamino-4-methyl-pentanoic acid (S)-1-[[(2S,3S)-3-hexyl-4-oxo-2-oxetanyl]methyl]-dodecyl ester) commercially available from Roche Laboratories and certain benzoxazinone compounds as described by WO 00/40247 which is incorporated herein by reference.

Agents that increase energy expenditure are also referred to as thermogenic medications. Non-limiting examples of suitable thermogenic medications include xanthines, such as caffeine and theophylline, selective β-3-adrenergic agonists, for example certain compounds in U.S. Pat. No. 4,626,549 which is incorporated by reference herein, and α-2-adrenergic and growth hormones compounds as described in U.S. Pat. Nos. 4,937,267 and 5,120,713 which are incorporated by reference herein.

Generally, a total dosage of the above-described obesity control agents or medications, when used in combination with a peptidomimetic of this invention can range from 0.1 to 3,000 mg/day, preferably from about 1 to 1,000 mg/day and more preferably from about 1 to 200 mg/day in single or 2-4 divided doses. The exact dose, however, is determined by the attending clinician and is dependent on such factors as the potency of the compound administered, the age, weight, condition and response of the patient.

Agents or drugs employed for increasing food intake and/or body weight include appetite stimulants such as megestrol acetate, adrenocorticoids such as prednisolone and dexamethasone, cyproheptidine, serotonergic drugs such as fenfluramine, neuropeptide Y, and androgen antagonists such as flutamide, nilutamide, and zanoterone.

11. Illustrative Peptidomimetics of the Invention

As may be seen from the foregoing, the peptidomimetics of the invention consist of a large group that nonetheless is characterized by common elements, including an element based upon, or derived from, the melanocortin sequences His-Phe-Arg-Trp (SEQ ID NO:1) or His-D-Phe-Arg-Trp. The minimum total number of amino acid residues and surrogates in a peptidomimetic of the invention is four. While there is no maximum as such, in general the total number of amino acid residues and surrogates in a peptidomimetic of the invention will not exceed about ten. The peptidomimetics may be linear or cyclic. If cyclic, typically the peptidomimetics of the invention have at least six amino acid residues and surrogates, but five is possible if the peptidomimetics is cyclized through a C-terminus group or an N-terminus group.

In one aspect there are provided linear peptidomimetics, such as the following:

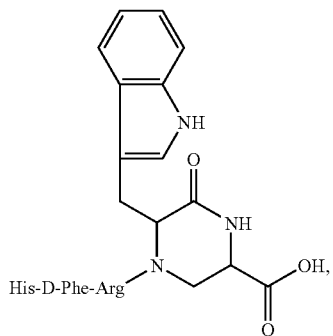

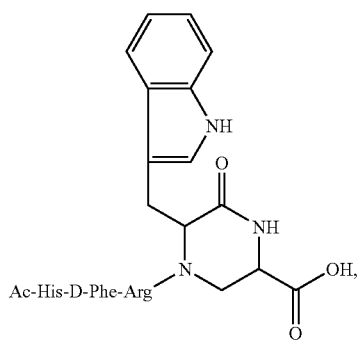

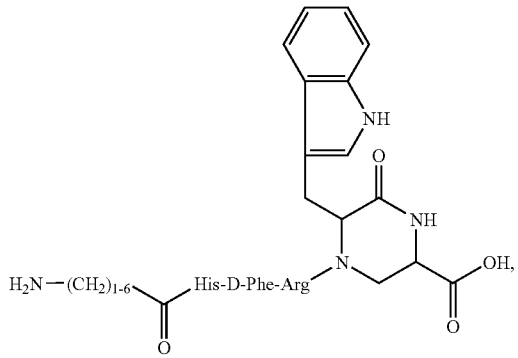

99
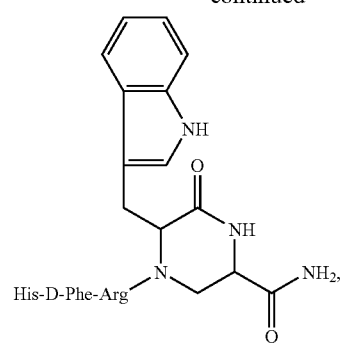
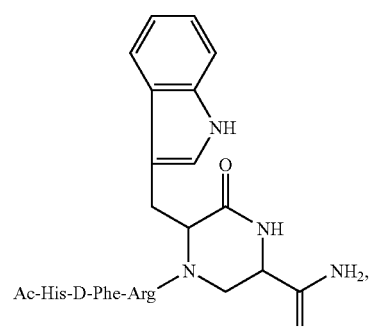
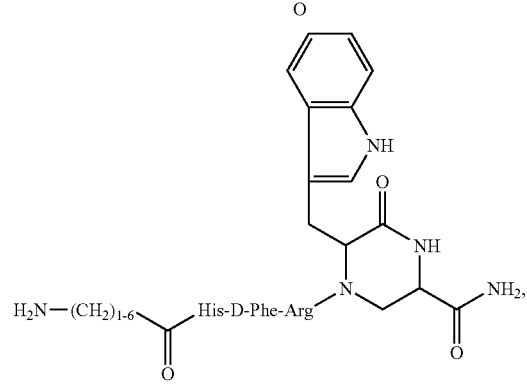
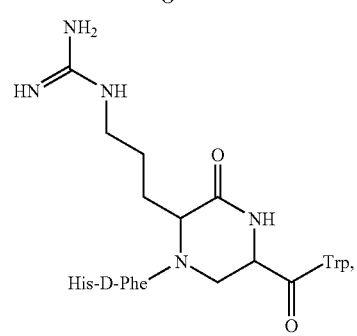
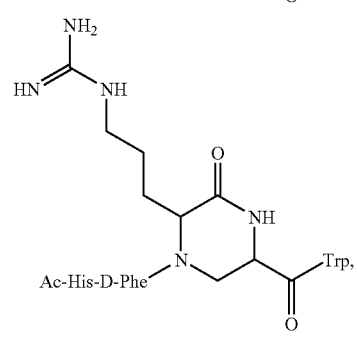
100
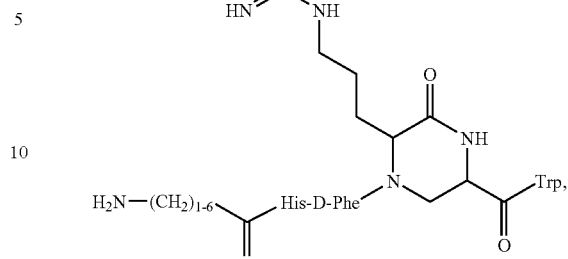
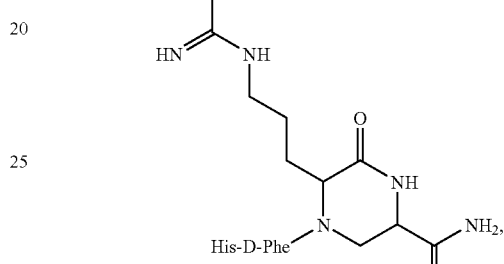
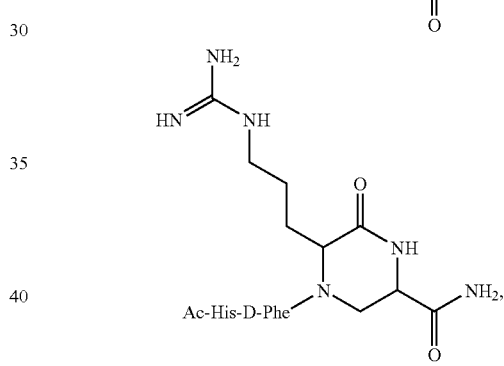
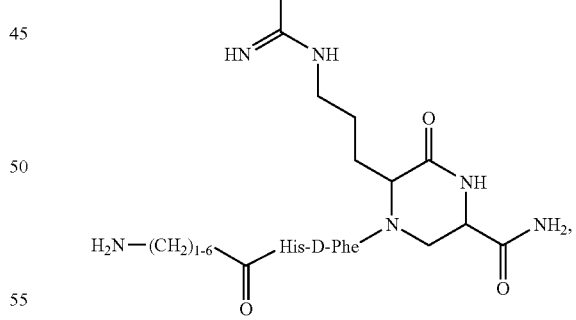
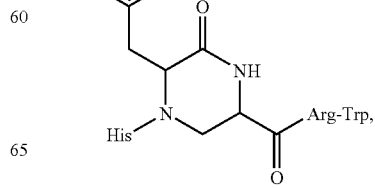

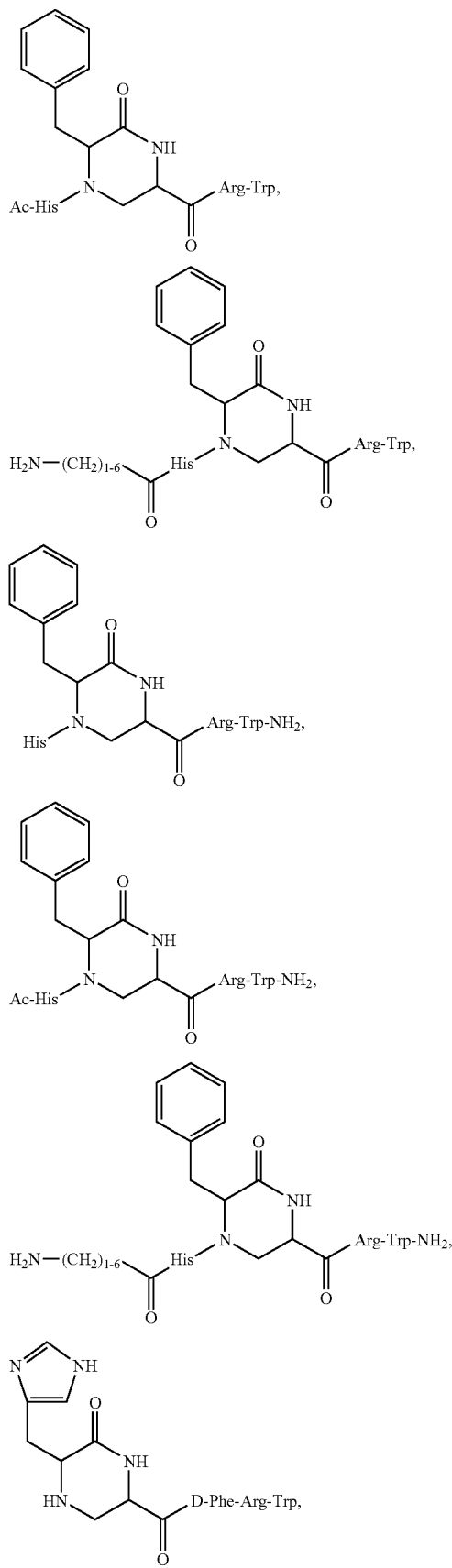

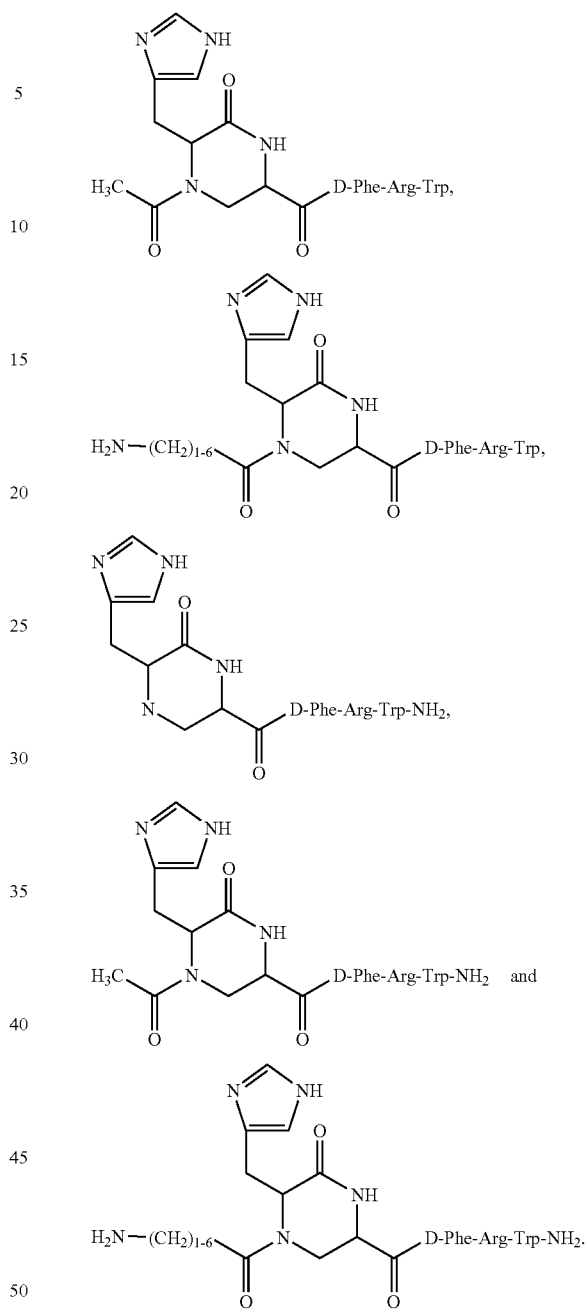

Even in the foregoing, it is possible and contemplated within the invention to make substitutions. By way of example and not limitation, the following substitutions are possible:

For His in position 1, there may be substituted an amino acid residue with an amino acid side chain moiety comprising an alkyl group, aryl group or a heteroaryl group, optionally fused to an aryl group, heteroaryl group, cycloalkyl group or heterocycloalkyl group, and optionally with one or two ring substituents, and when one or both ring substituents are present, the substituents are the same or different and independently hydroxyl, halogen, halo-alkyl, halo-aryl, alkyl, or aryl groups attached directly or through an ether linkage, or is an amino acid residue of the formulas

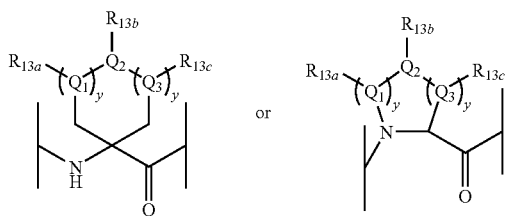

wherein:

$Q_1$, $Q_2$ and $Q_3$ are each independently $CH_2$, CH, C=O, NH, N, S or O;

$R_{13a}$ is not present if the y of $(Q_1)_y$ is 0 or if $Q_1$ is $CH_2$, C=O, NH, N with a double bond, S, or O, and otherwise $R_{13a}$ is a hydroxyl group, halogen group, or linear or branched $C_1$ to $C_7$ alkyl, aryl, heteroaryl, alkene, alkenyl, or aralkyl chain, in each instance attached directly or through an ether linkage to $Q_1$, on the proviso that $R_{13a}$ may form an aryl or heteroaryl with $R_{13b}$;

$R_{13b}$ is not present if $Q_2$ is $CH_2$, C=O, NH, N with a double bond, S, or O, and otherwise $R_{13b}$ is a hydroxyl group, halogen group, or linear or branched $C_1$ to $C_7$ alkyl, aryl, heteroaryl, alkene, alkenyl, or aralkyl chain, in each instance attached directly or through an ether linkage to $Q_2$, on the proviso that $R_{13b}$ may form an aryl or heteroaryl with either $R_{13a}$ or $R_{13c}$;

$R_{13c}$ is not present if the y of $(Q_3)_y$ is 0 or if $Q_3$ is $CH_2$, C=O, NH, N with a double bond, S, or O, and otherwise $R_{13c}$ is a hydroxyl group, halogen group, or linear or branched $C_1$ to $C_7$ alkyl, aryl, heteroaryl, alkene, alkenyl, or aralkyl chain, in each instance attached directly or through an ether linkage to $Q_3$, on the proviso that $R_{13c}$ may form an aryl or heteroaryl with $R_{13b}$; and y is in each instance independently 0 or 1;

or $S_2$ is a surrogate of formula I wherein $R^1$ is H or comprises alkyl, an aryl group or a heteroaryl group, optionally fused to an aryl group, heteroaryl group, cycloalkyl group or heterocycloalkyl group, and optionally with one or two ring substituents, and when one or both ring substitutents are present, the substituents are the same or different and independently hydroxyl, halogen, halo-alkyl, halo-aryl, alkyl, or aryl groups attached directly or through an ether linkage;

For D-Phe in position 2, there may be substituted an amino acid residue with an amino acid side chain moiety comprising phenyl, 1-naphthyl, or 2-naphthyl, optionally with one or two ring substituents, and when one or both ring substitutents are present, the substituents are the same or different and independently hydroxyl, halogen, halo-alkyl, halo-aryl, alkyl, or aryl groups attached directly or through an ether linkage, including but not limited to L- or D-Phe with any known substitutent, L- or D-NaI '1 or L- or D-NaI '2;

For Arg in position 3, there may be substituted an amino acid residue with an amino acid side chain moiety comprising an amino acid side chain moiety comprising a heteroatom unit with at least one cationic center, hydrogen bond donor or hydrogen bond acceptor wherein at least one heteroatom is nitrogen or oxygen; and For Trp in position 4, there may be substituted an amino acid residue with an amino acid side chain moiety comprising an aryl group, a cycloalkyl group, two fused aryl groups, two aryl groups joined by a bond or —O—, or a heteroaryl group fused with a heteroaryl, aryl, cycloalkyl or heterocycloalkyl group, optionally with one or two ring substituents, and when one or both ring substitutents are present, the substituents are the same or different and independently hydroxyl, halogen, halo-alkyl, halo-aryl, alkyl, or aryl groups attached directly or through an ether linkage.

It will readily be appreciated that similar peptidomimetics can be made that include more than three amino acid residues and a surrogate of formula I. By way of example, peptidomimetics may include four, five, six, seven, eight or nine amino acid residues and a surrogate of formula I. It is also contemplated that peptidomimetics may include more than one surrogate of formula I, such as including two surrogates of formula I, preferably where the $R^1$ groups of the surrogates are different. It will further readily be appreciated that peptidomimetics may be cyclic as well as linear, and in particular that peptidomimetics with at least about five, six, seven, eight or nine amino acid residues and a surrogate of formula I may be cyclized. The cyclic peptidomimetics may be have a cyclic bond that includes an N-terminus group, a C-terminus group, an $R^1$ group of a surrogate of formula I, or one or two amino acid side chain moieties. The cyclic bond may include a covalent bond such as an amide, disulfide, thioether, Schiff base, reduced Schiff base, imide, secondary amine, carbonyl, urea, hydrazone or oxime bond.

It is also possible and contemplated to make peptidomimetics containing two surrogates of formula I. By way of example, and not limitation, the following peptidomimetics are included within the invention:

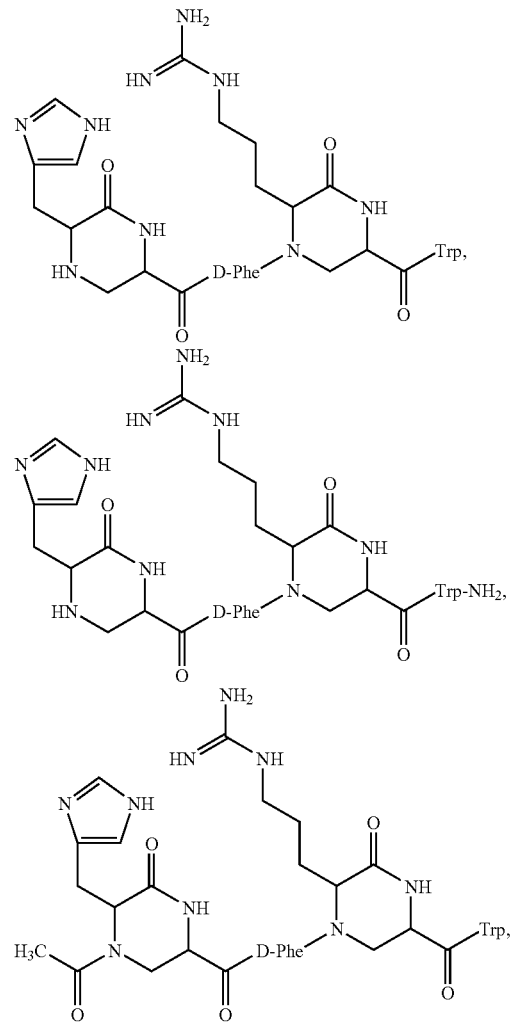

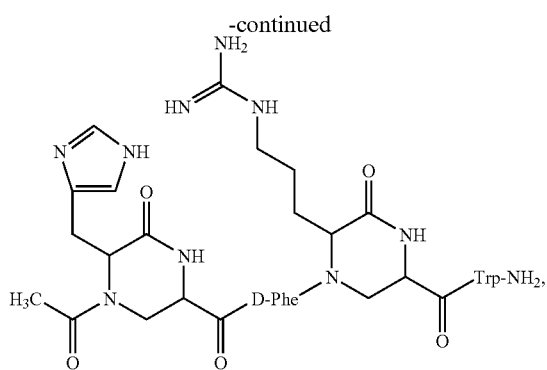

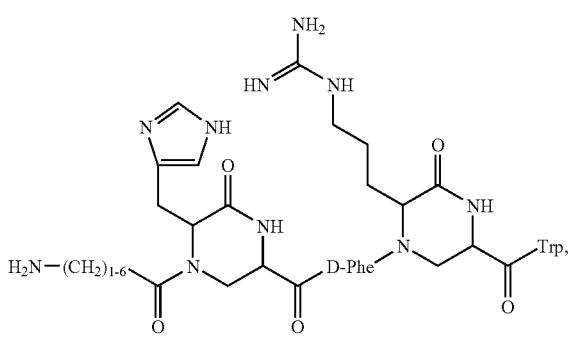

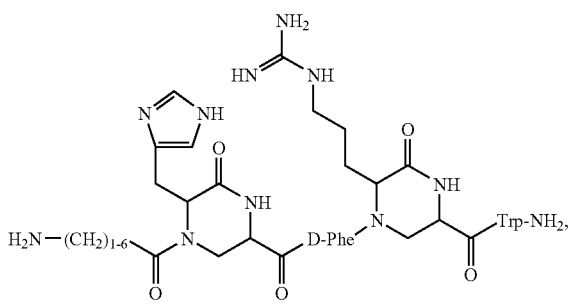

and the like, and further that such peptidomimetics may be cyclic as well as linear, and in particular that peptidomimetics with at least about four, five, six, seven or eight amino acid residues and two surrogates of formula I may be cyclized. The cyclic peptidomimetics may be have a cyclic bond that includes an N-terminus group, a C-terminus group, an $R^1$ group of a surrogate of formula I, or one or two amino acid side chain moieties. The cyclic bond may include a covalent bond such as an amide, disulfide, thioether, Schiff base, reduced Schiff base, imide, secondary amine, carbonyl, urea, hydrazone or oxime bond. It is thus possible, by way of example, to immediately envision any of the peptidomimetics given in the Examples as having two surrogates, by substituting one amino acid residue in any of the peptidomimetics by a surrogate.

12. Examples

The invention is further illustrated by the following non-limiting examples.

Peptidomimetic 12.1: A peptidomimetic was synthesized utilizing an N-terminus surrogate of the formula:

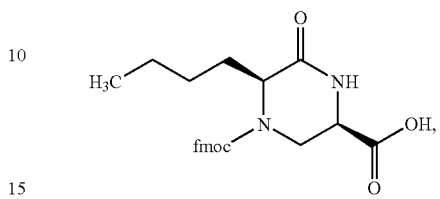

which was made by the method of Scheme C. The remainder of the peptidomimetic consisted of the sequence Asp-His-D-Phe-Arg-Trp-Lys-NH$_2$, with a lactam bridge formed between the amino acid side chains of Asp and Lys. The Fmoc group of the surrogate was removed after coupling to peptide, and the resulting amino group acetylated before cleaving the peptidomimetic from resin. The peptidomimetic had the formula:

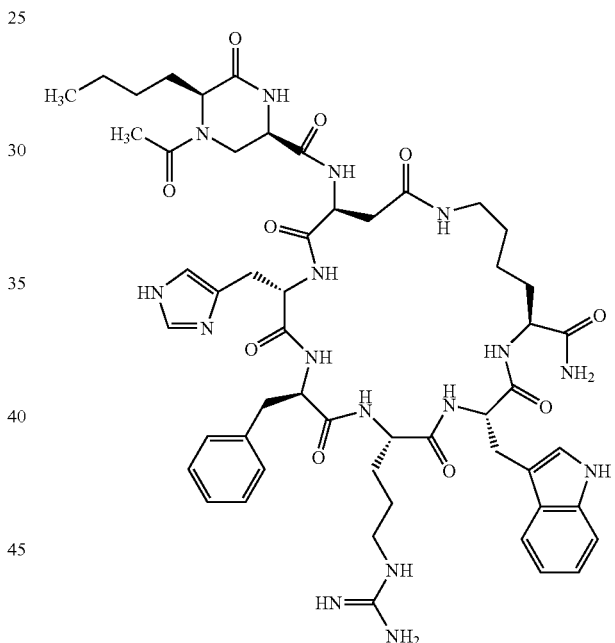

and a molecular formula of $C_{53}H_{72}N_{16}O_{10}$. The peptidomimetic was prepared as the TFA salt, and had a molecular weight of 1322.3 with the salt, and 1093.2 without the salt. In competitive inhibition studies, the peptidomimetic had a Ki of 2 nM at MC1-R, of 962 nM at MC3-R, and of 14 nM at MC4-R.

Peptidomimetic 12.2: A peptidomimetic was synthesized utilizing an N-terminus surrogate of the formula:

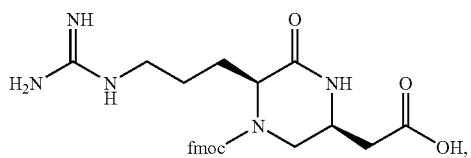

which was made by the method of Scheme C. The remainder of the peptidomimetic consisted of the sequence Asp-Ser (Bzl)-D-Phe-Arg-Trp-Lys-NH$_2$, with a lactam bridge formed between the amino acid side chains of Asp and Lys. The Fmoc group of the surrogate was removed after coupling to peptide, and the resulting amino group acetylated before cleaving the peptidomimetic from resin. The peptidomimetic had the formula:

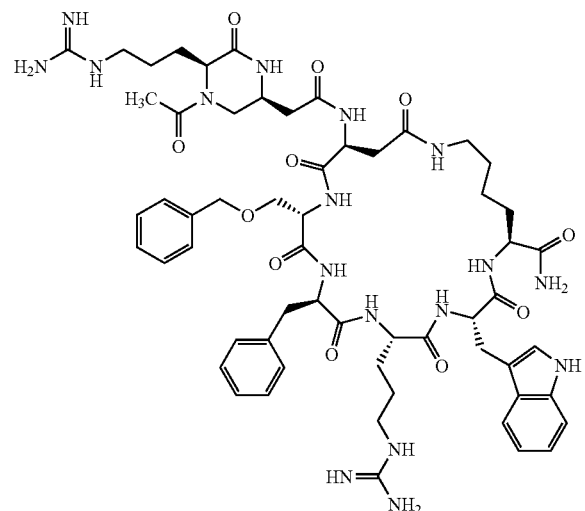

and a molecular formula of $C_{58}H_{79}N_{17}O_{11}$. The peptidomimetic was prepared as the AcOH salt, and had a molecular weight of 1310.5 with the salt, and 1190.4 without the salt. In competitive inhibition studies, the peptidomimetic had a Ki of 3.8 nM at MC4-R.

Peptidomimetic 12.3: A peptidomimetic was synthesized utilizing an N-terminus surrogate of the formula:

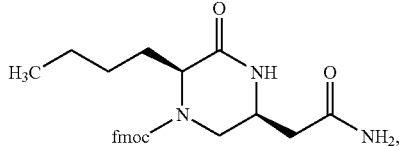

which was made by the method of Scheme C. The remainder of the peptidomimetic consisted of the sequence Asp-Ser (Bzl)-D-Phe-Arg-Trp-Lys-NH$_2$, with a lactam bridge formed between the amino acid side chains of Asp and Lys. The Fmoc group of the surrogate was removed after coupling to peptide, and the resulting amino group acetylated before cleaving the peptidomimetic from resin. The peptidomimetic had the formula:

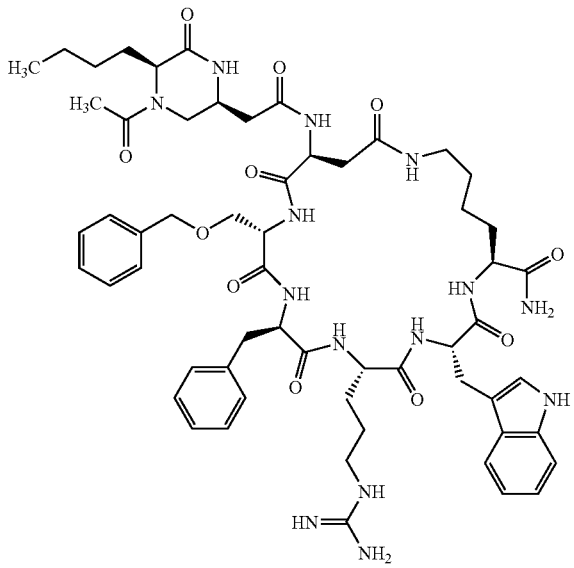

and a molecular formula of $C_{58}H_{78}N_{14}O_{11}$. The peptidomimetic was prepared as the AcOH salt, and had a molecular weight of 1207.4 with the salt, and 1147.3 without the salt. In competitive inhibition studies, the peptidomimetic had a Ki of 34 nM at MC4-R.

Peptidomimetic 12.4: A peptidomimetic was synthesized utilizing an N-terminus surrogate of the formula:

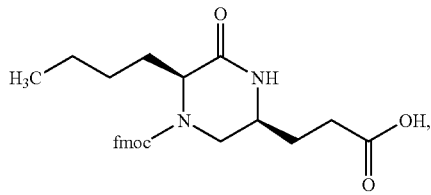

which was made by the method of Scheme C. The remainder of the peptidomimetic consisted of the sequence Asp-Ser (Bzl)-D-Phe-Arg-Trp-Lys-NH$_2$, with a lactam bridge formed between the amino acid side chains of Asp and Lys. The Fmoc group of the surrogate was removed after coupling to peptide, and the resulting amino group acetylated before cleaving the peptidomimetic from resin. The peptidomimetic had the formula:

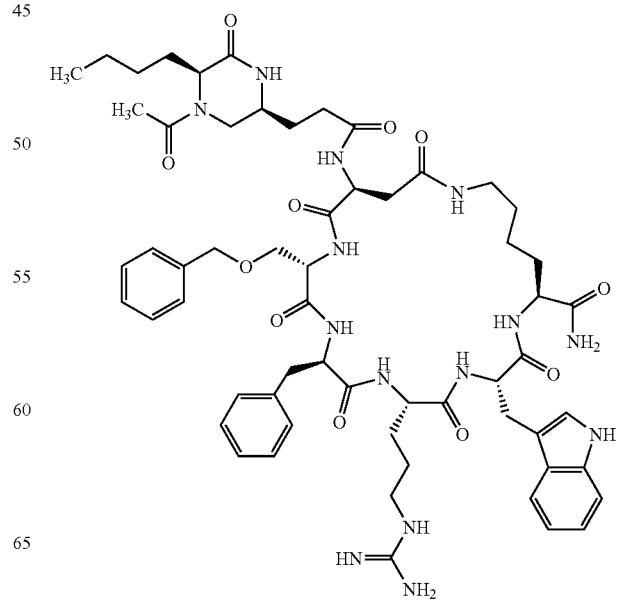

and a molecular formula of $C_{58}H_{80}N_{14}O_{11}$. The peptidomimetic was prepared as the AcOH salt, and had a molecular weight of 1221.4 with the salt, and 1161.3 without the salt. In competitive inhibition studies, the peptidomimetic had a Ki of 4 nM at MC4-R.

Peptidomimetic 12.5: A peptidomimetic was synthesized utilizing an N-terminus surrogate of the formula:

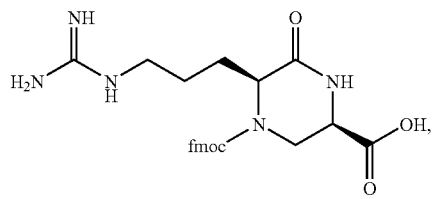

which was made by the method of Scheme C. The remainder of the peptidomimetic consisted of the sequence Asp-Ser(Bzl)-D-Phe-Arg-Trp-Lys-NH$_2$, with a lactam bridge formed between the amino acid side chains of Asp and Lys. The Fmoc group of the surrogate was removed after coupling to peptide, and the resulting amino group acetylated before cleaving the peptidomimetic from resin. The peptidomimetic had the formula:

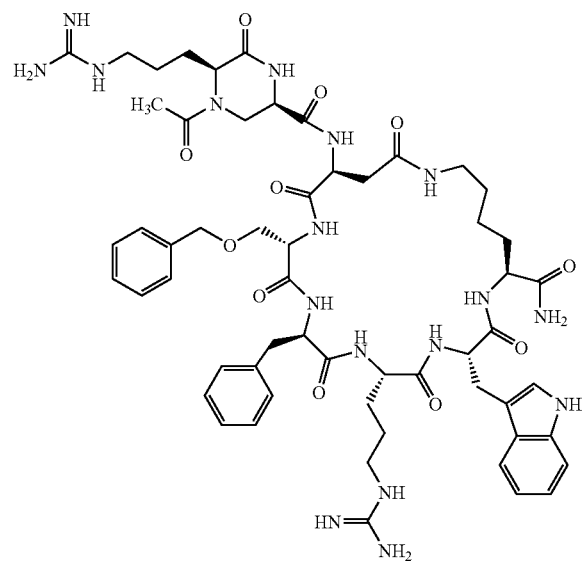

and a molecular formula of $C_{57}H_{77}N_{17}O_{11}$. The peptidomimetic was prepared as the TFA salt, and had a molecular weight of 1404.4 with the salt, and 1176.3 without the salt. In competitive inhibition studies, the peptidomimetic had a Ki of 4.6 nM at MC4-R.

Peptidomimetic 12:6: A peptidomimetic was synthesized utilizing an N-terminus surrogate of the formula:

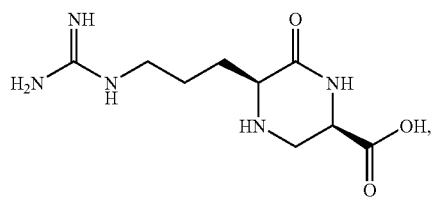

which was made by the method of Scheme C. The remainder of the peptidomimetic consisted of the sequence Asp-Ser(Bzl)-D-Phe-Arg-Trp-Lys-NH$_2$, with a lactam bridge formed between the amino acid side chains of Asp and Lys. The Fmoc group of the surrogate was removed after coupling to peptide. The peptidomimetic had the formula:

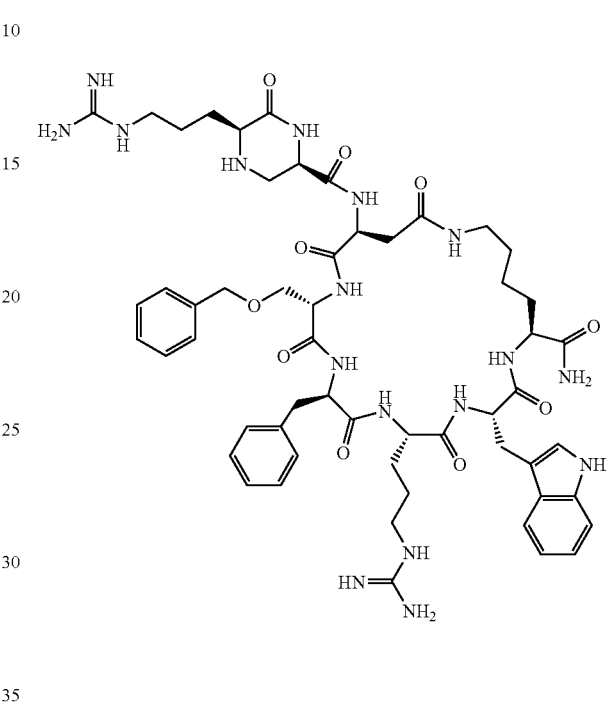

and a molecular formula of $C_{55}H_{75}N_{17}O_{10}$. The peptidomimetic was prepared as the TFA salt, and had a molecular weight of 1476.3 with the salt, and 1134.3 without the salt. In competitive inhibition studies, the peptidomimetic had a Ki of 3.2 nM at MC4-R.

Peptidomimetic 12:7: A peptidomimetic was synthesized utilizing an N-terminus surrogate of the formula:

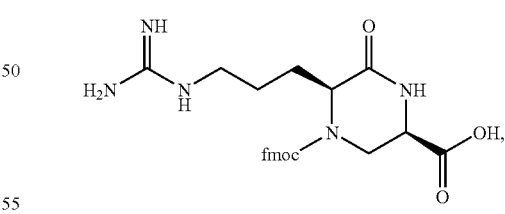

which was made by the method of Scheme C. The remainder of the peptidomimetic consisted of the sequence Asp-Gln-D-Phe-Arg-Trp-Lys-NH$_2$, with a lactam bridge formed between the amino acid side chains of Asp and Lys. The Fmoc group of the surrogate was removed after coupling to peptide, and the resulting amino group acetylated before cleaving the peptidomimetic from resin. The peptidomimetic had the formula:

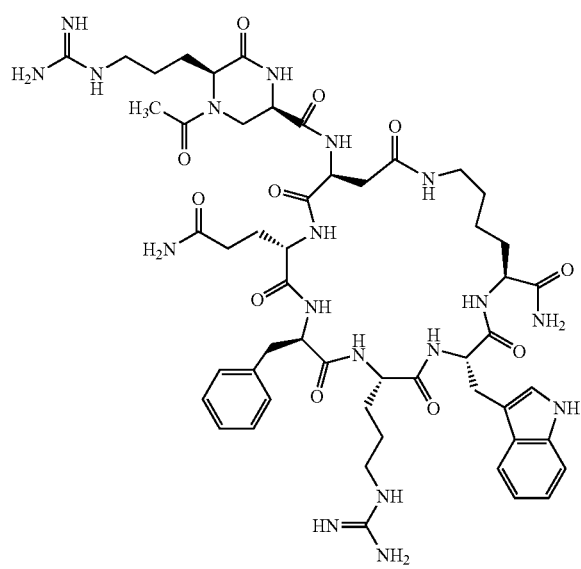

and a molecular formula of $C_{52}H_{74}N_{18}O_{11}$. The peptidomimetic was prepared as the TFA salt, and had a molecular weight of 1355.3 with the salt, and 1127.3 without the salt.

Peptidomimetic 12:8: A peptidomimetic was synthesized utilizing an N-terminus surrogate of the formula:

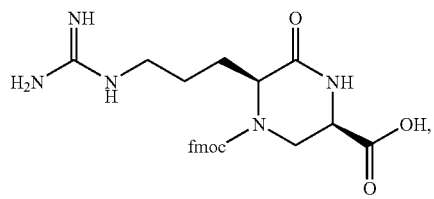

which was made by the method of Scheme C. The remainder of the peptidomimetic consisted of the sequence Asp-Asn-D-Phe-Arg-Trp-Lys-NH$_2$, with a lactam bridge formed between the amino acid side chains of Asp and Lys. The Fmoc group of the surrogate was removed after coupling to peptide, and the resulting amino group acetylated before cleaving the peptidomimetic from resin. The peptidomimetic had the formula:

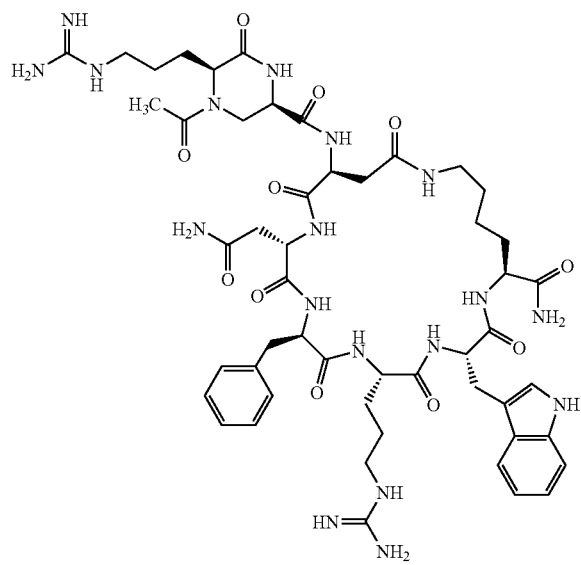

and a molecular formula of $C_{51}H_{72}N_{18}O_{11}$. The peptidomimetic was prepared as the TFA salt, and had a molecular weight of 1341.3 with the salt, and 1113.2 without the salt. In competitive inhibition studies, the peptidomimetic had a Ki of 77 nM at MC4-R.

Peptidomimetic 12:9: A peptidomimetic was synthesized utilizing an N-terminus surrogate of the formula:

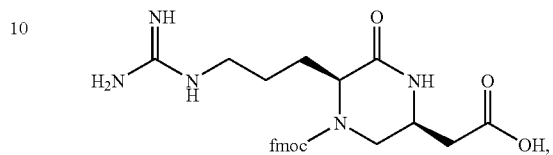

which was made by the method of Scheme C. The remainder of the peptidomimetic consisted of the sequence Asp-His-D-Phe-Arg-Trp-Lys-NH$_2$, with a lactam bridge formed between the amino acid side chains of Asp and Lys. The Fmoc group of the surrogate was removed after coupling to peptide, and the resulting amino group acetylated before cleaving the peptidomimetic from resin. The peptidomimetic had the formula:

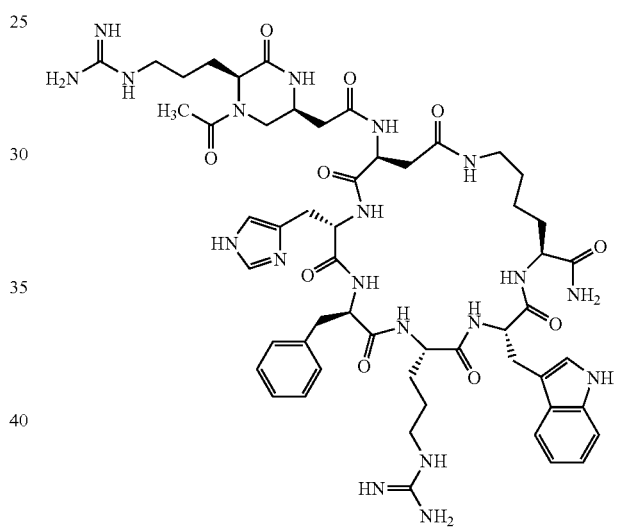

and a molecular formula of $C_{54}H_{75}N_{19}O_{10}$. The peptidomimetic was prepared as the TFA salt, and had a molecular weight of 1492.4 with the salt, and 1150.3 without the salt. In competitive inhibition studies, the peptidomimetic had a Ki of 3 nM at MC4-R.

Peptidomimetic 12:10: A peptidomimetic was synthesized utilizing an N-terminus surrogate of the formula:

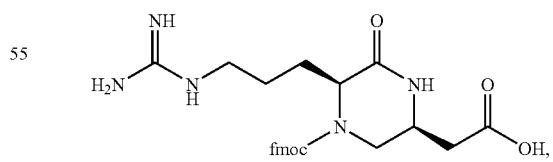

which was made by the method of Scheme C. The remainder of the peptidomimetic consisted of the sequence Asp-Gln-D-Phe-Arg-Trp-Lys-NH$_2$, with a lactam bridge formed between the amino acid side chains of Asp and Lys. The Fmoc group of the surrogate was removed after coupling to peptide, and the resulting amino group acetylated before cleaving the peptidomimetic from resin. The peptidomimetic had the formula:

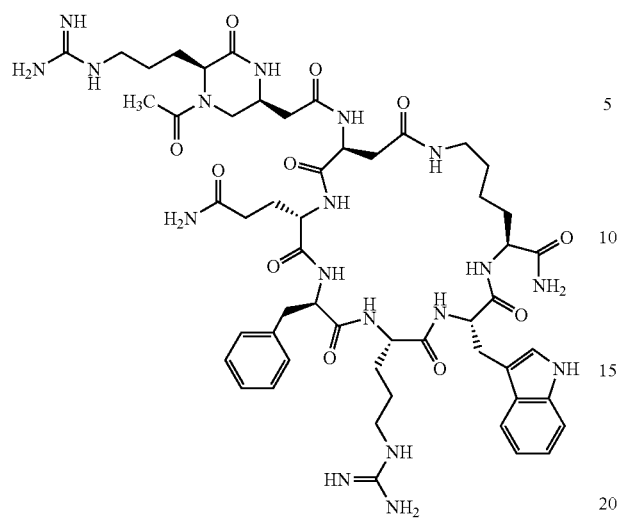

and a molecular formula of $C_{53}H_{76}N_{18}O_{11}$. The peptidomimetic was prepared as the TFA salt, and had a molecular weight of 1369.3 with the salt, and 1141.3 without the salt. In competitive inhibition studies, the peptidomimetic had a Ki of 30 nM at MC4-R.

Peptidomimetic 12:11: A peptidomimetic was synthesized utilizing an N-terminus surrogate of the formula:

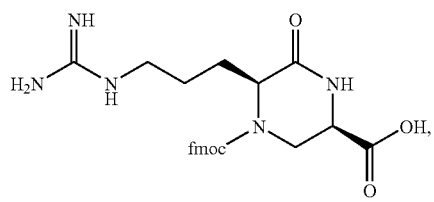

which was made by the method of Scheme C. The remainder of the peptidomimetic consisted of the sequence Asp-Ala-D-Phe-Arg-Trp-Lys-NH$_2$, with a lactam bridge formed between the amino acid side chains of Asp and Lys. The Fmoc group of the surrogate was removed after coupling to peptide, and the resulting amino group acetylated before cleaving the peptidomimetic from resin. The peptidomimetic had the formula:

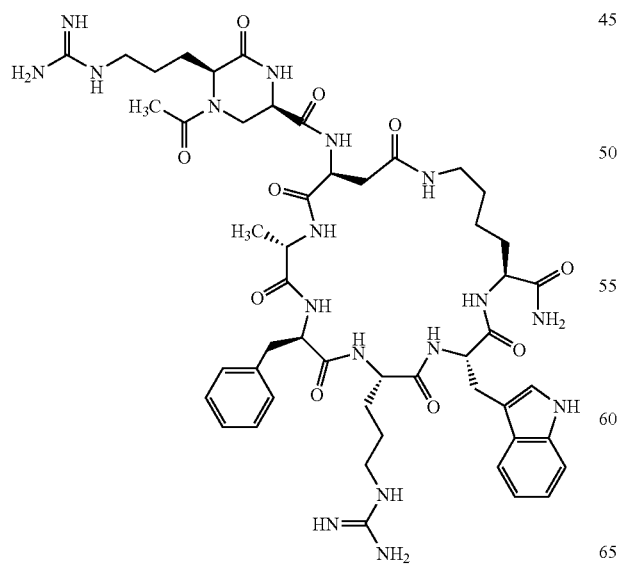

and a molecular formula of $C_{50}H_{71}N_{17}O_{10}$. The peptidomimetic was prepared as the TFA salt, and had a molecular weight of 1298.2 with the salt, and 1070.2 without the salt. In competitive inhibition studies, the peptidomimetic had a Ki of 91 nM at MC4-R.

Peptidomimetic 12:12: A peptidomimetic was synthesized utilizing an N-terminus surrogate of the formula:

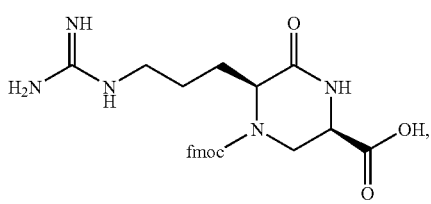

which was made by the method of Scheme C. The remainder of the peptidomimetic consisted of the sequence Asp-His-D-Phe-Arg-Trp-Lys-NH$_2$, with a lactam bridge formed between the amino acid side chains of Asp and Lys. The Fmoc group of the surrogate was removed after coupling to peptide, and the resulting amino group acetylated before cleaving the peptidomimetic from resin. The peptidomimetic had the formula:

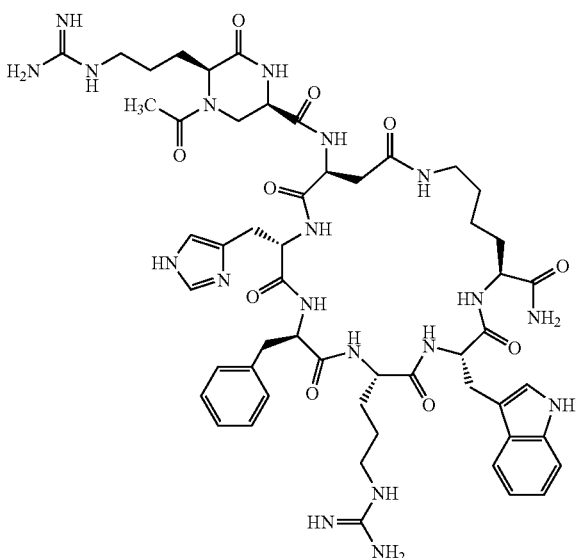

and a molecular formula of $C_{53}H_{73}N_{19}O_{10}$. The peptidomimetic was prepared as the TFA salt, and had a molecular weight of 1478.3 with the salt, and 1136.3 without the salt. In competitive inhibition studies, the peptidomimetic had a Ki of 10 nM at MC4-R.

Peptidomimetic 12-13: A peptidomimetic was synthesized utilizing a surrogate of the formula:

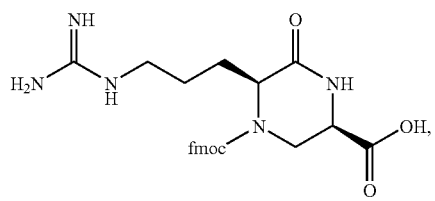

which was made by the method of Scheme C, in place of the Arg in the sequence Ala-D-Phe-Arg-Trp. The peptidomimetic consisted of the sequence Ac-Asp-Ala-D-Phe-surrogate-Trp-Lys-NH$_2$, with a lactam bridge formed between the amino acid side chains of Asp and Lys. The amino group of Asp was acetylated before cleaving the peptidomimetic from resin. The peptidomimetic had the formula:

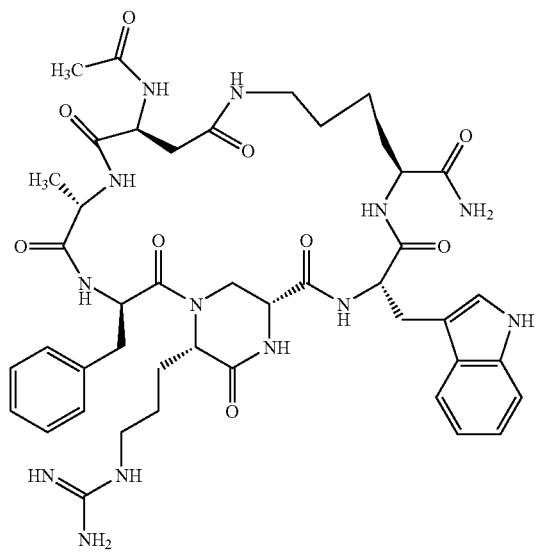

and a molecular formula of $C_{44}H_{59}N_{13}O_9$. The peptidomimetic was prepared as the TFA salt, and had a molecular weight of 1028.04 with the salt, and 914.02 without the salt.

Peptidomimetic 12-14: A peptidomimetic was synthesized utilizing a surrogate of the formula:

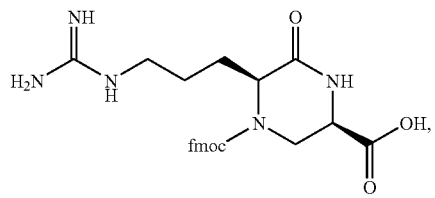

which was made by the method of Scheme C, in place of the Arg in the sequence Ala-D-Phe-Arg-Trp. The peptidomimetic consisted of the sequence Ac-Arg-Asp-Ala-D-Phe-surrogate-Trp-Lys-NH$_2$, with a lactam bridge formed between the amino acid side chains of Asp and Lys. The amino group of Arg was acetylated before cleaving the peptidomimetic from resin. The peptidomimetic had the formula:

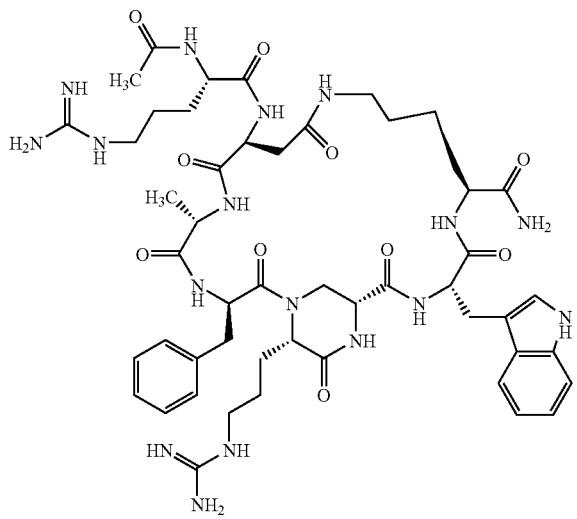

and a molecular formula of $C_{50}H_{71}N_{17}O_{10}$. The peptidomimetic was prepared as the TFA salt, and had a molecular weight of 1298.25 with the salt, and 1070.21 without the salt.

Peptidomimetic 12-15: A peptidomimetic was synthesized utilizing a surrogate of the formula:

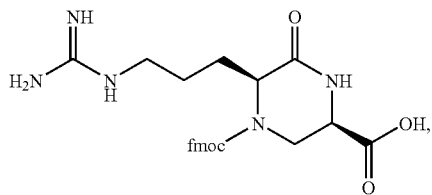

which was made by the method of Scheme C, in place of the Arg in the sequence Ala-D-Phe-Arg-Trp. The peptidomimetic consisted of the sequence Ac-Nle-Asp-Ala-D-Phe-surrogate-Trp-Lys-NH$_2$, with a lactam bridge formed between the amino acid side chains of Asp and Lys. The amino group of Nle was acetylated before cleaving the peptidomimetic from resin. The peptidomimetic had the formula:

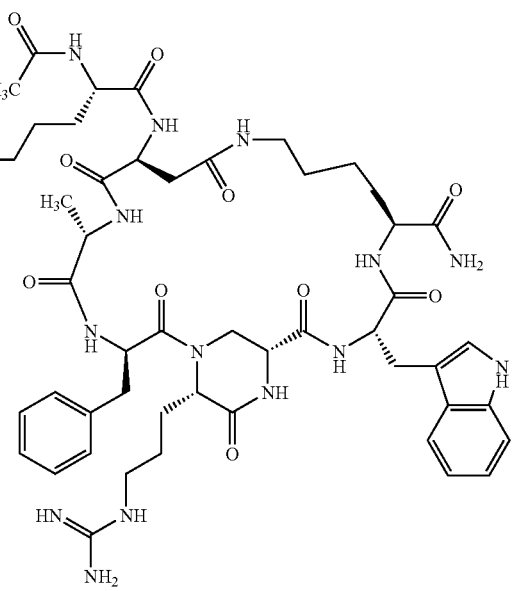

and a molecular formula of $C_{50}H_{70}N_{14}O_{10}$. The peptidomimetic was prepared as the TFA salt, and had a molecular weight of 1141.20 with the salt, and 1027.18 without the salt.

Peptidomimetic 12-16: A peptidomimetic was synthesized utilizing a surrogate of the formula:

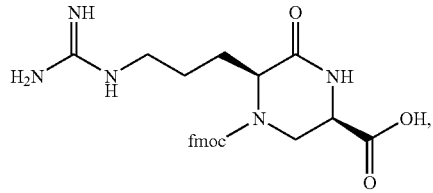

which was made by the method of Scheme C, in place of the Arg in the sequence His-D-Phe-Arg-Trp. The peptidomimetic consisted of the sequence Ac-Asp-His-D-Phe-surrogate-Trp-Lys-NH$_2$, with a lactam bridge formed between the amino acid side chains of Asp and Lys. The amino group of Nle was acetylated before cleaving the peptidomimetic from resin. The peptidomimetic had the formula:

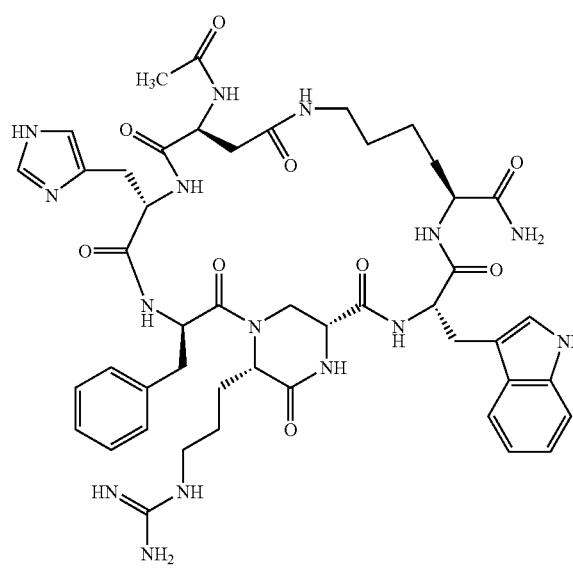

and a molecular formula of $C_{47}H_{61}N_{15}O_9$. The peptidomimetic was prepared as the TFA salt, and had a molecular weight of 1208.12 with the salt, and 980.08 without the salt.

Peptidomimetic 12-17: A peptidomimetic was synthesized utilizing a surrogate of the formula:

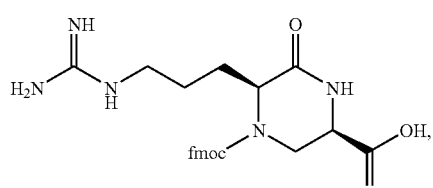

which was made by the method of Scheme C, in place of the Arg in the sequence His-D-Phe-Arg-Trp. The peptidomimetic consisted of the sequence Ac-Arg-Asp-His-D-Phe-surrogate-Trp-Lys-NH$_2$, with a lactam bridge formed between the amino acid side chains of Asp and Lys. The amino group of Arg was acetylated before cleaving the peptidomimetic from resin. The peptidomimetic had the formula:

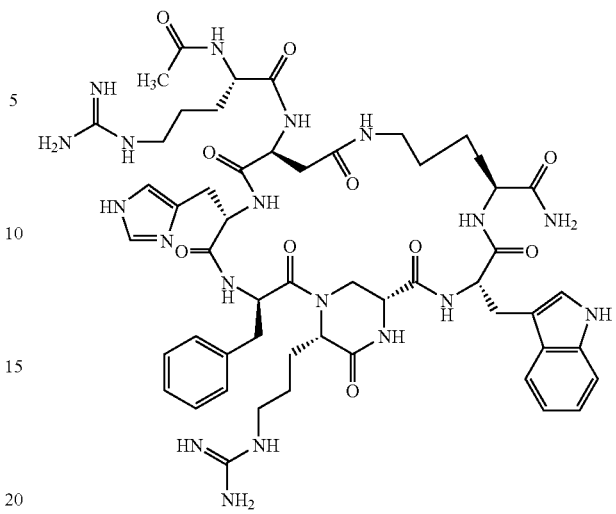

and a molecular formula of $C_{53}H_{73}N_{19}O_{10}$. The peptidomimetic was prepared as the TFA salt, and had a molecular weight of 1478.33 with the salt, and 1136.27 without the salt. In competitive inhibition studies, the peptidomimetic had a Ki of 496 nM at MC4-R.

Peptidomimetic 12-18: A peptidomimetic was synthesized utilizing a surrogate of the formula:

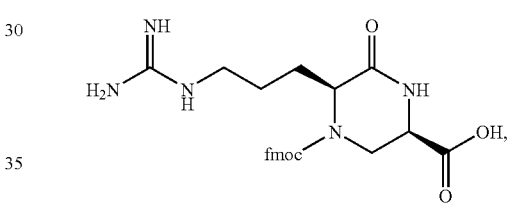

which was made by the method of Scheme C, in place of the Arg in the sequence His-D-Phe-Arg-Trp. The peptidomimetic consisted of the sequence Ac-Nle-Asp-His-D-Phe-surrogate-Trp-Lys-NH$_2$, with a lactam bridge formed between the amino acid side chains of Asp and Lys. The amino group of Nle was acetylated before cleaving the peptidomimetic from resin. The peptidomimetic had the formula:

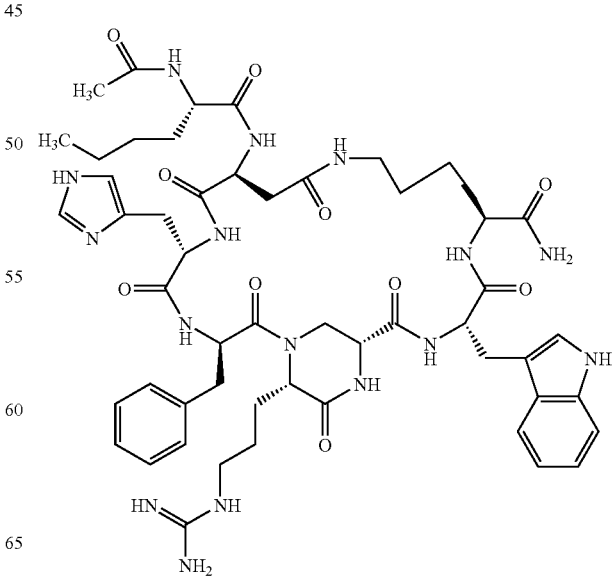

and a molecular formula of $C_{53}H_{72}N_{16}O_{10}$. The peptidomimetic was prepared as the TFA salt, and had a molecular weight of 1321.28 with the salt, and 1093.24 without the salt. In competitive inhibition studies, the peptidomimetic had a Ki of 50 nM at MC4-R.

Peptidomimetic 12-19: A peptidomimetic was synthesized utilizing a surrogate of the formula:

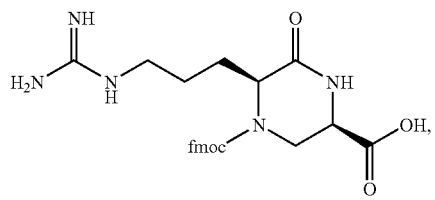

which was made by the method of Scheme C, in place of the Arg in the sequence Gln-D-Phe-Arg-Trp. The peptidomimetic consisted of the sequence Ac-Asp-Gln-D-Phe-surrogate-Trp-Lys-$NH_2$, with a lactam bridge formed between the amino acid side chains of Asp and Lys. The amino group of Asp was acetylated before cleaving the peptidomimetic from resin. The peptidomimetic had the formula:

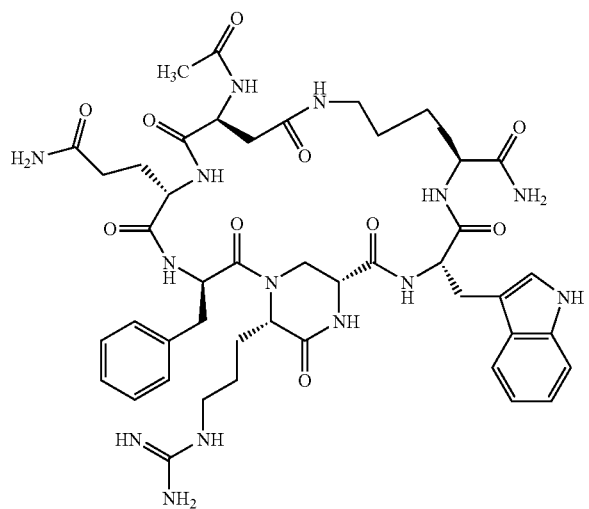

and a molecular formula of $C_{47}H_{63}N_{15}O_9$. The peptidomimetic was prepared as the TFA salt, and had a molecular weight of 1085.09 with the salt, and 971.07 without the salt.

Peptidomimetic 12-20: A peptidomimetic was synthesized utilizing a surrogate of the formula:

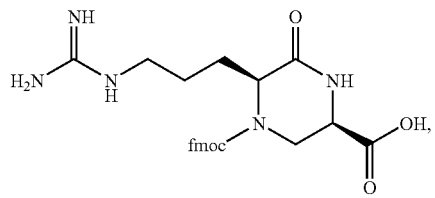

which was made by the method of Scheme C, in place of the Arg in the sequence Gln-D-Phe-Arg-Trp. The peptidomimetic consisted of the sequence Ac-Arg-Asp-Gln-D-Phe-surrogate-Trp-Lys-$NH_2$, with a lactam bridge formed between the amino acid side chains of Asp and Lys. The amino group of Arg was acetylated before cleaving the peptidomimetic from resin. The peptidomimetic had the formula:

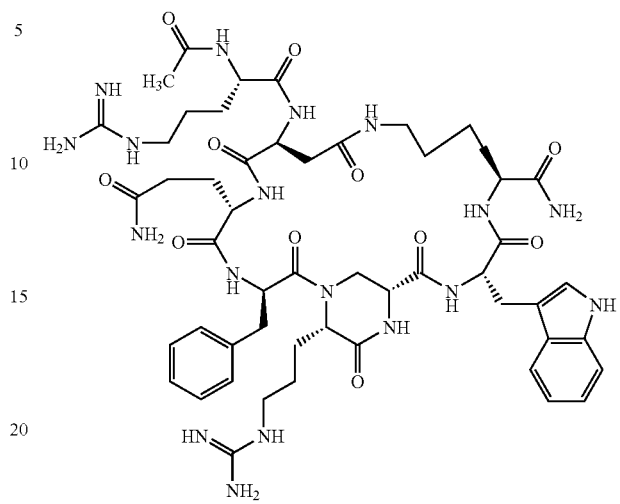

and a molecular formula of $C_{52}H_{74}N_{18}O_{11}$. The peptidomimetic was prepared as the TFA salt, and had a molecular weight of 1355.30 with the salt, and 1127.26 without the salt.

Peptidomimetic 12-21: A peptidomimetic was synthesized utilizing a surrogate of the formula:

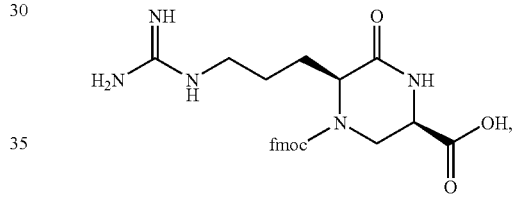

which was made by the method of Scheme C, in place of the Arg in the sequence Gln-D-Phe-Arg-Trp. The peptidomimetic consisted of the sequence Ac-Nle-Asp-Gln-D-Phe-surrogate-Trp-Lys-$NH_2$, with a lactam bridge formed between the amino acid side chains of Asp and Lys. The amino group of Nle was acetylated before cleaving the peptidomimetic from resin. The peptidomimetic had the formula:

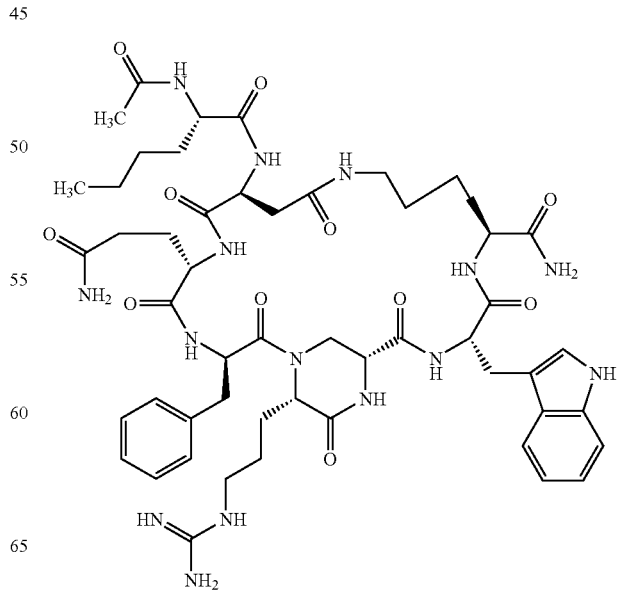

and a molecular formula of $C_{52}H_{73}N_{15}O_{11}$. The peptidomimetic was prepared as the TFA salt, and had a molecular weight of 1198.25 with the salt, and 1084.23 without the salt. In competitive inhibition studies, the peptidomimetic had a Ki of 257 nM at MC4-R.

Peptidomimetic 12-22: A peptidomimetic was made as for Peptidomimetic 12-7, except that the peptidomimetic was a free acid that had the formula:

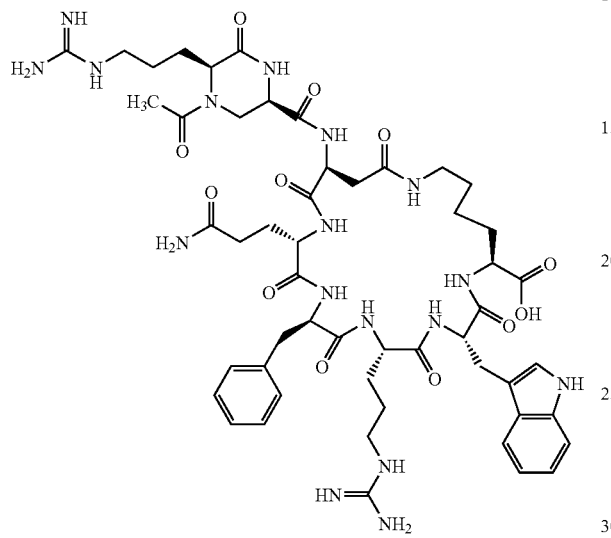

and a molecular formula of $C_{52}H_{73}N_{17}O_{12}$. The peptidomimetic was prepared as the TFA salt, and had a molecular weight of 1356.28 with the salt, and 1128.24 without the salt.

Peptidomimetic 12-23: A peptidomimetic was made as for Peptidomimetic 12-22, except that the amino group resulting from removal of the Fmoc group of the surrogate after coupling to the peptide was not acetylated, such that peptidomimetic was a free acid that had the formula:

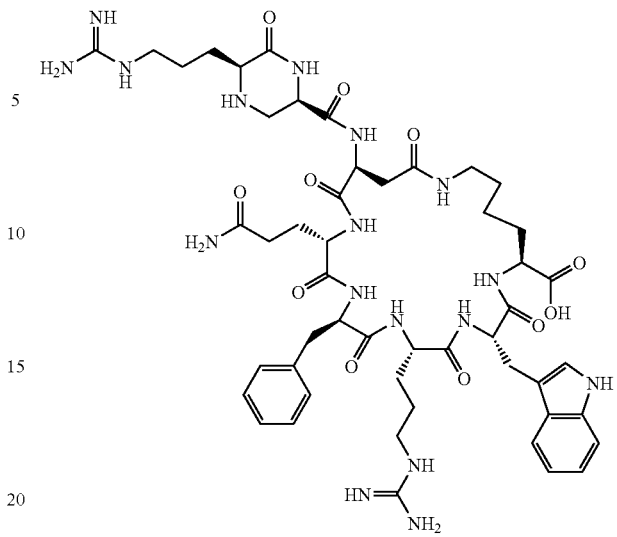

and a molecular formula of $C_{50}H_{71}N_{17}O_{11}$. The peptidomimetic was prepared as the TFA salt, and had a molecular weight of 1428.27 with the salt, and 1086.21 without the salt.

Each of the foregoing is merely illustrative, and other equivalent embodiments are possible and contemplated.

Although this invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above are hereby incorporated by reference.

The preceding examples can be repeated with similar success by substituting the generically or specifically described reactants and/or operating conditions of this invention for those used in the preceding examples.

What is claimed is:

1. A peptidomimetic of the formula

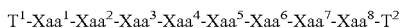

or a pharmaceutically acceptable salt thereof, wherein:

$T^1$ is H or an N-terminal group;

$Xaa^1$ is optionally present, and if present, is an amino acid with a side chain including at least one primary amine, guanidine, urea, alkyl or cycloalkyl, or $Xaa^1$ is an amino acid surrogate of the structure:

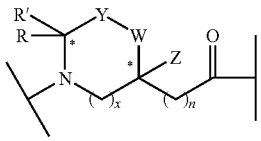

wherein the solid lines indicate a bond; R and R' are independently H, a linear or branched $C_1$ to $C_6$ aliphatic chain, $-(CH_2)_y-S-CH_3$, $-(CH_2)_y-S(=O)-CH_3$, $-(CH_2)_y-S(O_2)-CH_3$, $-(CH_2)_y-NH_2$, $-(CH_2)_y-NH-C(=NH)-NH_2$, $-(CH_2)_y-NH-(CH_2)_y-NH_2$, $-(CH_2)_y-NH-C(=O)-NH_2$, $-(CH_2)_y-C(=O)-NH_2$, a bond and a cyclopropane, cyclobutane, cyclopentane, or cyclohexane ring, or a $C_1$ to $C_3$ aliphatic chain and a cyclopropane, cyclobutane, cyclopentane, or cyclohexane ring; x is 1 or 2; Y is $CH_2$ or $C=O$; W is $CH_2$, NH or NR'''; Z is H or $CH_3$; R''' is an acyl, a $C_1$ to $O_{17}$ linear or branched alkyl chain, a $C_2$ to $C_{19}$ linear or branched alkyl acyl chain, a $C_1$ to $C_{17}$ linear or branched omega amino aliphatic, or a $C_1$ to $C_{17}$ linear or branched omega amino aliphatic acyl; n is 0, 1 or 2; m is 0 to 17; y is 1 to 5; and the carbon atoms marked with an asterisk can have any stereochemical configuration;

$Xaa^2$ and $Xaa^7$ are the same or different, and are each L- or D-isomer amino acid residues forming a cyclic bridge through the side chains of each of $Xaa^2$ and $Xaa^7$, wherein the linking group of the cyclic bridge comprises $-S-S-$, $-S-CH_2-S-$, $-S-CH_2-$, $-CH_2-S-$, $-C(=O)-NH$, $-NH-C(=O)-$, $-CH_2-NH-$, $-NH-CH_2-$, $-CH_2-S(O)_n-$ where n is 1 or 2, $-S(O)_n-CH_2-$ where n is 1 or 2, $-CH_2-CH_2-$, $-CH=CH-$ (E or Z), $-C\equiv C-$, $-C(=O)-O-$, $-O-C(=O)-$, $-C(=O)-CH_2-$, $-CH_2-C(=O)-$, $-NH-C(=O)-(CH_2)_m-C(=O)-NH-$ where m is from 1 to about 8, $-C(=O)-(CH_2)_m-C(=O)-$ where m is from 1 to about 8, $-O-C(=O)-NH-$, $-NH-C(=O)-O-$, or $-NH-C(=O)-NH-$;

$Xaa^3$ is an amino acid with a side chain including at least one primary amine, secondary amine, amide, alkyl, cycloalkyl, cycloheteroalkyl, aryl, heteroaryl, ether, sulfide, or carboxyl, or $Xaa^3$ is Pro, optionally substituted with hydroxyl, halogen, sulfonamide, alkyl, alkoxy, aryl, alkylaryl, alkylaryloxy, alkyl-alkoxy-aryl, or aryloxy;

$Xaa^4$ is an amino acid with a side chain including phenyl or naphthyl, optionally substituted with one or more ring substituents, and when one or more substituents are present, are the same or different and independently alkyl, haloalkyl, cycloalkyl, alkoxy, alkylhio, halo, nitro, acyl, cyano, aryl, alkylaryl, aryloxy, amino, monosubstituted amino, disubstituted amino, sulfonamide, hydroxy, carboxy, or alkoxy-carbonyl;

$Xaa^5$ is Pro, an amino acid with a side chain including at least one primary amine, secondary amine, guanidine, urea, alkyl, cycloalkyl, cycloheteroalkyl, aryl, heteroaryl, or ether, or $Xaa^5$ is an amino acid surrogate of the structure:

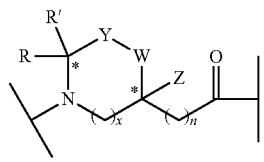

wherein the solid lines indicate a bond; at least one of R and R' is $(CH_2)_y-R''$ and if one, the remaining of R and R' is H, where R'' is:
—$NH_2$,
—$NH-C(=NH)-NH_2$,
—$NH-(CH_2)_y-NH_2$,
—$NH-C(=O)-NH_2$,
—$C(=O)-NH_2$,
—$C(=O)-NH-CH_3$,
—$C(=O)-NH-(CH_2)_y-NH_2$,
—$NH-C(=NH)-NH-Me$,
—$NH-C(=NH)-NH-Et$,
—$NH-C(=NH)-NH-Pr$,
—$NH-C(=NH)-NH-Pr-i$,
—$NH-C(=O)-CH_3$,
—$NH-C(=O)-CH_2-CH_3$,
—$NH-C(=O)-CH-(CH_3)_2$,
—$NH-C(=O)-O-CH_3$,
—$NH-C(=O)-O-CH_2-CH_3$,
—$NH-C(=O)-O-C-(CH_3)_3$,
—$NH-C(=O)-NH-CH_3$,
—$NH-C(=N-C(=O)-O-C-(CH_3)_3)-NH-C(=O)-O-C-(CH_3)_3$,
—$N(C(=O)-O-C-(CH_3)_3)-C(=NH)-NH-C(=O)-O-C-(CH_3)_3$,

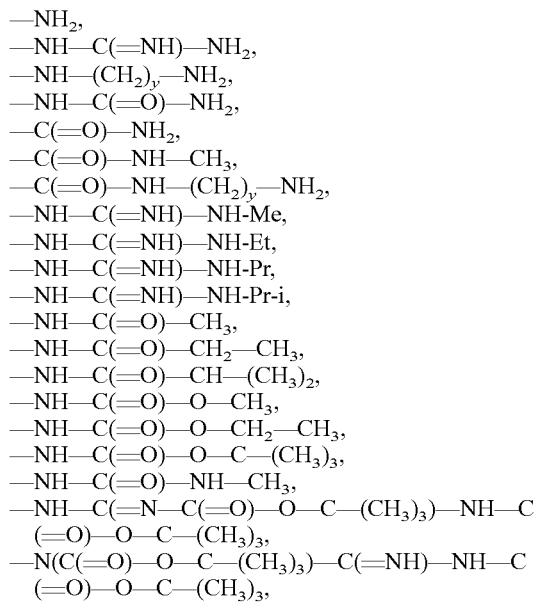

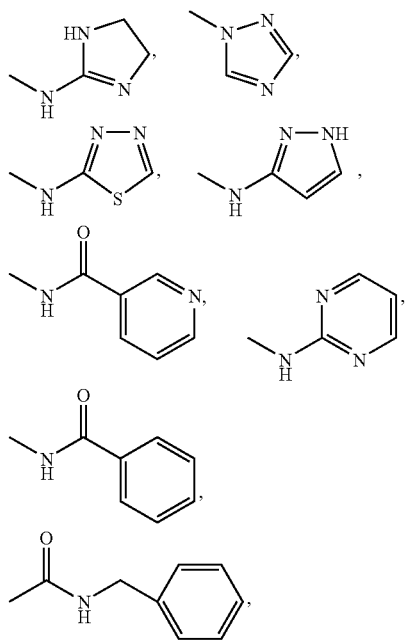

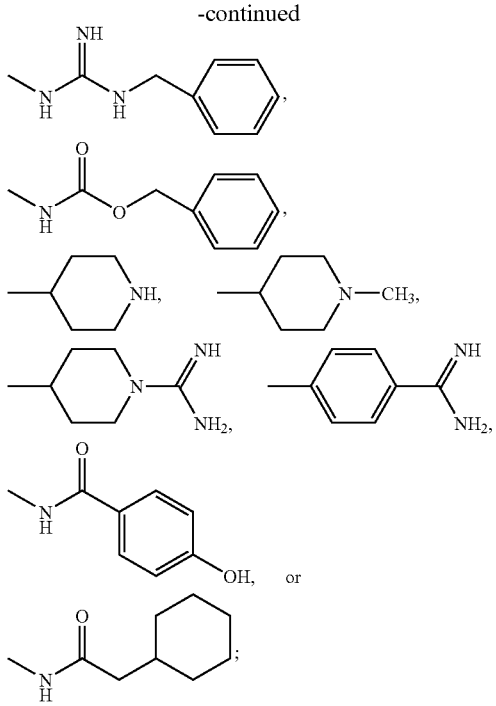

x is 1 or 2; Y is CH$_2$ or C=O; W is CH$_2$, NH or NR'''; Z is H or CH$_3$; R''' is an acyl, a C$_1$ to C$_{17}$ linear or branched alkyl chain, a C$_2$ to C$_{19}$ linear or branched alkyl acyl chain, a C$_1$ to C$_{17}$ linear or branched omega amino aliphatic, or a C$_1$ to C$_{17}$ linear or branched omega amino aliphatic acyl; n is 0, 1 or 2; m is 0 to 17; y is 1 to 5; and the carbon atoms marked with an asterisk can have any stereochemical configuration;

Xaa$^6$ is an amino acid with a side chain including at least one aryl or heteroaryl, optionally substituted with one or more ring substituents, and when one or more substituents are present, are the same or different and independently alkyl, haloalkyl, cycloalkyl, alkoxy, alkylthio, halo, nitro, acyl, cyano, aryl, alkylaryl, aryloxy, amino, monosubstituted amino, disubstituted amino, sulfonamide, hydroxy, carboxy, or alkoxy-carbonyl;

Xaa$^8$ is optionally present, and if present, is an amino acid with a side chain including at least one group capable of hydrogen bond donation or hydrogen bond acceptance; and T$^2$ is a C-terminal group;

on the proviso that at least one of Xaa$^1$ and Xaa$^6$ is an amino acid surrogate.

2. The peptidomimetic of claim 1 wherein Xaa$^1$ is an L- or D-isomer of Dap, Dab, Orn, Lys, Cit or Arg and Xaa$^5$ is an amino acid surrogate.

3. The peptidomimetic of claim 1 wherein Xaa$^4$ is D-Phe, optionally wherein the phenyl ring is substituted with one or more ring substituents, and when one or more substituents are present, are the same or different and independently alkyl, haloalkyl, cycloalkyl, alkoxy, alkylthio, halo, nitro, acyl, cyano, aryl, alkylaryl, aryloxy, amino, monosubstituted amino, disubstituted amino, sulfonamide, hydroxy, carboxy, or alkoxy-carbonyl.

4. The peptidomimetic of claim 1 wherein the cyclic bridge formed by the side chains of Xaa$^2$ and Xaa$^1$ comprises —C(=O)—NH— or —NH—C(=O)—.

5. The peptidomimetic of claim 1 wherein the N-terminal group is a C$_1$ to C$_7$ acyl group, a linear or branched C$_1$ to C$_{17}$ alkyl, aryl, heteroaryl, alkene, alkenyl, or aralkyl chain or an N-acylated linear or branched C$_1$ to C$_{17}$ alkyl, aryl, heteroaryl, alkene, alkenyl, or aralkyl chain and the C-terminal group is a carboxyl, an amide, an amide substituted with one or two linear or branched C$_1$ to C$_{17}$ alkyl, cycloalkyl, aryl, heteroaryl, alkylaryl, alkene, alkenyl, or aralkyl chains, or a linear or branched C$_1$ to C$_{17}$ alkyl, cycloalkyl, aryl, heteroaryl, alkene, alkenyl, or aralkyl chain.

6. The peptidomimetic of claim 1 wherein T$^1$-Xaa$^1$ is

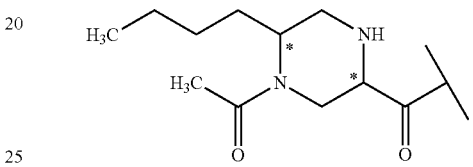

and the carbon atoms marked with an asterisk can have any stereochemical configuration.

7. The peptidomimetic of claim 6 of the formula:

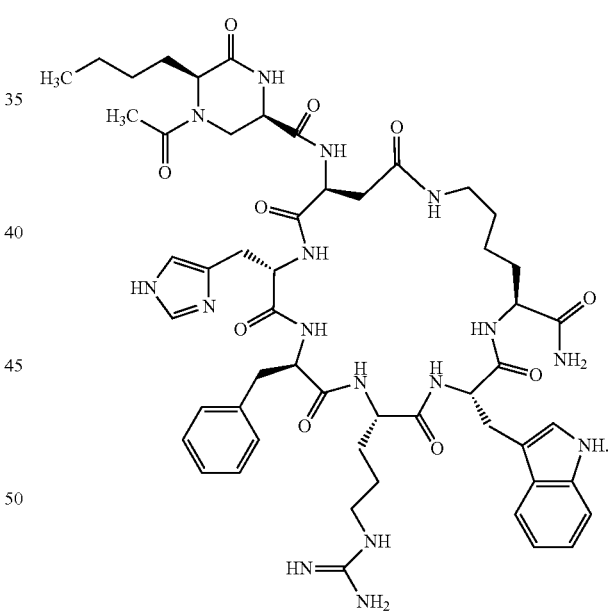

* * * * *

SEQUENCE LISTING

<160> NUMBER OF SEQ ID NOS: 1

<210> SEQ ID NO 1
<211> LENGTH: 4
<212> TYPE: PRT
<213> ORGANISM: Artificial
<220> FEATURE:
<223> OTHER INFORMATION: melanocortin binding sequence derived from
      alpha-MSH

<400> SEQUENCE: 1

His Phe Arg Trp
1